US006613881B1

(12) United States Patent
Alderson et al.

(10) Patent No.: US 6,613,881 B1
(45) **Date of Patent: *Sep. 2, 2003**

(54) COMPOUNDS FOR IMMUNOTHERAPY AND DIAGNOSIS OF TUBERCULOSIS AND METHODS OF THEIR USE

(75) Inventors: Mark Raymond Alderson, Bainbridge Island, WA (US); Davin C. Dillon, Redmond, WA (US); Yasir A. W. Skeiky, Seattle, WA (US); Antonio Campos-Neto, Bainbridge Island, WA (US)

(73) Assignee: Corixa Corporation, Seattle, WA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/073,010

(22) Filed: May 5, 1998

Related U.S. Application Data

(63) Continuation-in-part of application No. 08/859,381, filed on May 20, 1997, now abandoned.

(51) Int. Cl.[7] .......................... C07K 1/00; C07H 21/00; C12Q 1/68
(52) U.S. Cl. ........................... 530/350; 536/23.1; 435/6

(58) Field of Search ....................... 530/350; 424/184.1, 424/190.1, 248.1

(56) References Cited

U.S. PATENT DOCUMENTS

| | | | |
|---|---|---|---|
| 4,689,397 A | 8/1987 | Shinnick et al. | 530/327 |
| 4,879,213 A | 11/1989 | Fox et al. | 435/5 |
| 4,952,395 A | 8/1990 | Shinnick et al. | 424/92 |
| 5,330,754 A | 7/1994 | Kapoor et al. | 424/190.1 |
| 5,478,726 A | * 12/1995 | Shinnick et al. | |
| 6,037,135 A | * 3/2000 | Kubo et al. | 435/7.24 |

FOREIGN PATENT DOCUMENTS

| | | |
|---|---|---|
| WO | WO 97/09428 A2 | 3/1997 |
| WO | WO 97/09429 A2 | 3/1997 |

OTHER PUBLICATIONS

Goodman–Smitkoff et al., Vaccine, vol. 8, pp. 257–262, 1990.*
Riveau et al., TIPS, vol. 11., pp. 194–198, 1990.*
Arnon, Molecular Immunology, vol. 28, No. 2, pp. 209–215, 1991.*
Kaufmann et al., Immunobiology, vol. 184, pp. 208–229, 1992.*
Jacobs, Jr., Immunobiology, vol. 184, pp. 147–156, 1992.*
Philipp et al., Proceedings of the National Academy of Science (USA), vol. 93, pp. 3132–3137, 1996.*
Accession No. O05907, Database: stprembl19, publicly available Jul. 1, 1997.*
Accession No. O05908, Database: stprembl19, publicly available Jul. 1, 1997.*
Geysen et al. Cognitive features of continuous antigenic determinants. Journal of Molecular Recognition, vol. 1, pp. 32–41, 1988.*
Orme, I.M. Prospects for new vaccines against tuberculosis. Trends in Microbiology, vol. 3(10), pp. 401–404, 1995.*

(List continued on next page.)

*Primary Examiner*—Ardin H. Marschel
(74) *Attorney, Agent, or Firm*—Townsend and Townsend and Crew LLP

(57) ABSTRACT

Compounds and methods for inducing protective immunity against tuberculosis are disclosed. The compounds provided include polypeptides that contain at least one immunogenic portion of one or more *M. tuberculosis* proteins and DNA molecules encoding such polypeptides. Such compounds may be formulated into vaccines and/or pharmaceutical compositions for immunization against *M. tuberculosis* infection, or may be used for the diagnosis of tuberculosis.

13 Claims, 2 Drawing Sheets

D7 T Cell Proliferation

D7 IFNg

OTHER PUBLICATIONS

Figure 1A:
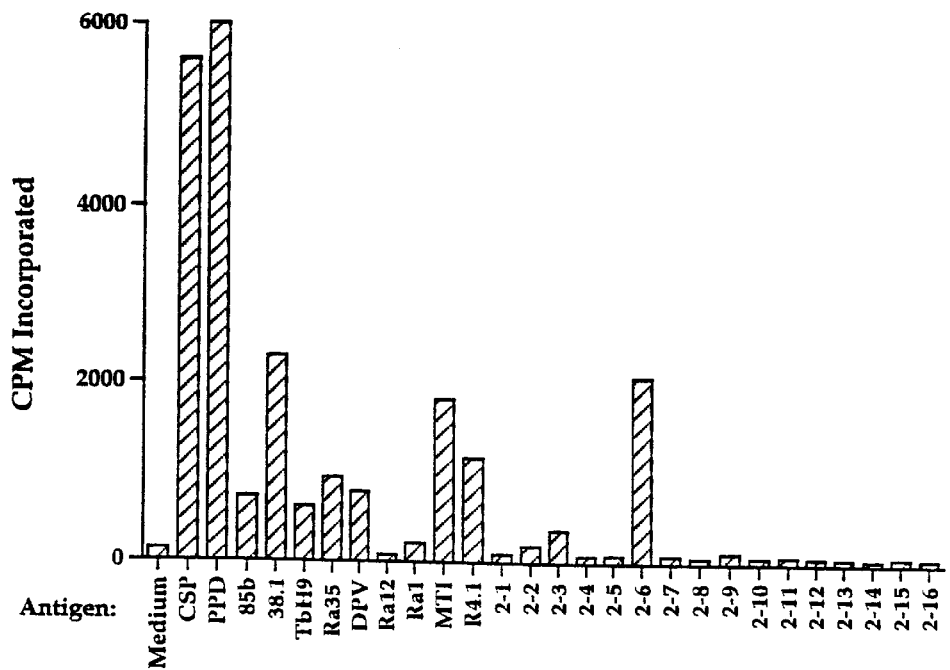

Greenway et al. Enhancement of protective immune responses to Venezuelan equine encephalitis (VEE) virus with microencapsulated vaccine. Vaccine, vol. 13, pp. 1411–1420, 1995.*

Andersen, et al., "Identification of Immunodominant Antigens during Infection with *Mycobacterium tuberculosis"; Scand. J. Immunol*. 36:823–831 (1992).

Andersen and Heron "Specificity of a Protective Memory Immune Response against *Mycobacterium tuberculosis" Infection and Immunity* 61(3):844–851 (1993).

Burgess et al. "Possible Dissociation of the Heparin–binding and Mitogenic Activities of Heparin–Binding (Acidic Fibroblast) Growth Factor–1 from its Receptor–binding Activities by Site–Directed Mutagenesis of a Single Lysine Residue" *J. Cell. Biol*. 111:2129–2138 (1990).

Eiglmeier et al. "Use of an ordered cosmid library to deduce the genomic organization of *Mycobacterium leprae" Mol. Microbiol*. 7(2):197–206 (1993).

Fifis et al. "Purification and Characterization of Major Antigens from a *Mycobacterium bovis* Culture Filtrate" *Infection and Immunity* 59(3):800–807 (1991).

Geysen et al. "Cognitive features of continuous antigenic determinants" *J. Mol. Recognition* 1:32–41(1988).

Greenway et al. "Enhancement of protective immune responses to Venezuelan equine encephalitis (VEE) virus with microencapsulated vaccine" *Vaccine* 13:1411–1420 (1995).

Kadival et al. "Radioimmunoassay of tuberculous antigen" *Indian J. Med. Res*. 75:765–770 (1982).

Lazar et al. "Transforming Growth Factor α: Mutation of Aspartic Acid 47 and Leucine 48 results in Different Biological Activities" *Mol. Cell. Biol*. 8(3):1247–1252 (1988).

Lee et al. "Characterization of the Major Membrane Protein of Virulent *Mycobacterium tuberculosis" Infection and Immunity* 60:2066–2074 (1992).

Mathur and Kolttukudy "Molecular cloning and sequencing of the gene for mycocerosic acid synthase, a novel fatty acid elongating multifunctional enzyme, from *Mycobacterium tuberculosis* var. *bovis Bacillus Calmette–Guerin" J. Biol. Chem*. 267:19388–19395 (1992).

Orme "Prospects for new vaccines against tuberculosis" *Trends in Microbiology* 3(10):401–404 (1995).

Pancholi et al. "Dendritic cells efficiently immunoselect mycobacteriual–reactive T cells in human blood, including clonable antigen–reactive precursors" *Immunology* 76(2):217–224 (1992).

Rinke de Wit et al. "A *Mycobacterium leprae*–specific gene encoding an immunologically recognized 45 kDa protein" *Mol. Microbiol*. 10(4):829–838 (1993).

Rinke de Wit et al. "Mycobacteria contains two groEL genes: the second *Mycobacterium leprae* groEL gene is arranged in an operon with groES" *Mol. Microbiol*. 6(14):1995–2007 (1992).

Romain et al. "Identification of a *Mycobacterium bovis* BCG 45/47–Kilodalton Antigen Complex, an Immunodominant Target for Antibody Response after Immunization with Living Bacteria" *Infection and Immunity* 61(2):742–750 (1993).

Sanderson et al. "Identification of a CD4+ T Cell–stimulating Antigen of Pathogenic Bacteria by Expression Cloning" *J. Exp. Med*. 182(6):1751–1757 (1995).

Vega–Lopez et al. "Sequence and immunological characterization of a serine–rich antigen from *Mycobacterium leprae" Infection and Immunity* 61(5):2145–2153 (1993).

Wieles et al. "Characterization of a *Mycobacterium leprae* Antigen Related to the Secreted *Mycobacterium tuberculosis* Protein MPT32" *Infection and Immunity* 62(1):252–258 (1994).

Database EMBL Empro, Entry MTCY7H7B, Accession No. Z95557, May 20, 1997.

Database EMBL Empro, Entry MTCY24G1, Accession No. Z83858, Jan. 13, 1997.

Databse EMBL Empro Entry MTCY19G5, Accession No. Z77826, Jul. 31, 1996.

Database EMBL Empro Entry MTCY261, Accession No. Z97559, Jul. 10, 1997.

* cited by examiner

COMPOUNDS FOR IMMUNOTHERAPY AND DIAGNOSIS OF TUBERCULOSIS AND METHODS OF THEIR USE

CROSS REFERENCE TO RELATED APPLICATIONS

This application is a continuation-in-part of U.S. patent application Ser. No. 08/859,381 filed May 20, 1997, now abandoned.

TECHNICAL FIELD

The present invention relates generally to detecting, treating and preventing Mycobacterium tuberculosis infection. The invention is more particularly related to polypeptides comprising a Mycobacterium tuberculosis antigen, or a portion or other variant thereof, and the use of such polypeptides for diagnosing and vaccinating against Mycobacterium tuberculosis infection.

BACKGROUND OF THE INVENTION

Tuberculosis is a chronic, infectious disease, that is generally caused by infection with Mycobacterium tuberculosis. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If left untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

Inhibiting the spread of tuberculosis requires effective vaccination and accurate, early diagnosis of the disease. Currently, vaccination with live bacteria is the most efficient method for inducing protective immunity. The most common Mycobacterium employed for this purpose is Bacillus Calmette-Guerin (BCG), an avirulent strain of Mycobacterium bovis. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable induration at the injection site by 48–72 hours after injection, which indicates exposure to Mycobacterial antigens. Sensitivity and specificity have, however, been a problem with this test, and individuals vaccinated with BCG cannot be distinguished from infected individuals.

While macrophages have been shown to act as the principal effectors of M. tuberculosis immunity, T cells are the predominant inducers of such immunity. The essential role of T cells in protection against M. tuberculosis infection is illustrated by the frequent occurrence of M. tuberculosis in AIDS patients, due to the depletion of CD4 T cells associated with human immunodeficiency virus (HIV) infection. Mycobacterium-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit M. tuberculosis infection. Furthermore, it is known that IFN-γ stimulates human macrophages to make 1,25-dihydroxy-vitamin D3. Similarly, IL-12 has been shown to play a role in stimulating resistance to M. tuberculosis infection. For a review of the immunology of M. tuberculosis infection see Chan and Kaufmann in Tuberculosis: Pathogenesis, Protection and Control, Bloom (ed.), ASM Press, Washington, D.C., 1994.

Accordingly, there is a need in the art for improved vaccines and methods for preventing, treating and detecting tuberculosis. The present invention fulfills these needs and further provides other related advantages.

SUMMARY OF THE INVENTION

Briefly stated, this invention provides compounds and methods for preventing and diagnosing tuberculosis. In one aspect, polypeptides are provided comprising an immunogenic portion of an M. tuberculosis antigen, or a variant of such an antigen that differs only in conservative substitutions and/or modifications, the antigen comprising an amino acid sequence encoded by a DNA sequence selected from the group consisting of the sequences recited in SEQ ID NO: 1, 11, 12, 83, 103–108, 125, 127, 129–137, 139 and 140, the complements of said sequences, and DNA sequences that hybridize to a sequence recited in SEQ ID NO: 1, 11, 12, 83, 103–108, 125, 127, 129–137, 139 and 140, or a complement thereof under moderately stringent conditions. In a second aspect, the present invention provides polypeptides comprising an immunogenic portion of a M. tuberculosis antigen having an amino acid sequence selected from the group consisting of sequences provided in SEQ ID NO: 16–33, 109, 126, 138, 141, 142 and variants thereof.

In related aspects, DNA sequences encoding the above polypeptides, expression vectors comprising these DNA sequences and host cells transformed or transfected with such expression vectors are also provided.

In another aspect, the present invention provides fusion proteins comprising a first and a second inventive polypeptide or, alternatively, an inventive polypeptide and a known M. tuberculosis antigen.

Within other aspects, the present invention provides pharmaceutical compositions that comprise one or more of the above polypeptides, or a DNA molecule encoding such polypeptides, and a physiologically acceptable carrier. The invention also provides vaccines comprising one or more of the polypeptides as described above and a non-specific immune response enhancer, together with vaccines comprising one or more DNA sequences encoding such polypeptides and a non-specific immune response enhancer.

In yet another aspect, methods are provided for inducing protective immunity in a patient, comprising administering to a patient an effective amount of one or more of the above polypeptides.

In further aspects of this invention, methods and diagnostic kits are provided for detecting tuberculosis in a patient. The methods comprise contacting dermal cells of a patient with one or more of the above polypeptides and detecting an immune response on the patient's skin. The diagnostic kits comprise one or more of the above polypeptides in combination with an apparatus sufficient to contact the polypeptide with the dermal cells of a patient.

In yet another aspect, methods are provided for detecting tuberculosis in a patient, such methods comprising contacting dermal cells of a patient with one or more polypeptides encoded by a DNA sequence selected from the group consisting of SEQ ID NO: 2–10, 102, 128, the complements of said sequences, and DNA sequences that hybridize to a sequence recited in SEQ ID NO: 2–10, 102, 128; and detecting an immune response on the patient's skin. Diagnostic kits for use in such methods are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A and 1B illustrate the stimulation of proliferation and interferon-γ production, respectively, in T cells derived from a first PPD-positive donor (referred to as D7) by recombinant ORF-2 and synthetic peptides to ORF-2.

FIGS. 2A and 2B illustrate the stimulation of proliferation and interferon-γ production, respectively, in T cells derived from a second PPD-positive donor (referred to as D160) by recombinant ORF-2 and synthetic peptides to ORF-2.

DETAILED DESCRIPTION OF THE INVENTION

As noted above, the present invention is generally directed to compositions and methods for preventing, treating and diagnosing tuberculosis. The compositions of the subject invention include polypeptides that comprise at least one immunogenic portion of a *M. tuberculosis* antigen, or a variant of such an antigen that differs only in conservative substitutions and/or modifications. As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native *M. tuberculosis* antigen or may be heterologous, and such sequences may (but need not) be immunogenic.

"Immunogenic," as used herein, refers to the ability to elicit an immune response (e.g., cellular) in a patient, such as a human, and/or in a biological sample. In particular, antigens that are immunogenic (and immunogenic portions or other variants of such antigens) are capable of stimulating cell proliferation, interleukin-12 production and/or interferon-γ production in biological samples comprising one or more cells selected from the group of T cells, NK cells, B cells and macrophages, where the cells are derived from an *M. tuberculosis*-immune individual. Polypeptides comprising at least an immunogenic portion of one or more *M. tuberculosis* antigens may generally be used to detect tuberculosis or to induce protective immunity against tuberculosis in a patient.

The compositions and methods of this invention also encompass variants of the above polypeptides. A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% identity to the identified polypeptides. For polypeptides with immunoreactive properties, variants may, alternatively, be identified by modifying the amino acid sequence of one of the above polypeptides, and evaluating the immunoreactivity of the modified polypeptide. For polypeptides useful for the generation of diagnostic binding agents, a variant may be identified by evaluating a modified polypeptide for the ability to generate antibodies that detect the presence or absence of tuberculosis. Alternatively, variants of the claimed antigens that may be usefully employed in the inventive diagnostic methods may be identified by evaluating modified polypeptides for their ability to detect antibodies present in the sera of tuberculosis-infected patients. Such modified sequences may be prepared and tested using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the immunogenic properties, secondary structure and hydropathic nature of the polypeptide. For example, a polypeptide may be conjugated to a signal (or leader) sequence at the N-tenninal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In general, *M. tuberculosis* antigens, and DNA sequences encoding such antigens, may be prepared using any of a variety of procedures. For example, genomic or cDNA libraries derived from *M. tuberculosis* may be screened directly using peripheral blood mononuclear cells (PBMCs) or T cell lines or clones derived from one or more *M. tuberculosis*-immune individuals. Direct library screens may generally be performed by assaying pools of expressed recombinant proteins for the ability of induce proliferation and/or interferon-γ production in T cells derived from an *M. tuberculosis*-immune individual. Potential T cell antigens may be first selected based on antibody reactivity, as described above.

Alternatively, DNA sequences encoding antigens may be identified by screening an appropriate *M. tuberculosis* genomic or cDNA expression library with sera obtained from patients infected with *M. tuberculosis.* Such screens may generally be performed using techniques well known to those of ordinary skill in the art, such as those described in Sambrook et al., *Molecular Cloning: A Laboratory Manual,* Cold Spring Harbor Laboratories, Cold Spring Harbor, N.Y., 1989.

Purified antigens are then evaluated for their ability to elicit an appropriate immune response (e.g., cellular) using, for example, the representative methods described herein. Immunogenic antigens may then be partially sequenced using techniques such as traditional Edman chemistry. See Edman and Berg, *Eur. J. Biochem.* 80:116–132, 1967. Immunogenic antigens may also be produced recombinantly using a DNA sequence that encodes the antigen, which has been inserted into an expression vector and expressed in an appropriate host.

DNA sequences encoding the inventive antigens may also be obtained by screening an appropriate *M. tuberculosis* cDNA or genomic DNA library for DNA sequences that hybridize to degenerate oligonucleotides derived from partial amino acid sequences of isolated antigens. Degenerate oligonucleotide sequences for use in such a screen may be designed and synthesized, and the screen may be performed, as described (for example) in Sambrook et al., *Molecular Cloning: A Laboratory Manual,* Cold Spring Harbor Laboratories, Cold Spring Harbor, N.Y., 1989 (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Regardless of the method of preparation, the antigens (and immunogenic portions thereof) described herein have the ability to induce an immunogenic response. More specifically, the antigens have the ability to induce proliferation and/or cytokine production (i.e., interferon-γ and/or interleukin-12 production) in T cells, NK cells, B cells and/or macrophages derived from an *M. tuberculosis*-immune individual. The selection of cell type for use in evaluating an immunogenic response to a antigen will, of course, depend on the desired response. For example, interleukin-12 production is most readily evaluated using preparations containing B cells and/or macrophages. An *M. tuberculosis*-immune individual is one who is considered to be resistant to the development of tuberculosis by virtue of having mounted an effective T cell response to *M. tuberculosis* (i.e., substantially free of disease symptoms). Such individuals may be identified based on a strongly positive (i.e., greater than about 10 mm diameter induration) intradermal skin test response to tuberculosis proteins (PPD) and an absence of any signs or symptoms of tuberculosis disease. T cells, NK cells, B cells and macrophages derived from *M. tuberculosis*-immune individuals may be prepared using methods known to those of ordinary skill in the art. For example, a preparation of PBMCs (i.e., peripheral blood mononuclear cells) may be employed without further separation of component cells. PBMCs may generally be prepared, for example, using density centrifugation through Ficoll™ (Winthrop Laboratories, NY).

T cells for use in the assays described herein may also be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from *M. tuberculosis*-immune individuals with mycobacterial proteins for a period of 2–4 weeks. This allows expansion of only the mycobacterial protein-specific T cells, resulting in a line composed solely of such cells. These cells may then be cloned and tested with individual proteins, using methods known to those of ordinary skill in the art, to more accurately define individual T cell specificity. In general, antigens that test positive in assays for proliferation and/or cytokine production (i.e., interferon-γ and/or interleukin-12 production) performed using T cells, NK cells, B cells and/or macrophages derived from an *M. tuberculosis*-immune individual are considered immunogenic. Such assays may be performed, for example, using the representative procedures described below. Immunogenic portions of such antigens may be identified using similar assays, and may be present within the polypeptides described herein.

The ability of a polypeptide (e.g., an immunogenic antigen, or a portion or other variant thereof) to induce cell proliferation is evaluated by contacting the cells (e.g., T cells and/or NK cells) with the polypeptide and measuring the proliferation of the cells. In general, the amount of polypeptide that is sufficient for evaluation of about $10^5$ cells ranges from about 10 ng/mL to about 100 μg/mL and preferably is about 10 μg/mL. The incubation of polypeptide with cells is typically performed at 37° C. for about six days. Following incubation with polypeptide, the cells are assayed for a proliferative response, which may be evaluated by methods known to those of ordinary skill in the art, such as exposing cells to a pulse of radiolabeled thymidine and measuring the incorporation of label into cellular DNA. In general, a polypeptide that results in at least a three fold increase in proliferation above background (i.e., the proliferation observed for cells cultured without polypeptide) is considered to be able to induce proliferation.

The ability of a polypeptide to stimulate the production of interferon-γ and/or interleukin-12 in cells may be evaluated by contacting the cells with the polypeptide and measuring the level of interferon-γ or interleukin-12 produced by the cells. In general, the amount of polypeptide that is sufficient for the evaluation of about $10^5$ cells ranges from about 10 ng/mL to about 100 μg/mL and preferably is about 10 μg/mL. The polypeptide may, but need not, be immobilized on a solid support, such as a bead or a biodegradable microsphere, such as those described in U.S. Pat. Nos. 4,897,268 and 5,075,109. The incubation of polypeptide with the cells is typically performed at 37° C. for about six days. Following incubation with polypeptide, the cells are assayed for interferon-γ and/or interleukin-12 (or one or more subunits thereof), which may be evaluated by methods known to those of ordinary skill in the art, such as an enzyme-linked immunosorbent assay (ELISA) or, in the case of IL-12 P70 heterodimer, a bioassay such as an assay measuring proliferation of T cells. In general, a polypeptide that results in the production of at least 50 pg of interferon-γ per mL of cultured supernatant (containing $10^4$–$10^5$ T cells per mL) is considered able to stimulate the production of interferon-γ. A polypeptide that stimulates the production of at least 10 pg/mL of IL-12 P70 subunit, and/or at least 100 pg/mL of IL-12 P40 subunit, per $10^5$ macrophages or B cells (or per $3 \times 10^5$ PBMC) is considered able to stimulate the production of IL-12.

In general, immunogenic antigens are those antigens that stimulate proliferation and/or cytokine production (i.e., interferon-γ and/or interleukin-12 production) in T cells, NK cells, B cells and/or macrophages derived from at least about 25% of *M. tuberculosis*-immune individuals. Among these immunogenic antigens, polypeptides having superior therapeutic properties may be distinguished based on the magnitude of the responses in the above assays and based on the percentage of individuals for which a response is observed. In addition, antigens having superior therapeutic properties will not stimulate proliferation and/or cytokine production in vitro in cells derived from more than about 25% of individuals that are not *M. tuberculosis*-immune, thereby eliminating responses that are not specifically due to *M. tuberculosis*-responsive cells. Those antigens that induce a response in a high percentage of T cell, NK cell, B cell and/or macrophage preparations from *M. tuberculosis*-immune individuals (with a low incidence of responses in cell preparations from other individuals) have superior therapeutic properties.

Antigens with superior therapeutic properties may also be identified based on their ability to diminish the severity of

*M. tuberculosis* infection in experimental animals, when administered as a vaccine. Suitable vaccine preparations for use on experimental animals are described in detail below. Efficacy may be determined based on the ability of the antigen to provide at least about a 50% reduction in bacterial numbers and/or at least about a 40% decrease in mortality following experimental infection. Suitable experimental animals include mice, guinea pigs and primates.

Antigens having superior diagnostic properties may generally be identified based on the ability to elicit a response in an intradermal skin test performed on an individual with active tuberculosis, but not in a test performed on an individual who is not infected with *M. tuberculosis*. Skin tests may generally be performed as described below, with a response of at least 5 mm induration considered positive.

Immunogenic portions of the antigens described herein may be prepared and identified using well known techniques, such as those summarized in Paul, *Fundamental Immunology*, 3d ed., Raven Press, 1993, pp. 243–247 and references cited therein. Such techniques include screening polypeptide portions of the native antigen for immunogenic properties. The representative proliferation and cytokine production assays described herein may generally be employed in these screens. An immunogenic portion of a polypeptide is a portion that, within such representative assays, generates an immune response (e.g., proliferation, interferon-γ production and/or interleukin-12 production) that is substantially similar to that generated by the full length antigen. In other words, an immunogenic portion of an antigen may generate at least about 20%, and preferably about 100%, of the proliferation induced by the full length antigen in the model proliferation assay described herein. An immunogenic portion may also, or alternatively, stimulate the production of at least about 20%, and preferably about 100%, of the interferon-γ and/or interleukin-12 induced by the full length antigen in the model assay described herein.

Portions and other variants of *M. tuberculosis* antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division, Foster City, Calif., and may be operated according to the manufacturer's instructions. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner may encode naturally occurring antigens, portions of naturally occurring antigens, or other variants thereof.

In general, regardless of the method of preparation, the polypeptides disclosed herein are prepared in substantially pure form. Preferably, the polypeptides are at least about 80% pure, more preferably at least about 90% pure and most preferably at least about 99% pure. In certain preferred embodiments, described in detail below, the substantially pure polypeptides are incorporated into pharmaceutical compositions or vaccines for use in one or more of the methods disclosed herein.

In one embodiment, the subject invention discloses polypeptides comprising at least an immunogenic portion of an *M. tuberculosis* antigen (or a variant of such an antigen) that comprises one or more of the amino acid sequences encoded by (a) the DNA sequences of SEQ ID NO: 1–12, 83, 102–108, 125, 127–137, 139 and 140; (b) the complements of such DNA sequences, or (c) DNA sequences substantially homologous to a sequence of (a) or (b). In a related embodiment, the present invention provides polypeptides comprising at least an immunogenic portion of an *M. tuberculosis* antigen having an amino acid sequence selected from the group consisting of sequences provided in SEQ ID NO: 16–33, 109, 126, 138, 141, 142 and variants thereof.

The *M. tuberculosis* antigens provided herein include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the case of cross-species homology at 45° C., 0.5×SSC; followed by washing twice at 65° C. for 20 minutes with each of 2×, 0.5× and 0.2×SSC containing 0.1% SDS). Such hybridizing DNA sequences are also within the scope of this invention, as are nucleotide sequences that, due to code degeneracy, encode an immunogenic polypeptide that is encoded by a hybridizing DNA sequence.

In a related aspect, the present invention provides fusion proteins comprising a first and a second inventive polypeptide or, alternatively, a polypeptide of the present invention and a known *M. tuberculosis* antigen, such as the 38 kD antigen described in Andersen and Hansen, *Infect. Immun.* 57:2481–2488, 1989, (Genbank Accession No. M30046), or ESAT-6 previously identified in *M. bovis* (Accession No. U34848) and in *M. tuberculosis* (Sorensen et al., *Infec. Immun.* 63:1710–1717, 1995). Variants of such fusion proteins are also provided. The fusion proteins of the present invention may include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad Sci. USA* 83:8258–8262, 1986; U.S. Pat. Nos. 4,935,233 and 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

In another aspect, the present invention provides methods for using one or more of the above polypeptides or fusion proteins (or DNA molecules encoding such polypeptides) to induce protective immunity against tuberculosis in a patient. As used herein, a "patient" refers to any warm-blooded animal, preferably a human. A patient may be afflicted with a disease, or may be free of detectable disease and/or infection. In other words, protective immunity may be induced to prevent or treat tuberculosis.

In this aspect, the polypeptide, fusion protein or DNA molecule is generally present within a pharmaceutical composition and/or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response enhancer, such as an adjuvant or a liposome (into which the polypeptide is incorporated). Such pharmaceutical compositions and vaccines may also contain other *M. tuberculosis* antigens, either incorporated into a combination polypeptide or present within a separate polypeptide.

Alternatively, a vaccine may contain DNA encoding one or more polypeptides as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In a related aspect, a DNA vaccine as described above may be administered simultaneously with or sequentially to either a polypeptide of the present invention or a known *M. tuberculosis* antigen, such as the 38 kD antigen described above. For example, administration of DNA encoding a polypeptide of the present invention, either "naked" or in a delivery system as described above, may be followed by administration of an antigen in order to enhance the protective immune effect of the vaccine.

Routes and frequency of administration, as well as dosage, will vary from individual to individual and may parallel those currently being employed in immunization using BCG. In general, the pharmaceutical compositions and vaccines may be administered by injection (e.g., intracutaneous, intramuscular, intravenous or subcutaneous), intranasally (e.g, by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from *M. tuberculosis* infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, lipids, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A and quil A.

In another aspect, this invention provides methods for using one or more of the polypeptides described above to diagnose tuberculosis using a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 48–72 hours.

The DTH reaction is a cell-mediated immune response, which is greater in patients that have been exposed previously to the test antigen (i.e., the immunogenic portion of the polypeptide employed, or a variant thereof). The response may be measured visually, using a ruler. In general, a response that is greater than about 0.5 cm in diameter, preferably greater than about 1.0 cm in diameter, is a positive response, indicative of tuberculosis infection, which may or may not be manifested as an active disease.

The polypeptides of this invention are preferably formulated, for use in a skin test, as pharmaceutical compositions containing a polypeptide and a physiologically acceptable carrier, as described above. Such compositions typically contain one or more of the above polypeptides in an amount ranging from about 1 µg to about 100 µg, preferably from about 10 µg to about 50 µg in a volume of 0.1 mL. Preferably, the carrier employed in such pharmaceutical compositions is a saline solution with appropriate preservatives, such as phenol and/or TWEEN 80™.

In a preferred embodiment, a polypeptide employed in a skin test is of sufficient size such that it remains at the site of injection for the duration of the reaction period. In general, a polypeptide that is at least 9 amino acids in length is sufficient. The polypeptide is also preferably broken down by macrophages within hours of injection to allow presentation to T-cells. Such polypeptides may contain repeats of one or more of the above sequences and/or other immunogenic or non-immunogenic sequences.

The following Examples are offered by way of illustration and not by way of limitation.

EXAMPLE 1

Purification and Characterization of *M. Tuberculosis* Polypeptide Using CD4+ T Cell Lines Generated from Human PBMC

*M. tuberculosis* antigens of the present invention were isolated by expression cloning of cDNA libraries of *M. tuberculosis* strains H37Rv and Erdman essentially as described by Sanderson et al. (*J. Exp. Med.,* 1995, 182:1751–1757) and were shown to induce PBMC proliferation and IFN-γ in an immunoreactive T cell line.

Two CD4+ T cell lines, referred to as DC-4 and DC-5, were generated against dendritic cells infected with *M. tuberculosis*. Specifically, dendritic cells were prepared from adherent PBMC from a single donor and subsequently infected with tuberculosis. Lymphocytes from the same donor were cultured under limiting dilution conditions with the infected dendritic cells to generate the CD4+ T cell lines DC-4 and DC-5. These cell lines were shown to react with crude soluble proteins from *M. tuberculosis* but not with Tb38-1. Limiting dilution conditions were employed to obtain a third CD4+ T cell line, referred to as DC-6, which was shown to react with both crude soluble proteins and Tb38-1.

Genomic DNA was isolated from the *M. tuberculosis* strains H37Rv and Erdman and used to construct expression libraries in the vector pBSK(−) using the Lambda ZAP expression system (Stratagene, La Jolla, Calif.). These libraries were transformed into *E. coli,* pools of induced *E. coli* cultures were incubated with dendritic cells, and the ability of the resulting incubated dendritic cells to stimulate cell proliferation and IFN-γ production in the CD4+ T cell line DC-6 was examined as described below in Example 2. Positive pools were fractionated and re-tested until pure *M. tuberculosis* clones were obtained. Nineteen clones were isolated, of which nine were found to contain the previously identified *M. tuberculosis* antigens TbH-9 and Tb38-1, disclosed in U.S. patent application Ser. No. 08/533,634. The determined cDNA sequences for the remaining ten clones (hereinafter referred to as Tb224, Tb636, Tb424, Tb436, Tb398, Tb508, Tb441, Tb475, Tb488 and Tb465) are provided in SEQ ID No: 1–10, respectively. The corresponding predicted amino acid sequences for Tb224 and Tb636 are provided in SEQ ID NO: 13 and 14, respectively. The open reading frames for these two antigens were found to show some homology to TbH-9, described above. Tb224 and Tb636 were also found to be overlapping clones.

Tb424, Tb436, Tb398, Tb508, Tb441, Tb475, Tb488 and Tb465 were each found to contain two small open reading frames (referred to as ORF-1 and ORF-2) or truncated forms thereof, with minor variations in ORF-1 and ORF-2 being found for each clone. The predicted amino acid sequences of ORF-1 and ORF-2 for Tb424, Th436, Tb398, Tb508, Tb441, Tb475, Tb488 and Tb465 are provided in SEQ ID NO: 16 and 17, 18 and 19, 20 and 21, 22 and 23, 24 and 25, 26 and 27, 28 and 29, and 30 and 31, respectively. In addition, clones Tb424 and Tb436 were found to contain a third apparent open reading frame, referred to as ORF-U. The predicted amino acid sequences of ORF-U for Tb424 and Tb436 are provided in SEQ ID NO: 32 and 33, respectively. Tb424 and Tb436 were found to be either overlapping clones or recently duplicated/transposed copies. Similarly Tb398, Tb508 and Tb465 were found to be either overlapping clones or recently duplicated/transposed copies, as were Tb475 and Tb488.

These sequences were compared with known sequences in the gene bank using the BLASTN system. No homologies to the antigens Tb224 and Tb431 were found. Tb636 was found to be 100% identical to a cosmid previously identified in *M. tuberculosis.* Similarly, Tb508, Tb488, Tb398, Tb424, Tb436, Tb441, Tb465 and Tb475 were found to show homology to known *M. tuberculosis* cosmids. In addition, Tb488 was found to have 100% homology to *M. tuberculosis* topoisomerase I.

Seventeen overlapping peptides to the open reading frame ORF-1 (referred to as 1-1–1-17; SEQ ID NO: 34–50, respectively) and thirty overlapping peptides to the open reading frame ORF-2 (referred to as 2-1–2-30, SEQ ID NO:

51–80) were synthesized using the procedure described below in Example 3.

Figure 1B:
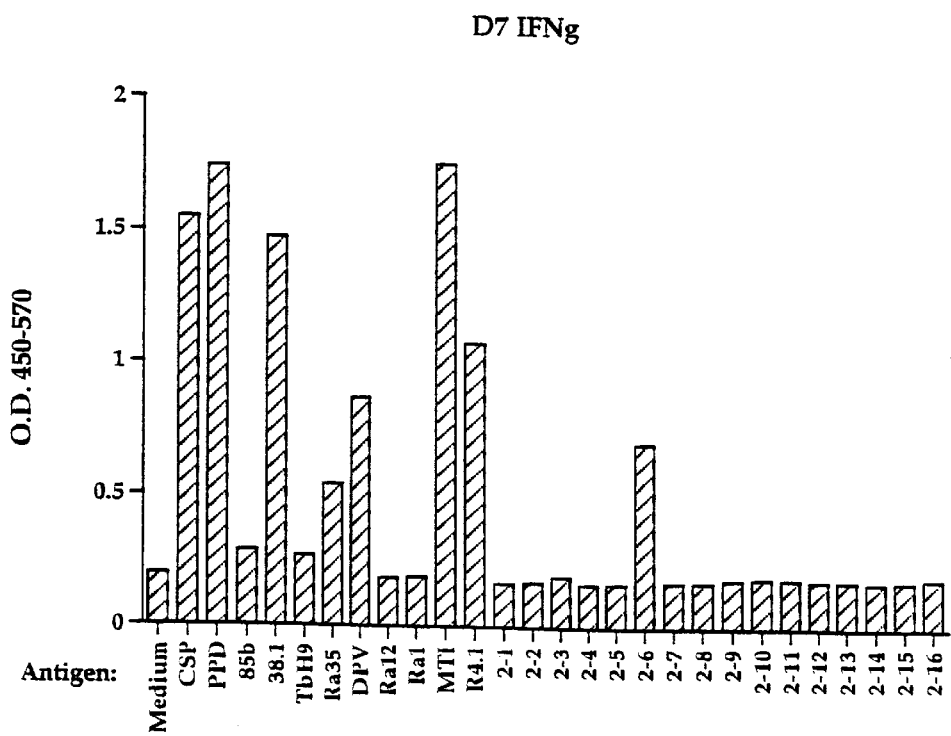
Figure 2A:
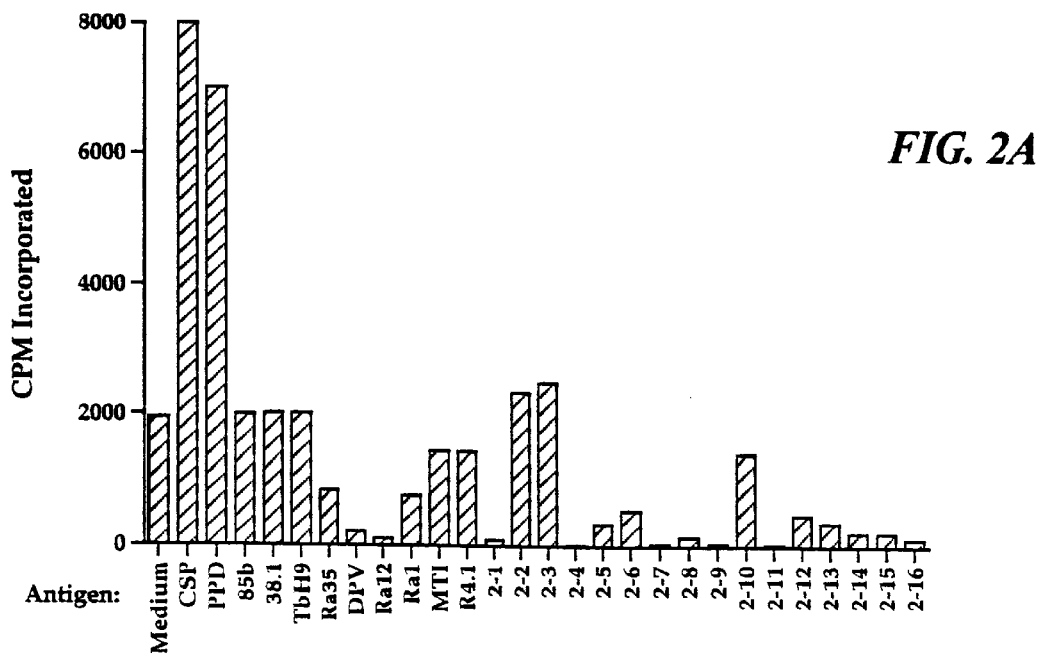
Figure 2B:
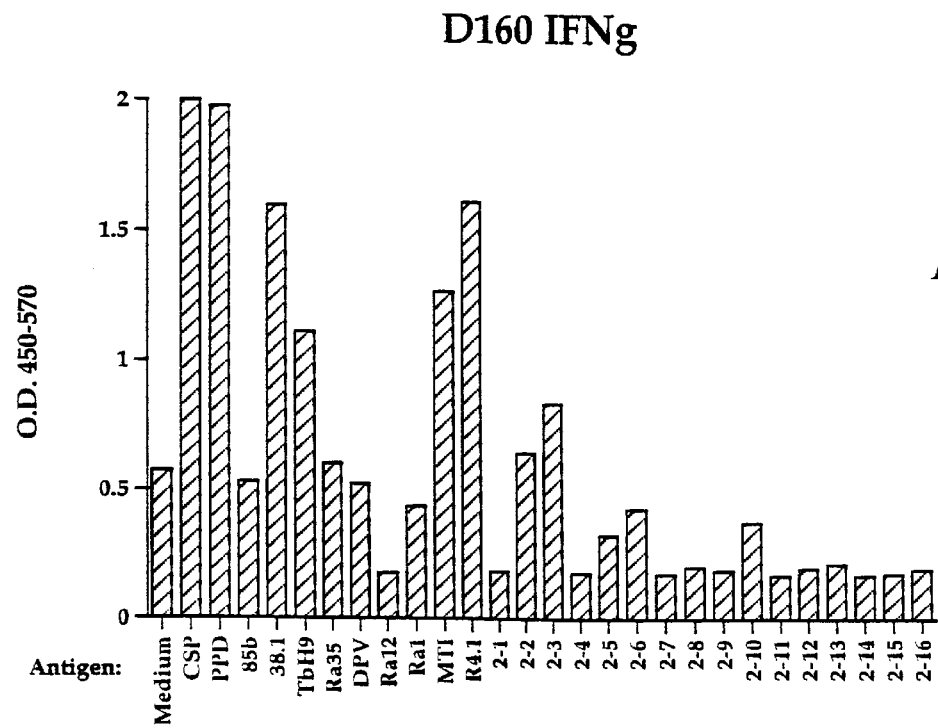

The ability of the synthetic peptides, and of recombinant ORF-1 and ORF-2, to induce T cell proliferation and IFN-γ production in PBMC from PPD-positive donors was assayed as described below in Example 2. FIGS. 1A–B and 2A–B illustrate stimulation of T cell proliferation and IFN-γ by recombinant ORF-2 and the synthetic peptides 2-1–2-16 for two donors, referred to as D7 and D160, respectively. Recombinant ORF-2 (referred to as MTI) stimulated T cell proliferation and IFN-γ production in PBMC from both donors. The amount of PBMC stimulation seen with the individual synthetic peptides varied with each donor, indicating that each donor recognizes different epitopes on ORF-2. The proteins encoded by ORF-1, ORF-2 and ORF-U were subsequently named MTS, MTI and MSF, respectively.

Eighteen overlapping peptides to the sequence of MSF (referred to as MSF-1–MSF-18; SEQ ID NO: 84–101, respectively) were synthesized and their ability to stimulate T cell proliferation and IFN-γ production in a CD4+ T cell line generated against *M. tuberculosis* culture filtrate was examined as described below. The peptides referred to as MSF-12 and MSF-13 (SEQ ID NO: 95 and 96, respectively) were found to show the highest levels of reactivity. Two overlapping peptides (SEQ ID NO:81 and 82) to the open reading frame of Tb224 were synthesized and shown to induce T cell proliferation and IFN-γ production in PBMC from PPD-positive donors.

Two CD4+ T cell lines from different donors were generated against *M. tuberculosis* infected dendritic cells using the above methodology. Screening of the *M. tuberculosis* cDNA expression library described above using this cell line, resulted in the isolation of two clones referred to as Tb867 and Tb391. The determined cDNA sequence for Tb867 (SEQ ID NO: 102) was found to be identical to the previously isolated *M. tuberculosis* cosmid SCY22G10, with the candidate reactive open reading frame encoding a 750 amino acid *M. tuberculosis* protein kinase. Comparison of the determined cDNA sequence for Tb391 (SEQ ID NO: 103) with those in the gene bank revealed no significant homologies to known sequences.

In further studies, CD4+ T cell lines were generated against *M. tuberculosis* culture filtrate, essentially as outlined above, and used to screen the *M. tuberculosis* Erdman cDNA expression library described above. Five reactive clones, referred to as Tb431, Tb472, Tb470, Tb838 and Tb962 were isolated. The determined cDNA sequences for Tb431, Tb472, Tb470, and Tb838 are provided in SEQ ID NO: 11, 12, 104 and 105, respectively, with the determined cDNA sequences for Tb962 being provided in SEQ ID NO: 106 and 107. The corresponding predicted amino acid sequence for Tb431 is provided in SEQ ID NO: 15.

Subsequent studies led to the isolation of a full-length cDNA sequence for Tb472 (SEQ ID NO: 108). Overlapping peptides were synthesized and used to identify the reactive open reading frame. The predicted amino acid sequence for the protein encoded by Tb472 (referred to as MSL) is provided in SEQ ID NO: 109. Comparison of the sequences for Tb472 and MSL with those in the gene bank, as described above, revealed no homologies to known sequences. Fifteen overlapping peptides to the sequence of MSL (referred to as MSL-1–MSL-15; SEQ ID NO: 110–124, respectively) were synthesized and their ability to stimulate T cell proliferation and IFN-γ production in a CD4+ Tcell line generated against *M. tuberculosis* culture filtrate was examined as described below. The peptides referred to as MSL-10 (SEQ ID NO: 119) and MSL-11 (SEQ ID NO: 120) were found to show the highest level of reactivity.

Comparison of the determined cDNA sequence for Tb838 with those in the gene bank revealed identity to the previously isolated *M. tuberculosis* cosmid SCY07H7. Comparison of the determined cDNA sequences for the clone Tb962 with those in the gene bank revealed some homology to two previously identified *M. tuberculosis* cosmids, one encoding a portion of bactoferritin. However, recombinant bactoferritin was not found to be reactive with the T cell line used to isolate Tb962.

The clone Tb470, described above, was used to recover a full-length open reading (SEQ ID NO: 125) that showed homology with TbH9 and was found to encode a 40 kDa antigen, referred to as Mtb40. The determined amino acid sequence for Mtb40 is provided in SEQ ID NO: 126. Similarly, Subsequent Studies LED to the Isolation of the Full-Length cDNA Sequence for TB43 1, Provided in SEQ ID NO: 83, which was determined to contain an open reading frame encoding Mtb40. Tb470 and Tb431 were also found to contain a potential open reading frame encoding a U-ORF-like antigen.

Screening of an *M. tuberculosis* Erdman cDNA expression library with multiple CD4+ Tcell lines generated against *M. tuberculosis* culture filtrate, resulted in the isolation of three clones, referred to as Tb366, Tb433 and Tb439. The determined EDNA sequences for Tb366, Tb433 and Tb439 are provided in SEQ ID NO: 127, 128 and 129, respectively. Comparison of these sequences with those in the gene bank revealed no significant homologies to Tb366. Tb433 was found to show some 30 homology to the previously identified *M. tuberculosis* antigen MPT83. Tb439 was found to show 100% identity to the previously isolated *M. tuberculosis* cosmid SCY02B10.

A CD4+ T cell line was generated against *M. tuberculosis* PPD, essentially described above, and used to screen the above *M. tuberculosis* Erdman cDNA expression library. One reactive clone (referred to as Tb372) was isolated, with the determined cDNA sequences being provided in SEQ ID NO: 130 and 131. Comparison of these sequences with those in the gene bank revealed no significant homologies.

In further studies, screening of an *M. tuberculosis* cDNA expression library with a CD4+ T cell line generated against dendritic cells that had been infected with tuberculosis for 8 days, as described above, led to the isolation of two clones referred to as Tb390R5C6 and Tb390R2C11. The determined cDNA sequence for Tb390R5C6 is provided in SEQ ID NO: 132, with the determined cDNA sequences for Tb390R2C11 being provided in SEQ ID NO: 133 and 134. Tb390R5C6 was found to show 100% identity to a previously identified *M. tuberculosis* cosmid.

In subsequent studies, the methodology described above was used to screen an *M. tuberculosis* genomic DNA library prepared as follows. Genomic DNA from *M. tuberculosis* Erdman strain was randomly sheared to an average size of 2 kb, and blunt ended with Klenow polymerase, followed by the addition of EcoRI adaptors. The insert was subsequently ligated into the Screen phage vector (Novagen, Madison, Wis.) and packaged in vitro using the PhageMaker extract (Novagen). The phage library (referred to as the Erd λScreen library) was amplified and a portion was converted into a plasmid expression library by an autosubcloning mechanism using the *E. coli* strain BM25.8 (Novagen). Plasmid DNA was purified from BM25.8 cultures containing the pSCREEN recombinants and used to transform competent cells of the expressing host strain BL21 (DE3)pLysS. Transformed cells were aliquoted into 96 well microtiter plates with each well containing a pool size of approximately 50 colonies. Replica plates of the 96 well plasmid library format were induced with IPTG to allow recombinant protein expression. Following induction, the plates were centrifuged to pellet the *E. coli* which was used directly in T cell expression cloning of a CD4+ T cell line prepared from a PPD-positive donor (donor 160) as described above. Pools containing *E. coli* expressing *M. tuberculosis* T cell antigens were subsequently broken down into individual colonies and reassayed in a similar fashion to identify positive hits.

Screening of the T cell line from donor 160 with one 96 well plate of the Erd λScreen library provided a total of nine positive hits. Previous experiments on the screening of the pBSK library described above with T cells from donor 160 suggested that most or all of the positive clones would be TbH-9, Tb38-1 or MTI (disclosed in U.S. patent application Ser. No. 08/533,634) or variants thereof. However, Southern analysis revealed that only three wells hybridized with a mixed probe of TbH-9, Tb38-1 and MTI. Of the remaining six positive wells, two were found to be identical. The determined 5' cDNA sequences for two of the isolated clones (referred to as Y1-26C1 and Y1-86C11) are provided in SEQ ID NO: 135 and 136, respectively. The full length cDNA sequence for the isolated clone referred to as hTcc#1 is provided in SEQ ID NO: 137, with the corresponding predicted amino acid sequence being provided in SEQ ID NO: 138. Comparison of the sequences of hTcc#1 to those in the gene bank as described above, revealed some homology to the previously isolated *M. tuberculosis* cosmid MTCY07H7B.06.

EXAMPLE 2

Induction of T Cell Proliferation and Interferon-γ Production by *M. Tuberculosis* Antigens The ability of recombinant *M. tuberculosis* antigens to induce T cell proliferation and interferon-γ production may be determined as follows.

Proteins may be induced by IPTG and purified by gel elution, as described in Skeiky et al. *J. Exp. Med.,* 1995, 181:1527–1537. The purified polypeptides are then screened for the ability to induce T-cell proliferation in PBMC preparations. The PBMCs from donors known to be PPD skin test positive and whose T-cells are known to proliferate in response to PPD, are cultured in medium comprising RPMI 1640 supplemented with 10% pooled human serum and 50 μg/ml gentamicin. Purified polypeptides are added in duplicate at concentrations of 0.5 to 10 μg/mL. After six days of culture in 96-well round-bottom plates in a volume of 200 μl, 50 μl of medium is removed from each well for determination of IFN-γ levels, as described below. The plates are then pulsed with 1 μCi/well of tritiated thymidine for a further 18 hours, harvested and tritium uptake determined using a gas scintillation counter. Fractions that result in proliferation in both replicates three fold greater than the proliferation observed in cells cultured in medium alone are considered positive.

IFN-γ is measured using an enzyme-linked immunosorbent assay (ELISA). ELISA plates are coated with a mouse monoclonal antibody directed to human IFN-γ (PharMingen, San Diego, Calif.) in PBS for four hours at room temperature. Wells are then blocked with PBS containing 5% (W/V) non-fat dried milk for 1 hour at room temperature. The plates are washed six times in PBS/0.2% TWEEN20™ and samples diluted 1:2 in culture medium in the ELISA plates are incubated overnight at room temperature. The plates are again washed and a polyclonal rabbit anti-human IFN-γ serum diluted 1:3000 in PBS/10% normal goat serum is added to each well. The plates are then incubated for two hours at room temperature, washed and horseradish peroxidase-coupled anti-rabbit IgG (Sigma Chemical So., St. Louis, Mo.) is added at a 1:2000 dilution in PBS/5% non-fat dried milk. After a further two hour incubation at room temperature, the plates are washed and TMB substrate added. The reaction is stopped after 20 min with 1 N sulfuric acid. Optical density is determined at 450 nm using 570 nm as a reference wavelength. Fractions that result in both replicates giving an OD two fold greater than the mean OD from cells cultured in medium alone, plus 3 standard deviations, are considered positive.

EXAMPLE 3

Purification and Characterization of *M. Tuberculosis* Polypeptides using CD4+ T Cell Lines Generated from a Mouse *M. Tuberculosis* Model Infection of C57BL/6 mice with *M. tuberculosis* results in the development of a progressive disease for approximately 2–3 weeks. The disease progression is then halted as a consequence of the emergence of a strong protective T cell-mediated immune response. This infection model was used to generate T cell lines capable of recognizing protective *M. tuberculosis* antigens.

Specifically, spleen cells were obtained from C57BL/6 mice infected with *M. tuberculosis* for 28 days and used to raise specific anti-*M. tuberculosis* T cell lines as described above. The resulting CD4+ T cell lines, in conjunction with normal antigen presenting (spleen) cells from C57BL/6 mice were used to screen the *M. tuberculosis* Erd λscreen library described above. One of the reactive library pools, which was found to be highly stimulatory of the T cells, was selected and the corresponding active clone (referred to as Y288C10) was isolated.

Sequencing of the clone Y288C10 revealed that it contains two potential genes, in tandem. The determined cDNA sequences for these two genes (referred to as mTCC#1 and mTCC#2) are provided in SEQ ID NO: 139 and 140, respectively, with the corresponding predicted amino acid sequences being provided in SEQ ID NO: 141 and 142, respectively. Comparison of these sequences with those in the gene bank revealed identity to unknown sequences previously found within the *M. tuberculosis* cosmid MTY21C12. The predicted amino acid sequences of mTCC#1 and mTCC#2 were found to show some homology to previously identified members of the TbH9 protein family, discussed above.

EXAMPLE 4

Synthesis of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

From the foregoing, it will be appreciated that, although specific embodiments of the invention have been described herein for the purpose of illustration, various modifications may be made without deviating from the spirit and scope of the invention.

What is claimed is:

1. An isolated polypeptide comprising an amino acid sequence as set forth in SEQ ID NO:109.

2. The polypeptide of claim 1, which is a soluble peptide.

3. The polypeptide of claim 1, which is produced by a recombinant DNA method.

4. The polypeptide of claim 1, which is produced by a chemical synthetic method.

5. The polypeptide of claim 1, which is purified from a cell source or culture supernatant.

6. The polypeptide of claim 1, which reacts with an antibody-containing biological sample.

7. The polypeptide of claim 1, which is a *Mycobacterium tuberculosis* antigen.

8. The polypeptide of claim 1, which is fused with a second heterologous polypeptide.

9. An isolated polypeptide from *Mycobacterium tuberculosis* encoded by a polynucleotide that hybridizes under moderately stringent conditions to a second polynucleotide that is complementary to the nucleotide sequence of SEQ ID NO:108, wherein said moderately stringent conditions comprise prewashing in a solution of 5×SSC, 0.5% SDS, 1.0 mM EDTA (pH 8.0); hybridizing at 50–65° C. overnight in a solution comprising 5×SSC; and washing twice at 65° C. for 20 minutes with each of 2×, 0.5×, and 0.2×SSC containing 0.1% SDS.

10. The polypeptide of claim 9, encoded by a nucleic acid sequence comprising nucleotide sequence of SEQ ID NO:108.

11. The polypeptide of claim 9, comprising an amino acid sequence of SEQ ID NO:109.

12. A composition comprising:

(a) an isolated polypeptide of claim 9, and (b) a physiological acceptable carrier.

13. The composition of claim 9, further comprising an adjuvant.

* * * * *

```
                           SEQUENCE LISTING (1) GENERAL INFORMATION:

(iii) NUMBER OF SEQUENCES: 144

(2) INFORMATION FOR SEQ ID NO:1:

(i) SEQUENCE CHARACTERISTICS:
         (A) LENGTH: 1886 base pairs
         (B) TYPE: nucleic acid
         (C) STRANDEDNESS: double
         (D) TOPOLOGY: linear (ii) MOLECULE TYPE: DNA (genomic)

(vi) ORIGINAL SOURCE:
         (A) ORGANISM: Mycobacterium tuberculosis (xi) SEQUENCE DESCRIPTION: SEQ ID NO:1:

CGCTCTGGTG ACCACCAACT TCTTCGGTGT CAACACCATC CCGATCGCCC TCAACGAGGC      60

CGACTACCTG CGCATGTGGA TCCAGGCCGC CACCGTCATG AGCCACTATC AAGCCGTCGC     120

GCACGAAATC TGGTGTCTCC ATGAATANGC CAGTTCGGGA AAGCCGTGGG CCAGTATCAC     180

CACGGGTGCG CCGGGCTCAC CGGCCTCGAC CACTCGCAGT CGCACGCCGT TGGTATCAAC     240

TAACCGTNCN GTANGTGCGC CCATCGTCTC ACCAAATCAC ACCGGGCACC GGCCTGAGAA     300

GGGCTTGGGG AGCANCCAGA GGCGATTGTC GCGGGTGCTG CCGCGCATCA TTGATCGGCC     360

GGCCGGACCA NTCGGGCCTC CCTTGACGTC CGGATCNCAC TTCCTGTGCA GCTGGCATGG     420

CTACAGCTCA CAGTGACTGC CCCACGATTG CCGGCCAGGT CCAGTTCAAA TTCCGGTGAA     480

TTCGCGGACA AAAGCAGCAG GTCAACCAAC CGCAGTCAGT CGAGGGTCCC AAACGTGAGC     540

CAATCGGTGA AATGGCTTGC TGCAGTGACA CCGGTCACAG GCTTAGCCGA CAGCACCGGA     600

ATAGCTCAGG CGGGCTATAG AGTCCTATAG AAACATTTGC TGATAGAATT AACCGCTGTC     660

TTGGCGTGAT CTTGATACGG CTCGCCGTGC GACCGGTTGG CTCAGTAGCT GACCACCATG     720

TAACCCATCC TCGGCAGGTG TCTACTAAGG CGAGACACCG CATTGGTGGG GCTGCATCGC     780

AAATCGGTCC GAGCATGTAG CACTGCCGTT ATCCCGGGAT AGCAAACCAC CCGGAACCAG     840

GGCTATCCCA GTCGCTCTCC GACGGAGGCC GTTTCGCTTT CCGTTGCCCG ATAACTCCCG     900

AGTGGATATC GGCGTTATCA NATTCAGGCT TTTCTTCGCA AGGTACCGGT GTTCGCTATA     960

TTCGGATATC TCGGACGGAT AATTACTAAA ACTTCAGTGG TTTAGATAAG GCCGCCGCAA    1020

TACTTCGCCG ATCTTGCCGA GCGCAACGGA TTTCCATCGT CGGTTTTCGT CGCCTTATCA    1080

AACATGATCG GAGATAATGA CAGATCGGCC TAGCTAGGTG TTTAGCGGAC GCGATTTAGG    1140

ACAACCGAGA TTTGCTTTGC CTCGCAACCA TGAGAGCGCC CCGCTTCGAC GCCGAATCGG    1200

GTGAGTGATG GTGGGTTAGC ACAGCCCTGA TTGCGCCACC GGCGAGGTGA TTGTGCCCGC    1260

CACGAGGCCG CCGCCGGCTA GCCCCATGAG CACGNTATAT AGACTCTCCT GCAACAGATC    1320

TCATACCGAT CGAAGGCGAA GCGCAGGCAT CGACGTCGGA GACACTGCCT TGGGATCGCG    1380

CCGCCTACAC GGCGGTTGGC GCATTGTCGC AGCGCAGTTG CAGGAGGGCA AATGTGCGCA    1440

GACGATGTAG TCGACAACAA GTGNACATGC CGTCTTCACG AACTCAAAAC TGACGATCTG    1500
```

```
CTTAGCATGA AAAAAACTGT TGACATCGGC CAAGCATGAC AGCCAGACTG TAGGCCTACG    1560

CGTGCAATGC AGAACCAAGG NTATGCATGG AATCGACGAC CGTTGAGATA GGCGGCAGGC    1620

ATGAGCAGAG CGTTCATCAT CGATCCAACG ATCAGTGCCA TTGACGGCTT GTACGACCTT    1680

CTGGGGATTG GAATACCCAA CCAAGGGGGT ATCCTTTACT CCTCACTAGA GTACTTCGAA    1740

AAAGCCCTGG AGGAGCTGGC AGCAGCGTTT CCGGGTGATG GCTGGTTAGG TTCGGCCGCG    1800

GACAAATACG CCGGCAAAAA CCGCAACCAC GTGAATTTTT TCCAGGAACT GGCAGACCTC    1860

GATCGTCAGC TCATCAGCCT GATCCA                                         1886
```

(2) INFORMATION FOR SEQ ID NO:2:

(i) SEQUENCE CHARACTERISTICS:
        (A) LENGTH: 2305 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:2:

```
GGCACGCGCT GGCCGCGCAA TACACCGAAA TTGCAACGGA ACTCGCAAGC GTGCTCGCTG      60

CGGTGCAGGC AAGCTCGTGG CAGGGGCCCA GCGCCGACCG GTTCGTCGTC GCCCATCAAC     120

CGTTCCGGTA TTGGCTAACC CACGCTGCCA CGGTGGCCAC CGCAGCAGCC GCCGCGCACN     180

AAACGGCCGC CGCCGGGTAT ACGTCCGCAT TGGGGGCAT GCCTACGCTA GCCGAGTTGG      240

CGGCCAACCA TGCCATGCAC GGCGCTCTGG TGACCACCAA CTTCTTCGGT GTCAACACCA     300

TCCCGATCGC CCTCAACGAG GCCGACTACC TGCGCATGTG GATCCAGGCC GCCACCGTCA     360

TGAGCCACTA TCAAGCCGTC GCGCACGAAA GCGTGGCGGC GACCCCCAGC ACGCCGCCGG     420

CGCCGCAGAT AGTGACCAGT GCGGCCAGCT CGGCGGCTAG CAGCAGCTTC CCCGACCCGA     480

CCAAATTGAT CCTGCAGCTA CTCAAGGATT TCCTGGAGCT GCTGCGCTAT CTGGCTGTTG     540

AGCTGCTGCC GGGGCCGCTC GGCGACCTCA TCGCCCAGGT GTTGGACTGG TTCATCTCGT     600

TCGTGTCCGG TCCAGTCTTC ACGTTTCTCG CCTACCTGGT GCTGGACCCA CTGATCTATT     660

TCGGACCGTT CGCCCCGCTG ACGAGTCCGG TCCTGTTGCC TGCTGTGGAG TTACGCAACC     720

GCCTCAAAAC CGCCACCGGA CTGACGCTGC CACCTACCGT GATTTTCGAT CATCCCACTC     780

CCACTGCGGT CGCCGAGTAT GTCGCCCAGC AAATGTCTGG CAGCCGCCCA ACGGAATCCG     840

GTGATCCGAC GTCGCAGGTT GTCGAACCCG CTCGTGCCGA ATTCGGCACG AGTGCTGTTC     900

ATCAAATCCC CCCGAGACCT GCGGACACCC GGCGCGCTTG CCGACATCGA GATGATGTCC     960

CGCGAGATAG CAGAATTGCC CAACATCGTG ATGGTGCGGG GCTTGACCCG ACCGAACGGG    1020

GAACCTCTGA AGGAGACCAA GGTCTCGTTT CAGGCTGGTG AAGTGGGCGG CAAGCTCGAC    1080

GAAGCGACCA CCCTGCTCGA AGAGCACGGA GGCGAGCTGG ACCAGCTGAC CGGCGGTGCG    1140

CACCAGTTGG CCGACGCCCT CGCCCAAATA CGCAACGAAA TCAATGGGGC CGTGGCCAGC    1200

TCGAGCGGGA TAGTCAACAC CCTGCAGGCC ATGATGGACC TGATGGGCGG TGACAAGACC    1260

ATCCGACAAC TGGAAAATGC GTCCCAATAT GTCGGGCGCA TGCGGGCTCT GGGGGACAAT    1320

CTGAGCGGGA CCGTCACCGA TGCCGAACAA ATCGCCACTT GGGCCAGCCC TATGGTCAAC    1380

GCCCTCAACT CCAGCCCGGT GTGTAACAGC GATCCCGCCT GTCGGACGTC GCGCGCACAG    1440
```

```
TTGGCGGCGA TTGTCCAGGC GCAGGACGAC GGCCTGCTCA GGTCCATCAG AGCGCTAGCC    1500

GTCACCCTGC AACAGACGCA GGAATACCAG ACACTCGCCC GGACGGTGAG CACACTGGAC    1560

GGGCAACTGA AGCAAGTCGT CAGCACCCTC AAAGCGGTCG ACGGCCTACC CACCAAATTG    1620

GCTCAAATGC AGCAAGGAGC CAACGCTCTC GCCGACGGCA GCGCAGCGCT GGCGGCAGGC    1680

GTGCAGGAAT TGGTCGATCA GGTCAAAAAG ATGGGCTCAG GGCTCAACGA GGCCGCCGAC    1740

TTCCTGTTGG GGATCAAGCG GGATGCGGAC AAGCCGTCAA TGGCGGGCTT CAACATTCCA    1800

CCGCAGATTT TTTCGAGGGA CGAGTTCAAG AAGGGCGCCC AGATTTTCCT GTCGGCCGAT    1860

GGTCATGCGG CGCGGTACTT CGTGCAGAGC GCGCTGAATC CGGCCACCAC CGAGGCGATG    1920

GATCAGGTCA ACGATATCCT CCGTGTTGCG GATTCCGCGC GACCGAATAC CGAACTCGAG    1980

GATGCCACGA TAGGTCTGGC GGGGGTTCCG ACTGCGCTGC GGGATATCCG CGACTACTAC    2040

AACAGCGATA TGAAATTCAT CGTCATTGCG ACGATCGTTA TCGTATTCTT GATTCTCGTC    2100

ATTCTGNTGC GCGCACTTGT GGNTCCGATA TATCTGATAG GCTCGGTGCT GATTTCTTAC    2160

TTGTCGGCCC TAGGCATAGG AACTTTCGTT TTCCAATTGA TACTGGGCCA GGAAATGCAT    2220

TGGAGCCTGC CGGGACTGTC CTTCATATTA TTGGTTGCCA TCGGCGCTGA CTACAACATG    2280

CTGCTCATTT CACGCATCCG CGACG                                         2305
```

(2) INFORMATION FOR SEQ ID NO:3:

(i) SEQUENCE CHARACTERISTICS:
        (A) LENGTH: 1742 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:3:

```
CCGCTCTCTT TCAACGTCAT AAGTTCGGTG GGCCAGTCGG CCGCGCGTGC ATATGGCACC      60

AATAACGCGT GTCCCATGGA TACCCGGACC GCACGACGGT AGAGCGGATC AGCGCAGCCG     120

GTGCCGAACA CTACCGCGTC CACGCTCAGC CCTGCCGCGT TGCGGAAGAT CGAGCCCAGG     180

TTCTCATGGT CGTTAACGCC TTCCAACACT GCGACGGTGC GCGCCCCGGC GACCACCTGA     240

GCAACGCTCG GCTCCGGCAC CCGGCGCGCG GCTGCCAACA CCCCACGATT GAGATGGAAG     300

CCGATCACCC GTGCCATGAC ATCAGCCGAC GCTCGATAGT ACGGCGCGCC GACACCGGCC     360

AGATCATCCT TGAGCTCGGC CAGCCGGCGG TCGGTGCCGA ACAGCGCCAG CGGCGTGAAC     420

CGTGAGGCCA GCATGCGCTG CACCACCAGC ACACCCTCGG CGATCACCAA CGCCTTGCCG     480

GTCGGCAGAT CGGGACNACN GTCGATGCTG TTCAGGTCAC GGAAATCGTC GAGCCGTGGG     540

TCGTCGGGAT CGCAGACGTC CTGAACATCG AGGCCGTCGG GGTGCTGGGC ACAACGGCCT     600

TCGGTCACGG GCTTTCGTCG ACCAGAGCCA GCATCAGATC GGCGGCGCTG CGCAGGATGT     660

CACGCTCGCT GCGGTTCAGC GTCGCGAGCC GCTCAGCCAG CCACTCTTGC AGAGAGCCGT     720

TGCTGGGATT AATTGGGAGA GGAAGACAGC ATGTCGTTCG TGACCACACA GCCGGAAGCC     780

CTGGCAGCTG CGGCGGCGAA CCTACAGGGT ATTGGCACGA CAATGAACGC CCAGAACGCG     840

GCCGCGGCTG CTCCAACCAC CGGAGTAGTG CCCGCAGCCG CCGATGAAGT ATCAGCGCTG     900

ACCGCGGCTC AGTTTGCTGC GCACGCGCAG ATGTACCAAA CGGTCAGCGC CCAGGCCGCG     960

GCCATTCACG AAATGTTCGT GAACACGCTG GTGGCCAGTT CTGGCTCATA CGCGGCCACC    1020
```

```
GAGGCGGCCA ACGCAGCCGC TGCCGGCTGA ACGGGCTCGC ACGAACCTGC TGAAGGAGAG    1080

GGGGAACATC CGGAGTTCTC GGGTCAGGGG TTGCGCCAGC GCCCAGCCGA TTCAGNTATC    1140

GGCGTCCATA ACAGCAGACG ATCTAGGCAT TCAGTACTAA GGAGACAGGC AACATGGCCT    1200

CACGTTTTAT GACGGATCCG CATGCGATGC GGGACATGGC GGGCCGTTTT GAGGTGCACG    1260

CCCAGACGGT GGAGGACGAG GCTCGCCGGA TGTGGGCGTC CGCGCAAAAC ATTTCCGGTG    1320

CGGGCTGGAG TGGCATGGCC GAGGCGACCT CGCTAGACAC CATGACCTAG ATGAATCAGG    1380

CGTTTCGCAA CATCGTGAAC ATGCTGCACG GGGTGCGTGA CGGGCTGGTT CGCGACGCCA    1440

ACAANTACGA ACAGCAAGAG CAGGCCTCCC AGCAGATCCT GAGCAGNTAG CGCCGAAAGC    1500

CACAGCTGNG TACGNTTTCT CACATTAGGA GAACACCAAT ATGACGATTA ATTACCAGTT    1560

CGGGGACGTC GACGCTCATG GCGCCATGAT CCGCGCTCAG GCGGCGTCGC TTGAGGCGGA    1620

GCATCAGGCC ATCGTTCGTG ATGTGTTGGC GCGGGTGAC TTTTGGGGCG GCGCCGGTTC    1680

GGTGGCTTGC CAGGAGTTCA TTACCCAGTT GGGCCGTAAC TTCCAGGTGA TCTACGAGCA    1740

GG                                                                 1742

(2) INFORMATION FOR SEQ ID NO:4:

(i) SEQUENCE CHARACTERISTICS:
        (A) LENGTH: 2836 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Mycobacterium tuberculosis (xi) SEQUENCE DESCRIPTION: SEQ ID NO:4:

GTTGATTCCG TTCGCGGCGC CGCCGAAGAC CACCAACTCC GCTGGGGTGG TCGCACAGGC     60

GGTTGCGTCG GTCAGCTGGC CGAATCCCAA TGATTGGTGG CTCNGTGCGG TTGCTGGGCT    120

CGATTACCCC CACGGAAAGG ACGACGATCG TTCGTTTGCT CGGTCAGTCG TACTTGGCGA    180

CGGGCATGGC GCGGTTTCTT ACCTCGATCG CACAGCAGCT GACCTTCGGC CCAGGGGGCA    240

CAACGGCTGG CTCCGGCGGA GCCTGGTACC CAACGCCACA ATTCGCCGGC CTGGGTGCAG    300

GCCCGGCGGT GTCGGCGAGT TTGGCGCGGG CGGAGCCGGT CGGGAGGTTG TCGGTGCCGC    360

CAAGTTGGGC CGTCGCGGCT CCGGCCTTCG CGGAGAAGCC TGAGGCGGGC ACGCCGATGT    420

CCGTCATCGG CGAAGCGTCC AGCTGCGGTC AGGGAGGCCT GCTTCGAGGC ATACCGCTGG    480

CGAGAGCGGG GCGGCGTACA GGCGCCTTCG CTCACCGATA CGGGTTCCGC CACAGCGTGA    540

TTACCCGGTC TCCGTCGGCG GGATAGCTTT CGATCCGGTC TGCGCGGCCG CCGGAAATGC    600

TGCAGATAGC GATCGACCGC GCCGGTCGGT AAACGCCGCA CACGGCACTA TCAATGCGCA    660

CGGCGGGCGT TGATGCCAAA TTGACCGTCC CGACGGGGCT TTATCTGCGG CAAGATTTCA    720

TCCCCAGCCC GGTCGGTGGG CCGATAAATA CGCTGGTCAG CGCGACTCTT CCGGCTGAAT    780

TCGATGCTCT GGGCGCCCGC TCGACGCCGA GTATCTCGAG TGGGCCGCAA ACCCGGTCAA    840

ACGCTGTTAC TGTGGCGTTA CCACAGGTGA ATTTGCGGTG CCAACTGGTG AACACTTGCG    900

AACGGGTGGC ATCGAAATCA ACTTGTTGCG TTGCAGTGAT CTACTCTCTT GCAGAGAGCC    960

GTTGCTGGGA TTAATTGGGA GAGGAAGACA GCATGTCGTT CGTGACCACA CAGCCGGAAG   1020

CCCTGGCAGC TGCGGCGGCG AACCTACAGG GTATTGGCAC GACAATGAAC GCCCAGAACG   1080
```

```
CGGCCGCGGC TGCTCCAACC ACCGGAGTAG TGCCCGCAGC CGCCGATGAA GTATCAGCGC    1140

TGACCGCGGC TCAGTTTGCT GCGCACGCGC AGATGTACCA AACGGTCAGC GCCCAGGCCG    1200

CGGCCATTCA CGAAATGTTC GTGAACACGC TGGTGGCCAA TTCTGGCTCA TACGCGGCCA    1260

CCGAGGCGGC CAACGCAGCC GCTGCCGGCT GAACGGGCTC GCACGAACCT GCTGAAGGAG    1320

AGGGGGAACA TCCGGAGTTC TCGGGTCAGG GGTTGCGCCA GCGCCCAGCC GATTCAGCTA    1380

TCGGCGTCCA TAACAGCAGA CGATCTAGGC ATTCAGTACT AAGGAGACAG CAACATGGC     1440

CTCACGTTTT ATGACGGATC CGCATGCGAT GCGGGACATG GCGGGCCGTT TTGAGGTGCA    1500

CGCCCAGACG GTGGAGGACG AGGCTCGCCG GATGTGGGCG TCCGCGCAAA ACATTTCCGG    1560

TGCGGGCTGG AGTGGCATGG CCGAGGCGAC CTCGCTAGAC ACCATGACCT AGATGAATCA    1620

GGCGTTTCGC AACATCGTGA ACATGCTGCA CGGGGTGCGT GACGGGCTGG TTCGCGACGC    1680

CAACAACTAC GAACAGCAAG AGCAGGCCTC CCAGCAGATC CTGAGCAGCT AGCGCCGAAA    1740

GCCACAGCTG CGTACGCTTT CTCACATTAG GAGAACACCA ATATGACGAT TAATTACCAG    1800

TTCGGGGACG TCGACGCTCA TGGCGCCATG ATCCGCGCTC AGGCGGCGTC GCTTGAGGCG    1860

GAGCATCAGG CCATCGTTCG TGATGTGTTG GCCGCGGGTG ACTTTTGGGG CGGCGCCGGT    1920

TCGGTGGCTT GCCAGGAGTT CATTACCCAG TTGGGCCGTA ACTTCCAGGT GATCTACGAG    1980

CAGGCCAACG CCCACGGGCA GAAGGTGCAG GCTGCCGGCA ACAACATGGC GCAAACCGAC    2040

AGCGCCGTCG GCTCCAGCTG GGCCTAAAAC TGAACTTCAG TCGCGGCAGC ACACCAACCA    2100

GCCGGTGTGC TGCTGTGTCC TGCAGTTAAC TAGCACTCGA CCGCTGAGGT AGCGATGGAT    2160

CAACAGAGTA CCCGCACCGA CATCACCGTC AACGTCGACG GCTTCTGGAT GCTTCAGGCG    2220

CTACTGGATA TCCGCCACGT TGCGCCTGAG TTACGTTGCC GGCCGTACGT CTCCACCGAT    2280

TCCAATGACT GGCTAAACGA GCACCCGGGG ATGGCGGTCA TGCGCGAGCA GGGCATTGTC    2340

GTCAACGACG CGGTCAACGA ACAGGTCGCT GCCCGGATGA AGGTGCTTGC CGCACCTGAT    2400

CTTGAAGTCG TCGCCCTGCT GTCACGCGGC AAGTTGCTGT ACGGGTCAT AGACGACGAG     2460

AACCAGCCGC CGGGTTCGCG TGACATCCCT GACAATGAGT TCCGGGTGGT GTTGGCCCGG    2520

CGAGGCCAGC ACTGGGTGTC GGCGGTACGG GTTGGCAATG ACATCACCGT CGATGACGTG    2580

ACGGTCTCGG ATAGCGCCTC GATCGCCGCA CTGGTAATGG ACGGTCTGGA GTCGATTCAC    2640

CACGCCGACC CAGCCGCGAT CAACGCGGTC AACGTGCCAA TGGAGGAGAT CTCGTGCCGA    2700

ATTCGGCACG AGGCACGAGG CGGTGTCGGT GACGACGGGA TCGATCACGA TCATCGACCG    2760

GCCGGGATCC TTGGCGATCT CGTTGAGCAC GACCCGGGCC CGCGGGAAGC TCTGCGACAT    2820

CCATGGGTTC TTCCCG                                                   2836
```

(2) INFORMATION FOR SEQ ID NO:5:

(i) SEQUENCE CHARACTERISTICS:
        (A) LENGTH: 900 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:5:

```
AACATGCTGC ACGGGGTGCG TGACGGGCTG GTTCGCGACG CCAACAACTA CGAGCAGCAA      60

GAGCAGGCCT CCCAGCAGAT CCTCAGCAGC TAACGTCAGC CGCTGCAGCA CAATACTTTT    120
```

```
ACAAGCGAAG GAGAACAGGT TCGATGACCA TCAACTATCA GTTCGGTGAT GTCGACGCTC      180

ACGGCGCCAT GATCCGCGCT CAGGCCGGGT TGCTGGAGGC CGAACATCAG GCCATCATTC      240

GTGATGTGTT GACCGCGAGT GACTTTTGGG GCGGCGCCGG TTCGGCGGCC TGCCAGGGGT      300

TCATTACCCA ATTGGGCCGT AACTTCCAGG TGATCTACGA ACAGGCCAAC GCCCACGGGC      360

AGAAGGTGCA GGCTGCCGGC AACAACATGG CGCAAACCGA CAGCGCCGTC GGCTCCAGCT      420

GGGCCTGACA CCAGGCCAAG GCCAGGGACG TGGTGTACGA GTGAAGGTTC CTCGCGTGAT      480

CCTTCGGGTG GCAGTCTAGG TGGTCAGTGC TGGGGTGTTG GTGGTTTGCT GCTTGGCGGG      540

TTCTTCGGTG CTGGTCAGTG CTGCTCGGGC TCGGGTGAGG ACCTCGAGGC CCAGGTAGCG      600

CCGTCCTTCG ATCCATTCGT CGTGTTGTTC GGCGAGGACG GCTCCGACGA GGCGGATGAT      660

CGAGGCGCGG TCGGGAAGA TGCCCACGAC GTCGGTTCGG CGTCGTACCT CTCGGTTGAG       720

GCGTTCCTGG GGGTTGTTGG ACCAGATTTG GCGCCAGATC TTCTTGGGGA AGGCGGTGAA      780

CGCCAGCAGG TCGGTGCGGG CGGTGTCGAN GTGCTCGGCC ACCGCGGGGA GTTTGTCGGT      840

CAGAGCGTCG AGTACCCGAT CATATTGGGC AACAACTGAT TCGGCGTTGG GCTGGTCGTA      900

(2) INFORMATION FOR SEQ ID NO:6:

(i) SEQUENCE CHARACTERISTICS:
        (A) LENGTH: 1905 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:6:

GCTCGCCGGA TGTGGGCGTC CGCGCAAAAC ATTTCCGGTG CGGGCTGGAG TGGCATGGCC       60

GAGGCGACCT CGCTAGACAC CATGGCCCAG ATGAATCAGG CGTTTCGCAA CATCGTGAAC      120

ATGCTGCACG GGGTGCGTGA CGGGCTGGTT CGCGACGCCA ACAACTACGA GCAGCAAGAG      180

CAGGCCTCCC AGCAGATCCT CAGCAGCTAA CGTCAGCCGC TGCAGCACAA TACTTTTACA      240

AGCGAAGGAG AACAGGTTCG ATGACCATCA ACTATCAGTT CGGTGATGTC GACGCTCACG      300

GCGCCATGAT CCGCGCTCAG GCCGGGTTGC TGGAGGCCGA GCATCAGGCC ATCATTCGTG      360

ATGTGTTGAC CGCGAGTGAC TTTTGGGGCG GCGCCGGTTC GGCGGCCTGC CAGGGGTTCA      420

TTACCCAGTT GGGCCGTAAC TTCCAGGTGA TCTACGAACA GCCAACACC CACGGGCAGA       480

AGGTGCAAGC TGCCGGCAAC AACATGGCGC AAACCGACAG CGCCGTCNGC TCCAGCTGGG      540

CCTGACACCA GGCCAAGGCC AGGGACGTGG TGTACNAGTG AAGGTTCCTC GCGTGATCCT      600

TCGGGTGGCA GTCTAGGTGG TCAGTGCTGG GGTGTTGGTG GTTTGCTGCT TGGCGGGTTC      660

TTCGGTGCTG GTCAGTGCTG CTCGGGCTCG GGTGAGGACC TCGAGGCCCA GGTAGCGCCG      720

TCCTTCGATC CATTCGTCGT GTTGTTCGGC GAGGACNGCT CCGACGANGC GGATGATCGA      780

GGCGCGGTCG GGAAGATGC CCACGACGTC GGTTCGGCGT CGTACCTCTC GGTTGAAGCG       840

TTCCTGGGGG CCACCGCTTG GCGCCNANGC ACTCCACGCC AATTCGTCNC ACCTAACAGC      900

GGTGGCCAAC GACTATGACT ACGACACCGT TTTTGCCAGG GCCCTCNAAA GGATCTGCGC      960

GTCCCGGCGA CACGCTTTTT GCGATAAGTA CCTCCGGCAA TTCTATGAGT GTACTGCGGN     1020

CCGCGAAAAC CGCAAGGGAG TTGGGTGTGA CGGTTNTTGC AAATGACGGG CGAATCCGGC     1080
```

-continued

```
GGCCAGCTGG CAGAATTCGC AGATTTCTTG ATCAACGTCC CGTCACGCGA CACCGGGCGA    1140

ATCCAGGAAT CTCACATCGT TTTTATTCAT GCGATCTCCG AACATGTCGA ACACGCGCTT    1200

TTCGCGCCTC GCCAATAGGA AAGCCGATCC TTACGCGGCC ATTCGAAAGA TGGTCGCGGA    1260

ACGTGCGGGA CACCAATGGT GTCTCTTCCT CGATAGAGAC GGGGTCATCA ATCGACAAGT    1320

GGTCGGCGAC TACGTACGGA ACTGGCGGCA GTTTGAATGG TTGCCCGGGG CGGCGCGGGC    1380

GTTGAAGAAG CTACGGGCAT GGGCTCCGTA CATCGTTGTC GTGACAAACC AGCAGGGCGT    1440

GGGTGCCGGA TTGATGAGCG CCGTCGACGT GATGGTGATA CATCGGCACC TCCAAATGCA    1500

GCTTGCATCC GATGGCGTGC TGATAGATGG ATTTCAGGTT TGCCCGCACC ACCGTTCGCA    1560

GCGGTGTGGC TGCCGTAAGC CGAGACCGGG TCTGGTCCTC GACTGGCTCG ACGACACCC     1620

CGACAGTGAG CCATTGCTGA GCATCGTGGT TGGGACAGC CTCAGCGATC TTGACATTGG     1680

CACACAACGT CGCCGCTGCT GCCGGTGCAT GTGCCAGTGT CCAGATAGGG GGCGCCAGTT    1740

CTGGCGGTGT CGCTGACGCG TCATTTGACT CGCTCTGGGA GTTCGCTGTC GCAGTCGGAC    1800

ATGCGCGGGG GGAGCGGGGC TAATGGCGAT CTTGCGCGGG CGAGCGCCGT NGCGGNTCGG    1860

ACTNNGCGGT GGCGGGACAG ACGTGGAACC GTACTCGAGC CAGTT                   1905
```

(2) INFORMATION FOR SEQ ID NO:7:

(i) SEQUENCE CHARACTERISTICS:
        (A) LENGTH: 2921 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:7:

```
CGGGATGCCG TGGTGGTTGG TATTGCCCAA ACCCTGGCGC TGGTCCCCGG GGTATCCAGG      60

TCCGGGTCGA CCATCAGCGC TGGACTGTTT CTCGGACTCG ACCGTGAACT GGCCGCCCGA    120

TTCGGATTCC TGCTGGCCAT TCCAGCGGTG TTCGCCTCCG GGTTGTTCTC GTTGCCCGAC    180

GCATTCCACC CGGTAACCGA GGGCATGAGC GCTACTGGCC CGCAGTTGCT GGTGGCCACC    240

CTGATCGCGT TCGTCCTCGG TCTGACCGCG GTGGCCTGGC TGCTGCGGTT TCTGGTGCGA    300

CACAACATGT ACTGGTTCGT CGGCTACCGG GTGCTCGTCG GACGGGCAT GCTCGTGCTG     360

CTGGCTACCG GGACGGTAGC CGCGACATGA CCGTCATCTT GCTACGCCAT GCCCGTTCCA    420

CCTCGAACAC CGCGGGCGTG CTGGCCGGCC GGTCCGGCGT CGACCTCGAC GAGAAGGGGC    480

GCGAGCAGGC CACCGGGTTG ATCGATCGAA TTGGTGACCT GCCGATCCGG GCGGTCGCGT    540

CTTCTCCAAT GCTGCGGTGT CAACGCACCG TCGAACCGCT GGCCGAGGCG CTGTGCCTGG    600

AGCCGCTCAT CGATGACCGG TTCTCCGAAG TCGACTACGG CGAATGGACT GGCAGAAAAA    660

TCGGTGACCT GGTCGACGAG CCGTTGTGGC GGGTAGTCCA GGCCCACCCC AGCGCGGCGG    720

TGTTTCCCGG CGGTGAGGGT TTGGCGCAGG TGCAGACGTG GTTGTCCTGA CGGATTTCCA    780

TGCCGGGGAA CACCAAGACC GGATCGGCAC TGGCGGTCGC CGGCGAAAAC CCGGCCGCCA    840

ATAGGGCGAC CGTCGCTGCG AATGCGCGTG GTACCAGGCG GACCACCTTG AACTCCCATC    900

CGTCGGGGCC AAGCGCATCG CCCGCCGCCG GTTACGGCTA AGGCGTACCA AAACCCGACG    960

GTAATACTTC GGCAATGTCG GGTCNCGACG TTACCGAGAC GTGACCAGNG AGGCNGCGGC   1020

ATTGGATTTA TCGATGGTGC GCGGTTCCCA NCCGGCGGT CCGAANACGT AGCCCAGCCG    1080
```

```
ATCCCGCAGA CGTGTTGCCG ACCGCCAGTC ACGCACGATC GCCACGTACT CGCGGGTCTG    1140

CAGCTTCCAG ATGTTGAACG TGTCGACCCG CTTGGTCAGG CCATAATGCG GTCGGAATAG    1200

CTCCGGCTGA AAGCTACCGA ACAGGCGGTC CCAGATGATG AGGATGCCGC CATAGTTCTT    1260

GTCCANATAC ACCGGGTCCA TTCCGTGGTG GACCCGGTGG TGCGACGGGG TATTGAAGAC    1320

GAATTCGAAC CACCGCGGCA GCCTGTCGAT CCGCTCGGTG TGCACCCAGA ACTGGTAGAT    1380

CAAGTTCAGC GACCAATTGC AGAACACCAT CCAAGGGGGA AGCCCCATCA GTGGCAGCGG    1440

AACCCACATG AGAATCTCGC CGCTGTTGTT CCANTTTCTG GCGCAGCGCG GTGGCGAAGT    1500

TGAAGTATTC GCTGGAGTGA TGCGCCTGGT GGGTAGCCCA GATCAGCCGA ACTCGGTGGG    1560

CGATGCGGTG ATAGGAGTAG TACAGCAGAT CGACACCAAC GATCGCGATC ACCCAGGTGT    1620

ACCACCGGTG GGCGGACAGC TGCCAGGGGG CAAGGTAGGC ATAGATTGCG GCATAACCGA    1680

GCAGGGCAAG GGACTTCCAG CCGGCGGTGG TGGCTATCGA AACCAGCCCC ATCGAGATGC    1740

TGGCCACCGA GTCGCGGGTG AGGTAAGCGC CCGAGGCGGG CCGTGGCTGC CCGGTAGCAG    1800

CGGTCTCGAT GCTTTCCAGC TTGCGGGCCG CCGTCCATTC GAGAATCAGC AGCAATAGAA    1860

AACATGGAAT GGCGAACAGT ACCGGGTCCC GCATTTCCTC GGGCAGCGCT GAGAAGAATC    1920

CGGCGACGGC ATGGCCGAGG CGACCTCGNT AGACACCATG ACCCAGATGA ATCAGGCGTT    1980

TCGCAACATC GTGAACATGC TGCACGGGGT GCGTGACGGG CTGGTTCGCG ACGCCAACAA    2040

NTACGAACAG CAAGAGCAGG CCTCCCAGCA GATCCTCAGC AGCTGACCCG GCCCGACGAC    2100

TCAGGAGGAC ACATGACCAT CAACTATCAA TTCGGGACG TCGACGCTCA CGGCGCCATG    2160

ATCCGCGCTC AGGCCGGGTC GCTGGAGGCC GAGCATCAGG CCATCATTTC TGATGTGTTG    2220

ACCGCGAGTG ACTTTTGGGG CGGCGCCGGT TCGGCGGCCT GCCAGGGGTT CATTACCCAG    2280

CTGGGCCGTA ACTTCCAGGT GATNTACGAG CAGGCCAACG CCCACGGGCA GAAGGTGCAG    2340

GCTGCCGGCA ACAACATGGC ACAAACCGAC AGCGCCGTCG GCTCCAGCTG GCATAAAGN    2400

TGGCTTAAGG CCCGCGCCGT CAATTACAAC GTGGCCGCAC ACCGGTTGGT GTGTGGCCAC    2460

GTTGTTATCT GAACGACTAA CTACTTCGAC CTGCTAAAGT CGGCGCGTTG ATCCCCGGTC    2520

GGATGGTGCT GAACTGGGAA GATGGCCTCA ATGCCCTTGT TGCGGAAGGG ATTGAGGCCA    2580

TCGTGTTTCG TACTTTAGGC GATCAGTGCT GGTTGTGGGA GTCGCTGCTG CCCGACGAGG    2640

TGCGCCGACT GCCCGAGGAA CTGGCCCGGG TGGACGCATT GTTGGACGAT CCGGCGTTCT    2700

TCGCCCCGTT CGTGCCGTTC TTCGACCCGC GCAGGGGCCG GCCGTCGACG CCGATGGAGG    2760

TCTATCTGCA GTTGATGTTT GTGAAGTTCC GCTACCGGCT GGGCTATGAG TCGCTGTGCC    2820

GGGAGGTGGC TGATTCGATC ACCTGACGGC GGTTTTGCCG CATTGCGCTG GACGGGTCGG    2880

TGCCGCATCC GACCACATTG ATGAAGCTCA CCACGCGTTG C                       2921
```

(2) INFORMATION FOR SEQ ID NO:8:

(i) SEQUENCE CHARACTERISTICS:
        (A) LENGTH: 1704 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:8:

-continued

```
CGCGATCGTC GTCAACGANG TCGACCGTCA CCACGGACTG ATCAACAAGT TCGCAGGCGA        60

CGCCGCCCTG GCCATCTTCG GAGCCCCGAA CCGCCTCGAC CGTCCCGAAG ACGCCGCGCT       120

GGCCGCCGCC CGGGCCATAN CCGANCGGCT GGCCNACGAG ATGCCCGAGG TCCAAGCCGG       180

CATCGGGGTG GCGGCAGGCC ANATCGTCGC CGGCAATGTC GGCGCCAAGC AAAGATTCNA       240

ATACACAGTG GTCGGCAAGC CGGTCAACCA NGCGGCCCGA TTGTGCGAAC TGGCCAAATC       300

ACACCCCGCG CGATTGGGTC TCGCCCGCTC GGCTCATGGT CACCCAATTC AAGGACTACT       360

TTGGCCTGGC GCACGACCTG CCGAAGTGGG CGAGTGAAGG CGCCAAAGCC GCCGGTGAGG       420

CCGCCAAGGC GTTGCCGGCC GCCGTTCCGG CCATTCCGAG TGCTGGCCTG AGCGGCGTTG       480

CGGGCGCCGT CGGTCAGGCG GCGTCGGTCG GGGGATTGAA GGTTCCGGCC GTTTGGACCG       540

CCACGACCCC GGCGGCGAGC CCCGCGGTGC TGGCGGCGTC CAACGGCCTC GGAGCCGCGG       600

CCGCCGCTGA AGGTTCGACA CACGCGTTTG GCGGGATGCC GCTCATGGGT ANCGGTGCCG       660

GACGTGCGTT TAACAACTTC GCTGCCCCTC GATACGGATT CAAGCCGACC GTGATCGCCC       720

AACCGCCGGC TGGCGGATGA CCAACTACGT TCGTTGATCG AGGATCGAAT TCNACGATTC       780

AAAGGGAGGA ATTCATATGA CCTCNCGTTT TATGACGGAT CCGCACGCNA TNCGGGACAT       840

GGCGGGCCGT TTTGAGGTGC ACGCCCAGAC GGTGGAGGAC GAGGCTNGCN GGATGTGGGC       900

GTCCGCGCAA ACATTTCCG GTGCGGGCTG GAGTGGCATG GCCGAGGCGA CCTCGNTAGA       960

CACCATGGCC CAGATGAATC AGGCGTTTCN CAACATCGTG AACATGCTGC ACGGGGTGNG      1020

TGACGGGCTG GTTCGCGACG CCAACAACTA CGAACAGCAA GAGCAGGCCT CCCAGCAGAT      1080

CCTCAGCAGC TGACCCGGCC CGACGACTCA GGAGGACACA TGACCATCAA CTATCAATTC      1140

GGGGACGTCG ACGCTCATGG CGCCATGATC CGCGCTNTGG CCGGGTTGCT GGAGGCCGAG      1200

CATCAGGCCA TCATTTCTGA TGTGTTGACC GCGAGTGACT TTTGGGGCGG CGCCGGTTCG      1260

GCGGCCTGCC AGGGGTTCAT TACCCAGTTG GGCCGTAACT TCCAGGTGAT TTACGAGCAG      1320

GCCAACGCCC ACGGGCAGAA GGTGCAGGCT GCCGGCAACA ACATGGCACA AACCGACAGC      1380

GCCGTNGGNT CCAGCTGGGC CTAACCCGGG TCNTAAGTTG GGTCCGCGCA GGGCGGGCCG      1440

ATCAGCGTNG ACTTTGGCGC CCGATACACG GGCATNTTNT NGTCGGGAAC ACTGCGCCCG      1500

CGTCAGNTGC CCGCTTCCCC TTGTTNGGCG ACGTGCTCGG TGATGGCTTT GACGACCGCT      1560

TCGCCGGCGC GGCCAATCAA TTGGTCGCGC TTGCCTNTAG CCCATTCGTG CGACGCCCGC      1620

GGCGCCGCGA GTTGTCCCTT GAAATAAGGA ATCACAGCAC GGGCGAACAG CTCATAGGAG      1680

TGAAAGGTTG CCGTGGCGGG GCCC                                             1704
```

(2) INFORMATION FOR SEQ ID NO:9:

(i) SEQUENCE CHARACTERISTICS:
        (A) LENGTH: 2286 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:9:

```
CCGTCTTGGC GTCTGGGCGC ATTGTGATCT GGGCCANTTG CCCCTCCACC CAGACCGCGC        60

CCAGCTTGTC GATCCAGCCC GCGACCCGGA TTGCCACCGC GCGAACCGGG AACGGATTCT       120

CCGCTGAATT CTGGGTCACT TCGCAGTCGC GCGGGTGATC CTGTTGGCGA NCAGCGTCTG       180
```

```
GAACGGGCGT CNAACGCGTG CCGTAAGCCC AGCGTGTACG CCGTCAGCCC GACGCCGATG    240

CCGAATGCCT TGCCGCCCAA GCTGAGCCGC GCGGGCTCCA CCAAGAGCGT CACGGTGAGC    300

CAGCCAACCA GATGCAAGGC GACGATCACC GCGAAGTGCC GAATTCGGCA CGAGAGGTGC    360

TGGAAATCCA GCAATACGCC CGCGAGCCGA TCTCGTTGGA CCAGACCATC GGCGACGANG    420

GCGACAGNCA GCTTGGCGAT TCATCGAAA ACAGCGAGGC GGTGGTGGNC GTCGACGCGG     480

TGTCCTTCAC TTTGCTGCAT GATCAACTGC ANTCGGTGCT GGACACGCTC TCCGAGCGTG    540

AGGCGGGCGT GGTGCGGCTA CGCTTCGGCC TTACCGACGG CCAGCCGCGC ACCCTTGACG    600

AGATCGGCCA GGTCTACGGC GTGACCCGGG AACGCATCCG CCAGATCGAA TCCAAGACTA    660

TGTCGAAGTT GCGCCATCCG AGCCGCTCAC AGGTCCTGCG CGACTATCGT GCCGAATTCG    720

GCACGAGCCG TTTTGAGGTG CACGCCCAGA CGGTGGAGGA CGAGGCTCGC CGGATGTGGG    780

CGTCCGCGCA AAACATTTCC GGTGCGGGCT GGAGTGGCAT GGCCGANGCG ACCTCGCTAG    840

ACACCATGGC CCAGATGAAT CAGGCGTTTC GCAACATCGT GAACATGCTG CACGGGGTGC    900

GTGACGGGCT GGTTCGCGAC GCCAACAACT ACGAACAGCA AGAGCAGGCC TCCCAGCAGA    960

TCCTCAGCAG CTGACCCGGC CGACGACTC AGGAGGACAC ATGACCATCA ACTATCAATT     1020

CGGGGACGTC GACGCTCATG GCGCCATGAT CCGCGCTCTG GCCGGGTTGC TGGAGGCCGA    1080

GCATCAGGCC ATCATTTCTG ATGTGTTGAC CGCGAGTGAC TTTTGGGGCG GCGCCGGTTC    1140

GGCGGCCTGC CAGGGGTTCA TTACCCAGTT GGGCCGTAAC TTCCAGGTGA CTACGAGCA     1200

GGCCAACGCC CACGGGCAGA AGGTGCAGGC TGCCGGCAAC AACATGGCAC AAACCGACAG    1260

CGCCGTCGGC TCCAGCTGGG CCTAACCCGG GTCCTAAGTT GGGTCCGCGC AGGGCGGGCC    1320

GATCAGCGTC GACTTTGGCG CCCGATACAC GGGCATGTNG TNGTCGGGAA CACTGCGCCC    1380

GCGTCAGCTG CCCGCTTCCC CTTGTTCGGC GACGTGCTCG GTGATGGCTT TGACGACCGC    1440

TTCGCCGGCG CGGCCAATCA ATTGGTCGCG CTTGCCTCTA GCCTCGTGCC GAATTCGGCA    1500

CGAGGGTGCT GGTGCCGCGC TATCGGCAGC ACGTGAGCTC CACGACGAAC TCATCCCAGT    1560

GCTGGGTTCC GCGGAGTTCG GCATCGGCGT GTCGGCCGGA AGGGCCATCG CCGGCCACAT    1620

CGGCGCTCAA GCCCGCTTCG AGTACACCGT CATCGGCGAC CCGGTCAACG AGGCCGCCCG    1680

GCTCACCGAA CTGGCCAAAG TCGAGGATGG CCACGTTCTG GCGTCGGCGA TCGCGGTCAG    1740

TGGCGCCCTG GACGCCGAAG CATTGTGTTG GGATGTTGGC GAGGTGGTTG AGCTCCGCGG    1800

ACGTGCTGCA CCCACCCAAC TAGCCAGGCC AATGAATNTG GCNGCACCCG AAGAGGTTTC    1860

CAGCGAAGTA CGCGGCTAGT CGCGCTTGGC TGCNTTCTTC GCCGGCACCT TCCGGGCAGC    1920

TTTCCTGGCT GGCCGTTTTG CCGGACCCCG GGCTCGGCGA TCGCCAACA GCTCGGCGGC     1980

GCGCTCGTCG GTTATGGAAG CCACGTNGTC GCCCTTACGC AGGCTGGCAT TGGTCTCACC    2040

GTCGGTGACG TACGGCCCGA ATCGGCCGTC CTTGATGACC ATTGGCTTGC CAGACGCCGG    2100

ATNTGNTCCC AGCTCGCGCA GCGGCGGAGC CGAAGCGCTT TGCCGGCCAC GACNTTTCGG    2160

CTCTGNGTAG ATNTTCAGGG CTTCGTCGAG CGNGATGGTG AATATATGGT CTTCGGTGAC    2220

CAGTGATCGA GAATCGTTGC CGCGCTTTAG ATACGGTCNG TAGCGCCCGT TCTGCGCGGT    2280

GATNTC                                                              2286
```

(2) INFORMATION FOR SEQ ID NO:10:

(i) SEQUENCE CHARACTERISTICS:
        (A) LENGTH: 1136 base pairs
        (B) TYPE: nucleic acid

```
            (C) STRANDEDNESS: double
            (D) TOPOLOGY: linear (ii) MOLECULE TYPE: DNA (genomic)

(vi) ORIGINAL SOURCE:
         (A) ORGANISM: Mycobacterium tuberculosis (xi) SEQUENCE DESCRIPTION: SEQ ID NO:10:

GGGCATCTTC CCCGACCGCG CCTCGATCAT CCGCCTCGTC GGAGCCGTCC TCGCCGAACA      60

ACACGACGAA TGGATCGAAG GACGGCGCTA CCTGGGCCTC GAGGTCCTCA CCCGAGCCCG     120

AGCAGCACTG ACCAGCACCG AAGAACCGCC AAGCAGCAAA CCACCAACAC CCCAGCACTG     180

ACCACCTAGA CTGCCACCCG AAGGATCACG CGAGGAACCT TCACTCGTAC ACCACGTCCC     240

TGGCCTTGGC CTGGTGTCAG GCCCAGCTGG AGCCGACGGC GCTGTCGGTT TGCGCCATGT     300

TGTTGCCGGC AGCCTGCACC TTCTGCCCGT GGGCGTTGGC CTGCTCGTAG ATCACCTGGA     360

AGTTACGGCC CAACTGGGTA ATGAACCCCT GGCAGGCCGC CGAACCGGCG CCGCCCCAAA     420

AGTCACTCGC GGTCAACACA TCACGAATGA TGGCCTGATG CTCGGCCTCC AGCAACCCGG     480

CCTGAGCGCG GATCATGGCG CCGTGAGCGT CGACATCACC GAACTGATAG TTGATGGTCA     540

TCGAACCTGT TCTCCTTCGC TTGTAAAAGT ATTGTGCTGC AGCGGCTGAC GTTAGCTGCT     600

GAGGATCTGC TGGGAGGCCT GCTCTTGCCT CGTGCCGAAT TCGGCACGAG AGGCCGCCTT     660

CGAAGAAATC CTTTGAGAAT TCGCCAAGGC CGTCGACCCA GCATGGGGTC AGCTCGCCAG     720

CCGCGCCGGC TGGCAACCGT TCCCGCTCGA GAAAGACCTG GAGGAATACC AGTGACAAAC     780

GACCTCCCAG ACGTCCGAGA GCGTGACGGC GGTCCACGTC CCGCTCCTCC TGCTGGCGGG     840

CCACGCTTGT CAGACGTGTG GGTTTACAAC GGGCGGGCGT ACGACCTGAG TGAGTGGATT     900

TCCAAGCATC CCGGCGGCGC CTTNTTCATT GGGCGGACCA AGAACCGCGA CATCACCGCA     960

ATCGTCAAGT CCTACCATCG TGATCCGGCG ATTGTCGAGC GAATCCTGCA GCGGAGGTAC    1020

GCGTTGGGCC GCGACGCAAC CCCTAGGGAC ATCCACCCCA AGCACAATGC ACCGGCATTT    1080

CTGTTCAAAG ACGACTTCAA CAGCTGGCGG GACACCCCGA AGTATCGATT NGACGA       1136

(2) INFORMATION FOR SEQ ID NO:11:

(i) SEQUENCE CHARACTERISTICS:
        (A) LENGTH: 967 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
         (A) ORGANISM: Mycobacterium tuberculosis (xi) SEQUENCE DESCRIPTION: SEQ ID NO:11:

TGAGCGCCAA CCCTACCGTC GGTTCGTCAC ACGGACCGCA TGGCCTGCTC CGCGGACTGC      60

CGCTAGGGTC GCGGATCACT CGGCGTAGCG GCGCCTTTGC CCACCGATAT GGGTTCCGTC     120

ACAGTGTGGT TGCCCGCCCG CCATCGGCCG GATAACGCCA TGACCTCAGC TCGGCAGAAA     180

TGACAATGCT CCCAAAGGCG TGAGCACCCG AAGACAACTA AGCAGGAGAT CGCATGCCGT     240

TTGTGACTAC CCAACCAGAA GCACTGGCGG CGGCGGCCGG CAGTCTGCAG GGAATCGGCT     300

CCGCATTGAA CGCCCAGAAT GCGGCTGCGG CGACTCCCAC GACGGGGGTG GTCCGGCGGC     360

CGCCGATGAA NTGTCGGCGC TGACGGCGGC TCAGTTCGCG GCACACGCCC AGATCTATCA     420

GGCCGTCAGC GCCCAGGCCG CGGCGATTCA CGAGATGTTC GTCAACACTC TACAGATGAG     480
```

-continued

```
CTCAGGGTCG TATGCTGCTA CCGAGGCCGC CAACGCGGCC GCGGCCGGNT AGAGGAGTCA        540

CTGCGATGGA TTTTGGGGCG TTGCCGCCGG AGGTCAATTC GGTGCGGATG TATGCCGTTC        600

CTGGCTCGGC ACCAATGGTC GCTGCGGCGT CGGCCTGGAA CGGGTTGGCC GCGGAGCTGA        660

GTTCGGCGGC CACCGGTTAT GAGACGGTGA TCACTCAGCT CAGCAGTGAG GGGTGGCTAG        720

GTCCGGCGTC AGCGGCGATG GCCGAGGCAG TTGCGCCGTA TGTGGCGTGG ATGAGTGCCG        780

CTGCGGCGCA AGCCGAGCAG GCGGCCACAC AGGCCAGGGC CGCCGCGGCC GCTTTTGAGG        840

CGGCGTTTGC CGCGACGGTG CCTCCGCCGT TGATCGCGGC CAACCGGGCT TCGTTGATGC        900

AGCTGATCTC GACGAATGTC TTTGGTCAGA ACACCTCGGC GATCGCGGCC GCCGAAGCTC        960

AGTACGG                                                                  967
```

(2) INFORMATION FOR SEQ ID NO:12:

(i) SEQUENCE CHARACTERISTICS:
        (A) LENGTH: 585 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Mycobacterium tuberculosis (xi) SEQUENCE DESCRIPTION: SEQ ID NO:12:

```
TGGATTCCGA TAGCGGTTTC GGCCCCTCGA CGGGCGACCA CGGCGCGCAG GCCTCCGAAC         60

GGGGGGCCGG GACGCTGGGA TTCGCCGGGA CCGCAACCAA AGAACGCCGG GTCCGGGCGG        120

TCGGGCTGAC CGCACTGGCC GGTGATGAGT TCGGCAACGG CCCCCGGATG CCGATGGTGC        180

CGGGGACCTG GGAGCAGGGC AGCAACGAGC CCGAGGCGCC CGACGGATCG GGGAGAGGGG        240

GAGGCGACGG CTTACCGCAC GACAGCAAGT AACCGAATTC GAATCACGT GGACCCGTAC         300

GGGTCGAAAG GAGAGATGTT ATGAGCCTTT TGGATGCTCA TATCCCACAG TTGGTGGCCT        360

CCCAGTCGGC GTTTGCCGCC AAGGCGGGGC TGATGCGGCA CACGATCGGT CAGGCCGAGC        420

AGGCGGCGAT GTCGGCTCAG GCGTTTCACC AGGGGGAGTC GTCGGCGGCG TTTCAGGCCG        480

CCCATGCCCG GTTTGTGGCG GCGGCCGCCA AAGTCAACAC CTTGTTGGAT GTCGCGCAGG        540

CGAATCTGGG TGAGGCCGCC GGTACCTATG TGGCCGCCGA TGCTG                        585
```

(2) INFORMATION FOR SEQ ID NO:13:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:13:

```
Ala Leu Val Thr Thr Asn Phe Phe Gly Val Asn Thr Ile Pro Ile Ala
1               5                   10                  15

Leu Asn Glu Ala Asp Tyr Leu Arg Met Trp Ile Gln Ala Ala Thr Val
            20                  25                  30

Met Ser His Tyr Gln Ala Val Ala His Glu Ile Trp Cys Leu His Glu
        35                  40                  45
```

```
Xaa Ala Ser Ser Gly Lys Pro Trp Ala Ser Ile Thr Thr Gly Ala Pro
    50                  55                  60

Gly Ser Pro Ala Ser Thr Thr Arg Ser Arg Thr Pro Leu Val Ser Thr
65                  70                  75                  80

Asn Arg Xaa Val Xaa Ala Pro Ile Val Ser Pro Asn His Thr Gly His
                85                  90                  95

Arg Pro Glu Lys Gly Leu Gly Ser Xaa Gln Arg Arg Leu Ser Arg Val
            100                 105                 110

Leu Pro Arg Ile Ile Asp Arg Pro Ala Gly Pro Xaa Gly Pro Pro Leu
        115                 120                 125

Thr Ser Gly Ser His Phe Leu Cys Ser Trp His Gly Tyr Ser Ser Gln
    130                 135                 140
```

(2) INFORMATION FOR SEQ ID NO:14:

(i) SEQUENCE CHARACTERISTICS:
        (A) LENGTH: 352 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:14:

```
His Ala Leu Ala Ala Gln Tyr Thr Glu Ile Ala Thr Glu Leu Ala Ser
1               5                   10                  15

Val Leu Ala Ala Val Gln Ala Ser Ser Trp Gln Gly Pro Ser Ala Asp
            20                  25                  30

Arg Phe Val Val Ala His Gln Pro Phe Arg Tyr Trp Leu Thr His Ala
        35                  40                  45

Ala Thr Val Ala Thr Ala Ala Ala Ala His Xaa Thr Ala Ala Ala
    50                  55                  60

Gly Tyr Thr Ser Ala Leu Gly Gly Met Pro Thr Leu Ala Glu Leu Ala
65                  70                  75                  80

Ala Asn His Ala Met His Gly Ala Leu Val Thr Thr Asn Phe Phe Gly
                85                  90                  95

Val Asn Thr Ile Pro Ile Ala Leu Asn Glu Ala Asp Tyr Leu Arg Met
            100                 105                 110

Trp Ile Gln Ala Ala Thr Val Met Ser His Tyr Gln Ala Val Ala His
        115                 120                 125

Glu Ser Val Ala Ala Thr Pro Ser Thr Pro Ala Pro Gln Ile Val
    130                 135                 140

Thr Ser Ala Ala Ser Ser Ala Ala Ser Ser Phe Pro Asp Pro Thr
145                 150                 155                 160

Lys Leu Ile Leu Gln Leu Leu Lys Asp Phe Leu Glu Leu Leu Arg Tyr
                165                 170                 175

Leu Ala Val Glu Leu Leu Pro Gly Pro Leu Gly Asp Leu Ile Ala Gln
            180                 185                 190

Val Leu Asp Trp Phe Ile Ser Phe Val Ser Gly Pro Val Phe Thr Phe
        195                 200                 205

Leu Ala Tyr Leu Val Leu Asp Pro Leu Ile Tyr Phe Gly Pro Phe Ala
    210                 215                 220

Pro Leu Thr Ser Pro Val Leu Leu Pro Ala Val Glu Leu Arg Asn Arg
225                 230                 235                 240
```

```
Leu Lys Thr Ala Thr Gly Leu Thr Leu Pro Pro Thr Val Ile Phe Asp
            245                 250                 255

His Pro Thr Pro Thr Ala Val Ala Glu Tyr Val Ala Gln Gln Met Ser
            260                 265                 270

Gly Ser Arg Pro Thr Glu Ser Gly Asp Pro Thr Ser Gln Val Val Glu
            275                 280                 285

Pro Ala Arg Ala Glu Phe Gly Thr Ser Ala Val His Gln Ile Pro Pro
            290                 295                 300

Arg Pro Ala Asp Thr Arg Arg Ala Cys Arg His Arg Asp Asp Val Pro
305                 310                 315                 320

Arg Asp Ser Arg Ile Ala Gln His Arg Asp Gly Ala Gly Leu Asp Pro
            325                 330                 335

Thr Glu Arg Gly Thr Ser Glu Gly Asp Gln Gly Leu Val Ser Gly Trp
            340                 345                 350
```

(2) INFORMATION FOR SEQ ID NO:15:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:15:

```
Met Asp Phe Gly Ala Leu Pro Pro Glu Val Asn Ser Val Arg Met Tyr
1               5                   10                  15

Ala Val Pro Gly Ser Ala Pro Met Val Ala Ala Ser Ala Trp Asn
            20                  25                  30

Gly Leu Ala Ala Glu Leu Ser Ser Ala Ala Thr Gly Tyr Glu Thr Val
            35                  40                  45

Ile Thr Gln Leu Ser Ser Glu Gly Trp Leu Gly Pro Ala Ser Ala Ala
    50                  55                  60

Met Ala Glu Ala Val Ala Pro Tyr Val Ala Trp Met Ser Ala Ala Ala
65                  70                  75                  80

Ala Gln Ala Glu Gln Ala Ala Thr Gln Ala Arg Ala Ala Ala Ala
            85                  90                  95

Phe Glu Ala Ala Phe Ala Ala Thr Val Pro Pro Pro Leu Ile Ala Ala
            100                 105                 110

Asn Arg Ala Ser Leu Met Gln Leu Ile Ser Thr Asn Val Phe Gly Gln
            115                 120                 125

Asn Thr Ser Ala Ile Ala Ala Ala Glu Ala Gln Tyr Gly
            130                 135                 140
```

(2) INFORMATION FOR SEQ ID NO:16:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:16:

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
                20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr
50                  55

(2) INFORMATION FOR SEQ ID NO:17:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:17:

Met Thr Ile Asn Tyr Gln Phe Gly Asp Val Asp Ala His Gly Ala Met
1               5                   10                  15

Ile Arg Ala Gln Ala Ala Ser Leu Glu Ala Glu His Gln Ala Ile Val
                20                  25                  30

Arg Asp Val Leu Ala Ala Gly Asp Phe Trp Gly Gly Ala Gly Ser Val
        35                  40                  45

Ala Cys Gln Glu Phe Ile Thr Gln Leu Gly Arg Asn Phe Gln Val Ile
50                  55                  60

Tyr Glu Gln
65

(2) INFORMATION FOR SEQ ID NO:18:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:18:

Met Ala Ser Arg Phe Met Thr Asp Pro His Ala Met Arg Asp Met Ala
1               5                   10                  15

Gly Arg Phe Glu Val His Ala Gln Thr Val Glu Asp Glu Ala Arg Arg
                20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Thr
50                  55

(2) INFORMATION FOR SEQ ID NO:19:

(i) SEQUENCE CHARACTERISTICS:
        (A) LENGTH: 94 amino acids
        (B) TYPE: amino acid

```
            (C) STRANDEDNESS: single
            (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:19:

Met Thr Ile Asn Tyr Gln Phe Gly Asp Val Asp Ala His Gly Ala Met
 1               5                  10                  15

Ile Arg Ala Gln Ala Ala Ser Leu Glu Ala Glu His Gln Ala Ile Val
            20                  25                  30

Arg Asp Val Leu Ala Ala Gly Asp Phe Trp Gly Gly Ala Gly Ser Val
        35                  40                  45

Ala Cys Gln Glu Phe Ile Thr Gln Leu Gly Arg Asn Phe Gln Val Ile
50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90

(2) INFORMATION FOR SEQ ID NO:20:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:20:

Asn Met Leu His Gly Val Arg Asp Gly Leu Val Arg Asp Ala Asn Asn
 1               5                  10                  15

Tyr Glu Gln Gln Glu Gln Ala Ser Gln Gln Ile Leu Ser Ser
            20                  25                  30

(2) INFORMATION FOR SEQ ID NO:21:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:21:

Met Thr Ile Asn Tyr Gln Phe Gly Asp Val Asp Ala His Gly Ala Met
 1               5                  10                  15

Ile Arg Ala Gln Ala Gly Leu Leu Glu Ala Glu His Gln Ala Ile Ile
            20                  25                  30

Arg Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Ile
50                  55                  60

Tyr Glu Gln Ala Asn Ala His Gly Gln Lys Val Gln Ala Ala Gly Asn
```

```
65                  70                  75                  80
Asn Met Ala Gln Thr Asp Ser Ala Val Gly Ser Ser Trp Ala
                    85                  90
```

(2) INFORMATION FOR SEQ ID NO:22:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:22:

```
Ala Arg Arg Met Trp Ala Ser Ala Gln Asn Ile Ser Gly Ala Gly Trp
1               5                   10                  15
Ser Gly Met Ala Glu Ala Thr Ser Leu Asp Thr Met Ala Gln Met Asn
                20                  25                  30
Gln Ala Phe Arg Asn Ile Val Asn Met Leu His Gly Val Arg Asp Gly
            35                  40                  45
Leu Val Arg Asp Ala Asn Asn Tyr Glu Gln Gln Glu Gln Ala Ser Gln
        50                  55                  60
Gln Ile Leu Ser Ser
65
```

(2) INFORMATION FOR SEQ ID NO:23:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:23:

```
Met Thr Ile Asn Tyr Gln Phe Gly Asp Val Asp Ala His Gly Ala Met
1               5                   10                  15
Ile Arg Ala Gln Ala Gly Leu Leu Glu Ala Glu His Gln Ala Ile Ile
                20                  25                  30
Arg Asp Val Leu Thr Ala Ser Asp Phe Trp Gly Gly Ala Gly Ser Ala
            35                  40                  45
Ala Cys Gln Gly Phe Ile Thr Gln Leu Gly Arg Asn Phe Gln Val Ile
        50                  55                  60
Tyr Glu Gln Ala Asn Thr His Gly Gln Lys Val Gln Ala Ala Gly Asn
65                  70                  75                  80
Asn Met Ala Gln Thr Asp Ser Ala Val Xaa Ser Ser Trp Ala
                    85                  90
```

(2) INFORMATION FOR SEQ ID NO:24:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (vi) ORIGINAL SOURCE:
    (A) ORGANISM: Mycobacterium tuberculosis (xi) SEQUENCE DESCRIPTION:

-continued

```
                50                  55                  60
Arg Asn Ile Val Asn Met Leu His Gly Val Arg Asp Gly Leu Val Arg
 65                  70                  75                  80

Asp Ala Asn Asn Tyr Glu Gln Gln Glu Gln Ala Ser Gln Gln Ile Leu
                 85                  90                  95

Ser Ser
```

(2) INFORMATION FOR SEQ ID NO:27:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:27:

```
Met Thr Ile Asn Tyr Gln Phe Gly Asp Val Asp Ala His Gly Ala Met
 1                   5                  10                  15

Ile Arg Ala Xaa Ala Gly Leu Leu Glu Ala Glu His Gln Ala Ile Ile
                 20                  25                  30

Ser Asp Val Leu Thr Ala Ser Asp Phe Trp Gly Gly Ala Gly Ser Ala
                 35                  40                  45

Ala Cys Gln Gly Phe Ile Thr Gln Leu Gly Arg Asn Phe Gln Val Ile
         50                  55                  60

Tyr Glu Gln Ala Asn Ala His Gly Gln Lys Val Gln Ala Ala Gly Asn
 65                  70                  75                  80

Asn Met Ala Gln Thr Asp Ser Ala Val Gly Ser Ser Trp Ala
                 85                  90
```

(2) INFORMATION FOR SEQ ID NO:28:

(i) SEQUENCE CHARACTERISTICS:
        (A) LENGTH: 81 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:28:

```
Arg Phe Glu Val His Ala Gln Thr Val Glu Asp Glu Ala Arg Arg Met
 1                   5                  10                  15

Trp Ala Ser Ala Gln Asn Ile Ser Gly Ala Gly Trp Ser Gly Met Ala
                 20                  25                  30

Xaa Ala Thr Ser Leu Asp Thr Met Ala Gln Met Asn Gln Ala Phe Arg
                 35                  40                  45

Asn Ile Val Asn Met Leu His Gly Val Arg Asp Gly Leu Val Arg Asp
         50                  55                  60

Ala Asn Asn Tyr Glu Gln Gln Glu Gln Ala Ser Gln Gln Ile Leu Ser
 65                  70                  75                  80

Ser
```

(2) INFORMATION FOR SEQ ID NO:29:

(i) SEQUENCE CHARACTERISTICS:
    (A) LENGTH: 94 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: Mycobacterium tuberculosis (xi) SEQUENCE DESCRIPTION: SEQ ID NO:29:

```
Met Thr Ile Asn Tyr Gln Phe Gly Asp Val Asp Ala His Gly Ala Met
1               5                  10                  15

Ile Arg Ala Leu Ala Gly Leu Leu Glu Ala Glu His Gln Ala Ile Ile
            20                  25                  30

Ser Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90
```

(2) INFORMATION FOR SEQ ID NO:30:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:30:

```
Gln Glu Gln Ala Ser Gln Gln Ile Leu Ser Ser
1               5                  10
```

(2) INFORMATION FOR SEQ ID NO:31:

(i) SEQUENCE CHARACTERISTICS:
        (A) LENGTH: 94 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:31:

```
Met Thr Ile Asn Tyr Gln Phe Gly Asp Val Asp Ala His Gly Ala Met
1               5                  10                  15

Ile Arg Ala Gln Ala Gly Leu Leu Glu Ala Glu His Gln Ala Ile Ile
            20                  25                  30

Arg Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Ile
    50                  55                  60
```

```
Tyr Glu Gln Ala Asn Ala His Gly Gln Lys Val Gln Ala Ala Gly Asn
 65                  70                  75                  80

Asn Met Ala Gln Thr Asp Ser Ala Val Gly Ser Ser Trp Ala
                 85                  90
```

(2) INFORMATION FOR SEQ ID NO:32:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:32:

```
Met Ser Phe Val Thr Thr Gln Pro Glu Ala Leu Ala Ala Ala Ala Ala
 1               5                  10                  15

Asn Leu Gln Gly Ile Gly Thr Thr Met Asn Ala Gln Asn Ala Ala Ala
                 20                  25                  30

Ala Ala Pro Thr Thr Gly Val Val Pro Ala Ala Ala Asp Glu Val Ser
                 35                  40                  45

Ala Leu Thr Ala Ala Gln Phe Ala Ala His Ala Gln Met Tyr Gln Thr
 50                  55                  60

Val Ser Ala Gln Ala Ala Ala Ile His Glu Met Phe Val Asn Thr Leu
 65                  70                  75                  80

Val Ala Ser Ser Gly Ser Tyr Ala Ala Thr Glu Ala Ala Asn Ala Ala
                 85                  90                  95

Ala Ala Gly
```

(2) INFORMATION FOR SEQ ID NO:33:

(i) SEQUENCE CHARACTERISTICS:
        (A) LENGTH: 99 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:33:

```
Met Ser Phe Val Thr Thr Gln Pro Glu Ala Leu Ala Ala Ala Ala Ala
 1               5                  10                  15

Asn Leu Gln Gly Ile Gly Thr Thr Met Asn Ala Gln Asn Ala Ala Ala
                 20                  25                  30

Ala Ala Pro Thr Thr Gly Val Val Pro Ala Ala Ala Asp Glu Val Ser
                 35                  40                  45

Ala Leu Thr Ala Ala Gln Phe Ala Ala His Ala Gln Met Tyr Gln Thr
 50                  55                  60

Val Ser Ala Gln Ala Ala Ala Ile His Glu Met Phe Val Asn Thr Leu
 65                  70                  75                  80

Val Ala Ser Ser Gly Ser Tyr Ala Ala Thr Glu Ala Ala Asn Ala Ala
                 85                  90                  95

Ala Ala Gly
```

(2) INFORMATION FOR SEQ ID NO:34:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:34:

Asp Pro His Ala Met Arg Asp Met Ala Gly Arg Phe Glu Val His
1               5                   10                  15

(2) INFORMATION FOR SEQ ID NO:35:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:35:

Arg Asp Met Ala Gly Arg Phe Glu Val His Ala Gln Thr Val Glu
1               5                   10                  15

(2) INFORMATION FOR SEQ ID NO:36:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:36:

Arg Phe Glu Val His Ala Gln Thr Val Glu Asp Glu Ala Arg Arg
1               5                   10                  15

(2) INFORMATION FOR SEQ ID NO:37:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:37:

Ala Gln Thr Val Glu Asp Glu Ala Arg Arg Met Trp Ala Ser Ala
1               5                   10                  15

(2) INFORMATION FOR SEQ ID NO:38:

(i) SEQUENCE CHARACTERISTICS:

(A) LENGTH: 15 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: Mycobacterium tuberculosis (xi) SEQUENCE DESCRIPTION: SEQ ID NO:38:

```
Asp Glu Ala Arg Arg Met Trp Ala Ser Ala Gln Asn Ile Ser Gly
1               5                   10                  15
```

(2) INFORMATION FOR SEQ ID NO:39:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: Mycobacterium tuberculosis (xi) SEQUENCE DESCRIPTION: SEQ ID NO:39:

```
Met Trp Ala Ser Ala Gln Asn Ile Ser Gly Ala Gly Trp Ser Gly
1               5                   10                  15
```

(2) INFORMATION FOR SEQ ID NO:40:

(i) SEQUENCE CHARACTERISTICS:
(A) LENGTH: 15 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: Mycobacterium tuberculosis (xi) SEQUENCE DESCRIPTION: SEQ ID NO:40:

```
Gln Asn Ile Ser Gly Ala Gly Trp Ser Gly Met Ala Glu Ala Thr
1               5                   10                  15
```

(2) INFORMATION FOR SEQ ID NO:41:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: Mycobacterium tuberculosis (xi) SEQUENCE DESCRIPTION: SEQ ID NO:41:

```
Ala Gly Trp Ser Gly Met Ala Glu Ala Thr Ser Leu Asp Thr Met Thr
1               5                   10                  15
```

(2) INFORMATION FOR SEQ ID NO:42:

(i) SEQUENCE CHARACTERISTICS:
(A) LENGTH: 15 amino acids
(B) TYPE: amino acid
(C) STRANDEDNESS: single

```
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:42:

Met Ala Glu Ala Thr Ser Leu Asp Thr Met Ala Gln Met Asn Gln
1               5                  10                  15

(2) INFORMATION FOR SEQ ID NO:43:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:43:

Ser Leu Asp Thr Met Ala Gln Met Asn Gln Ala Phe Arg Asn Ile
1               5                  10                  15

(2) INFORMATION FOR SEQ ID NO:44:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:44:

Ala Gln Met Asn Gln Ala Phe Arg Asn Ile Val Asn Met Leu His
1               5                  10                  15

(2) INFORMATION FOR SEQ ID NO:45:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:45:

Ala Phe Arg Asn Ile Val Asn Met Leu His Gly Val Arg Asp Gly
1               5                  10                  15

(2) INFORMATION FOR SEQ ID NO:46:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide
```

(vi) ORIGINAL SOURCE:
    (A) ORGANISM: Mycobacterium tuberculosis (xi) SEQUENCE DESCRIPTION: SEQ ID NO:46:

Val Asn Met Leu His Gly Val Arg Asp Gly Leu Val Arg Asp Ala
1               5                   10                  15

(2) INFORMATION FOR SEQ ID NO:47:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:47:

Gly Val Arg Asp Gly Leu Val Arg Asp Ala Asn Asn Tyr Glu Gln
1               5                   10                  15

(2) INFORMATION FOR SEQ ID NO:48:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:48:

Leu Val Arg Asp Ala Asn Asn Tyr Glu Gln Gln Glu Gln Ala Ser
1               5                   10                  15

(2) INFORMATION FOR SEQ ID NO:49:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:49:

Asn Asn Tyr Glu Gln Gln Glu Gln Ala Ser Gln Gln Ile Leu Ser Ser
1               5                   10                  15

(2) INFORMATION FOR SEQ ID NO:50:

(i) SEQUENCE CHARACTERISTICS:
        (A) LENGTH: 17 amino acids
        (B) TYPE: amino acid
        (C) STRANDEDNESS: single
        (D) TOPOLOGY: linear
    (ii) MOLECULE TYPE: peptide
    (vi) ORIGINAL SOURCE:
        (A) ORGANISM: Mycobacterium tuberculosis (xi) SEQUENCE DESCRIPTION: SEQ ID NO:50:

```
Met Ala Ser Arg Phe Met Thr Asp Pro His Ala Met Arg Asp Met Ala
1               5                   10                  15

Gly
```

(2) INFORMATION FOR SEQ ID NO:51:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:51:

```
Met Thr Ile Asn Tyr Gln Phe Gly Asp Val Asp Ala His Gly Ala
1               5                   10                  15
```

(2) INFORMATION FOR SEQ ID NO:52:

(i) SEQUENCE CHARACTERISTICS:
        (A) LENGTH: 15 amino acids
        (B) TYPE: amino acid
        (C) STRANDEDNESS: single
        (D) TOPOLOGY: linear
    (ii) MOLECULE TYPE: peptide (vi) ORIGINAL SOURCE:
        (A) ORGANISM: Mycobacterium tuberculosis (xi) SEQUENCE DESCRIPTION: SEQ ID NO:52:

```
Gln Phe Gly Asp Val Asp Ala His Gly Ala Met Ile Arg Ala Gln
1               5                   10                  15
```

(2) INFORMATION FOR SEQ ID NO:53:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:53:

```
Asp Ala His Gly Ala Met Ile Arg Ala Gln Ala Ala Ser Leu Glu
1               5                   10                  15
```

(2) INFORMATION FOR SEQ ID NO:54:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:54:

```
Met Ile Arg Ala Gln Ala Ala Ser Leu Glu Ala Glu His Gln Ala
```

```
1               5                  10                 15
```

(2) INFORMATION FOR SEQ ID NO:55:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:55:

```
Ala Ala Ser Leu Glu Ala Glu His Gln Ala Ile Val Arg Asp Val
1               5                  10                 15
```

(2) INFORMATION FOR SEQ ID NO:56:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:56:

```
Ala Glu His Gln Ala Ile Val Arg Asp Val Leu Ala Ala Gly Asp
1               5                  10                 15
```

(2) INFORMATION FOR SEQ ID NO:57:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:57:

```
Ile Val Arg Asp Val Leu Ala Ala Gly Asp Phe Trp Gly Gly Ala
1               5                  10                 15
```

(2) INFORMATION FOR SEQ ID NO:58:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:58:

```
Leu Ala Ala Gly Asp Phe Trp Gly Gly Ala Gly Ser Val Ala Cys Gln
1               5                  10                 15
```

```
(2) INFORMATION FOR SEQ ID NO:59:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:59:

Phe Trp Gly Gly Ala Gly Ser Val Ala Cys Gln Glu Phe Ile Thr
1               5                   10                  15

(2) INFORMATION FOR SEQ ID NO:60:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:60:

Gly Ser Val Ala Cys Gln Glu Phe Ile Thr Gln Leu Gly Arg Asn
1               5                   10                  15

(2) INFORMATION FOR SEQ ID NO:61:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:61:

Gln Glu Phe Ile Thr Gln Leu Gly Arg Asn Phe Gln Val Ile Tyr Glu
1               5                   10                  15
Gln Ala (2) INFORMATION FOR SEQ ID NO:62:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:62:

Arg Asn Phe Gln Val Ile Tyr Glu Gln Ala Asn Ala His Gly Gln
1               5                   10                  15

(2) INFORMATION FOR SEQ ID NO:63:
```

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:63:

Ile Tyr Glu Gln Ala Asn Ala His Gly Gln Lys Val Gln Ala Ala
1               5                  10                  15

(2) INFORMATION FOR SEQ ID NO:64:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:64:

Asn Ala His Gly Gln Lys Val Gln Ala Ala Gly Asn Asn Met Ala
1               5                  10                  15

(2) INFORMATION FOR SEQ ID NO:65:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:65:

Lys Val Gln Ala Ala Gly Asn Asn Met Ala Gln Thr Asp Ser Ala
1               5                  10                  15

(2) INFORMATION FOR SEQ ID NO:66:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:66:

Gly Asn Asn Met Ala Gln Thr Asp Ser Ala Val Gly Ser Ser Trp Ala
1               5                  10                  15

(2) INFORMATION FOR SEQ ID NO:67:

(i) SEQUENCE CHARACTERISTICS:
            (A) LENGTH: 15 amino acids (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:67:

Asp Ala His Gly Ala Met Ile Arg Ala Leu Ala Gly Leu Leu Glu
1               5                   10                  15

(2) INFORMATION FOR SEQ ID NO:68:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:68:

Asp Ala His Gly Ala Met Ile Arg Ala Gln Ala Gly Leu Leu Glu
1               5                   10                  15

(2) INFORMATION FOR SEQ ID NO:69:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:69:

Met Ile Arg Ala Leu Ala Gly Leu Leu Glu Ala Glu His Gln Ala
1               5                   10                  15

(2) INFORMATION FOR SEQ ID NO:70:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:70:

Met Ile Arg Ala Gln Ala Gly Leu Leu Glu Ala Glu His Gln Ala
1               5                   10                  15

(2) INFORMATION FOR SEQ ID NO:71:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
    (A) ORGANISM: Mycobacterium tuberculosis (xi) SEQUENCE DESCRIPTION: SEQ ID NO:71:

```
Ala Gly Leu Leu Glu Ala Glu His Gln Ala Ile Ile Ser Asp Val
1               5                  10                  15
```

(2) INFORMATION FOR SEQ ID NO:72:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:72:

```
Ala Gly Leu Leu Glu Ala Glu His Gln Ala Ile Ile Arg Asp Val
1               5                  10                  15
```

(2) INFORMATION FOR SEQ ID NO:73:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:73:

```
Ala Glu His Gln Ala Ile Ile Ser Asp Val Leu Thr Ala Ser Asp
1               5                  10                  15
```

(2) INFORMATION FOR SEQ ID NO:74:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Mycobacterium tuberculosis (xi) SEQUENCE DESCRIPTION: SEQ ID NO:74:

```
Ala Glu His Gln Ala Ile Ile Arg Asp Val Leu Thr Ala Ser Asp
1               5                  10                  15
```

(2) INFORMATION FOR SEQ ID NO:75:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide

```
        (vi) ORIGINAL SOURCE:
             (A) ORGANISM: Mycobacterium tuberculosis (xi) SEQUENCE DESCRIPTION: SEQ ID NO:75:

Ile Ile Ser Asp Val Leu Thr Ala Ser Asp Phe Trp Gly Gly Ala
1               5                  10                  15

(2) INFORMATION FOR SEQ ID NO:76:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: peptide (vi) ORIGINAL SOURCE:
             (A) ORGANISM: Mycobacterium tuberculosis (xi) SEQUENCE DESCRIPTION: SEQ ID NO:76:

Ile Ile Arg Asp Val Leu Thr Ala Ser Asp Phe Trp Gly Gly Ala
1               5                  10                  15

(2) INFORMATION FOR SEQ ID NO:77:

(i) SEQUENCE CHARACTERISTICS:
             (A) LENGTH: 16 amino acids
             (B) TYPE: amino acid
             (C) STRANDEDNESS: single
             (D) TOPOLOGY: linear (ii) MOLECULE TYPE: peptide (vi) ORIGINAL SOURCE:
             (A) ORGANISM: Mycobacterium tuberculosis (xi) SEQUENCE DESCRIPTION: SEQ ID NO:77:

Leu Thr Ala Ser Asp Phe Trp Gly Gly Ala Gly Ser Ala Ala Cys Gln
1               5                  10                  15

(2) INFORMATION FOR SEQ ID NO:78:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: peptide (vi) ORIGINAL SOURCE:
             (A) ORGANISM: Mycobacterium tuberculosis (xi) SEQUENCE DESCRIPTION: SEQ ID NO:78:

Phe Trp Gly Gly Ala Gly Ser Ala Ala Cys Gln Gly Phe Ile Thr
1               5                  10                  15

(2) INFORMATION FOR SEQ ID NO:79:

(i) SEQUENCE CHARACTERISTICS:
             (A) LENGTH: 15 amino acids
             (B) TYPE: amino acid
             (C) STRANDEDNESS: single
             (D) TOPOLOGY: linear (ii) MOLECULE TYPE: peptide (vi) ORIGINAL SOURCE:
             (A) ORGANISM: Mycobacterium tuberculosis
```

```
        (xi) SEQUENCE DESCRIPTION: SEQ ID NO:79:

Gly Ser Ala Ala Cys Gln Gly Phe Ile Thr Gln Leu Gly Arg Asn
1               5                  10                  15

(2) INFORMATION FOR SEQ ID NO:80:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:80:

Gln Gly Phe Ile Thr Gln Leu Gly Arg Asn Phe Gln Val Ile Tyr
1               5                  10                  15

(2) INFORMATION FOR SEQ ID NO:81:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:81:

Val Thr Thr Asn Phe Phe Gly Val Asn Thr Ile Pro Ile Ala Leu Asn
1               5                  10                  15

Glu Ala Asp Tyr Leu Arg Met Trp Ile
                20                  25

(2) INFORMATION FOR SEQ ID NO:82:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Mycobacterium tuberculosis (xi) SEQUENCE DESCRIPTION: SEQ ID NO:82:

Asn Glu Ala Asp Tyr Leu Arg Met Trp Ile Gln Ala Ala Thr Val Met
1               5                  10                  15

Ser His Tyr Gln Ala Val Ala His Glu
                20                  25

(2) INFORMATION FOR SEQ ID NO:83:

(i) SEQUENCE CHARACTERISTICS:
            (A) LENGTH: 967 base pairs
            (B) TYPE: nucleic acid
            (C) STRANDEDNESS: single
            (D) TOPOLOGY: linear (ii) MOLECULE TYPE: cDNA
```

(xi) SEQUENCE DESCRIPTION: SEQ ID NO:83:

```
TGAGCGCCAA CCCTACCGTC GGTTCGTCAC ACGGACCGCA TGGCCTGCTC CGCGGACTGC        60
CGCTAGGGTC GCGGATCACT CGGCGTAGCG GCGCCTTTGC CCACCGATAT GGGTTCCGTC       120
ACAGTGTGGT TGCCCGCCCG CCATCGGCCG GATAACGCCA TGACCTCAGC TCGGCAGAAA       180
TGACAATGCT CCCAAAGGCG TGAGCACCCG AAGACAACTA AGCAGGAGAT CGCATGCCGT       240
TTGTGACTAC CAACCAGAA GCACTGGCGG CGGCGGCCGG CAGTCTGCAG GGAATCGGCT        300
CCGCATTGAA CGCCCAGAAT GCGGCTGCGG CGACTCCCAC GACGGGGTG GTCCGGCGGC        360
CGCCGATGAA NTGTCGGCGC TGACGGCGGC TCAGTTCGCG GCACACGCCC AGATCTATCA       420
GGCCGTCAGC GCCCAGGCCG CGGCGATTCA CGAGATGTTC GTCAACACTC TACAGATGAG       480
CTCAGGGTCG TATGCTGCTA CCGAGGCCGC CAACGCGGCC GCGGCCGGNT AGAGGAGTCA       540
CTGCGATGGA TTTTGGGGCG TTGCCGCCGG AGGTCAATTC GGTGCGGATG TATGCCGTTC       600
CTGGCTCGGC ACCAATGGTC GCTGCGGCGT CGGCCTGGAA CGGGTTGGCC GCGGAGCTGA       660
GTTCGGCGGC CACCGGTTAT GAGACGGTGA TCACTCAGCT CAGCAGTGAG GGGTGGCTAG       720
GTCCGGCGTC AGCGGCGATG GCCGAGGCAG TTGCGCCGTA TGTGGCGTGG ATGAGTGCCG       780
CTGCGGCGCA AGCCGAGCAG GCGGCCACAC AGGCCAGGGC CGCCGCGGCC GCTTTTGAGG       840
CGGCGTTTGC CGCGACGGTG CCTCCGCCGT TGATCGCGGC CAACCGGGCT TCGTTGATGC       900
AGCTGATCTC GACGAATGTC TTTGGTCAGA ACACCTCGGC GATCGCGGCC GCCGAAGCTC       960
AGTACGG                                                                 967
```

(2) INFORMATION FOR SEQ ID NO:84:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:84:

Met Ser Phe Val Thr Thr Gln Pro Glu Ala Leu Ala Ala Ala Ala
1               5                  10                  15

(2) INFORMATION FOR SEQ ID NO:85:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:85:

Thr Gln Pro Glu Ala Leu Ala Ala Ala Ala Ala Asn Leu Gln Gly
1               5                  10                  15

(2) INFORMATION FOR SEQ ID NO:86:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:86:

Leu Ala Ala Ala Ala Ala Asn Leu Gln Gly Ile Gly Thr Thr Met
1               5                   10                  15

(2) INFORMATION FOR SEQ ID NO:87:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:87:

Ala Asn Leu Gln Gly Ile Gly Thr Thr Met Asn Ala Gln Asn Ala
1               5                   10                  15

(2) INFORMATION FOR SEQ ID NO:88:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:88:

Ile Gly Thr Thr Met Asn Ala Gln Asn Ala Ala Ala Ala Ala Pro
1               5                   10                  15

(2) INFORMATION FOR SEQ ID NO:89:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:89:

Asn Ala Gln Asn Ala Ala Ala Ala Ala Pro Thr Thr Gly Val Val
1               5                   10                  15

(2) INFORMATION FOR SEQ ID NO:90:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:90:

Ala Ala Ala Ala Pro Thr Thr Gly Val Val Pro Ala Ala Ala Asp
1               5                   10                  15

(2) INFORMATION FOR SEQ ID NO:91:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:91:

Thr Thr Gly Val Val Pro Ala Ala Ala Asp Glu Val Ser Ala Leu
1               5                   10                  15

(2) INFORMATION FOR SEQ ID NO:92:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:92:

Pro Ala Ala Ala Asp Glu Val Ser Ala Leu Thr Ala Ala Gln Phe
1               5                   10                  15

(2) INFORMATION FOR SEQ ID NO:93:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:93:

Glu Val Ser Ala Leu Thr Ala Ala Gln Phe Ala Ala His Ala Gln
1               5                   10                  15

(2) INFORMATION FOR SEQ ID NO:94:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:94:

Thr Ala Ala Gln Phe Ala Ala His Ala Gln Met Tyr Gln Thr Val
1               5                   10                  15

(2) INFORMATION FOR SEQ ID NO:95:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:95:

Ala Ala His Ala Gln Met Tyr Gln Thr Val Ser Ala Gln Ala Ala
1               5                   10                  15

(2) INFORMATION FOR SEQ ID NO:96:

(i) SEQUENCE CHARACTERISTICS:
        (A) LENGTH: 16 amino acids
        (B) TYPE: amino acid
        (C) STRANDEDNESS: single
        (D) TOPOLOGY: linear

```
       (ii) MOLECULE TYPE: peptide (xi) SEQUENCE DESCRIPTION: SEQ ID NO:96:

Met Tyr Gln Thr Val Ser Ala Gln Ala Ala Ile His Glu Met Phe
  1               5                  10                  15

(2) INFORMATION FOR SEQ ID NO:97:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:97:

Ser Ala Gln Ala Ala Ala Ile His Glu Met Phe Val Asn Thr Leu
  1               5                  10                  15

(2) INFORMATION FOR SEQ ID NO:98:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:98:

Ala Ile His Glu Met Phe Val Asn Thr Leu Val Ala Ser Ser Gly
  1               5                  10                  15

(2) INFORMATION FOR SEQ ID NO:99:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:99:

Phe Val Asn Thr Leu Val Ala Ser Ser Gly Ser Tyr Ala Ala Thr
  1               5                  10                  15

(2) INFORMATION FOR SEQ ID NO:100:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:100:

Val Ala Ser Ser Gly Ser Tyr Ala Ala Thr Glu Ala Ala Asn Ala
  1               5                  10                  15

(2) INFORMATION FOR SEQ ID NO:101:

(i) SEQUENCE CHARACTERISTICS:
            (A) LENGTH: 14 amino acids
            (B) TYPE: amino acid
            (C) STRANDEDNESS: single
            (D) TOPOLOGY: linear
```

(ii) MOLECULE TYPE: peptide (xi) SEQUENCE DESCRIPTION: SEQ ID NO:101:

Ser Tyr Ala Ala Thr Glu Ala Ala Asn Ala Ala Ala Ala Gly
 1               5                  10

(2) INFORMATION FOR SEQ ID NO:102:

(i) SEQUENCE CHARACTERISTICS:
        (A) LENGTH: 1784 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:102:

```
ATTCGTTCCT GCCGCAGCTA AATCCCGGGG ACATCGTCGC CGGCCAGTAC GAGGTCAAAG      60
GCTGCATCGC GCACGGCGGA CTGGGCTGGA TCTACCTCGC TCTCGACCGC AATGTCAACG     120
GCCGTCCGGT GGTGCTCAAG GGCCTGGTGC ATTCCGGTGA TGCCGAAGCG CAGGCAATGG     180
CGATGGCCGA ACGCCAGTTC CTGGCCGAGG TGGTGCACCC GTCGATCGTG CAGATCTTCA     240
ACTTTGTCGA GCACACCGAC AGGCACGGGG ATCCGGTCGG CTACATCGTG ATGGAATACG     300
TCGGCGGGCA ATCGCTCAAA CGCAGCAAGG GTCANAAACT GCCCGTCGCG GAGGCCATCG     360
CCTACCTGCT GGAGATCCTG CCGGCGCTGA GCTACCTGCA TTCCATCGGC TTGGTCTACA     420
ACGACCTGAA GCCGGAAAAC ATCATGCTGA CCGAGGAACA GCTCAAGCTG ATCGACCTGG     480
GCGCGGTATC GCGGATCAAC TCGTTCGGCT ACCTCTACGG GACCCCAGGC TTCCAGGCGC     540
CCGAGATCGT GCGGACCGGT CCGACGGTGG CCACCGACAT CTACACCGTG GGACGCACGC     600
TCGCGGCGCT CACGCTGGAC CTGCCCACCC GCAATGGCCG TTATGTGGAT GGGCTACCCG     660
AAGACGACCC GGTGCTGAAA ACCTACGACT CTTACGGCCG GTTGCTGCGC AGGGCCATCG     720
ACCCCGATCC GCGGCAACGG TTCACCACCG CCGAAGAGAT GTCCGCGCAA TTGACGGGCG     780
TGTTGCGGGA GGTGGTCGCC CAGACACCGG GGTGCCGCGG CCAGGCTATC AACGATCTTC     840
AGTCCCAGTC GGTCGACATT TGGAGTGGAC TGCTGGTGGC GCACACCGAC GTGTATCTGG     900
ACGGGCAGGT GCACGCGGAG AAGCTGACCG CCAACGAGAT CGTGACCGCG CTGTCGGTGC     960
CGCTGGTCGA TCCGACCGAC GTCGCAGCTT CGGTCCTGCA GGCCACGGTG CTCTCCCAGC    1020
CGGTGCAGAC CCTAGACTCG NTGCGCGCGG CCCGCCACGG TGCGCTGGAC GCCGACGGCG    1080
TCGATTNTCC GAGTCAGTGG AGCTGCCGCT AATGGAAGTC CGCGCGCTGC TGGATCTCGG    1140
CGATGTGGCC AAGGCCACCC GAAAACTCGA CGATCTGGCC GAACGCGTTG GCTGGCGATG    1200
GCGATTGGTC TGGTACCGGG CCGTCGCCGA GCTGCTCACC GGCGACTATG ACTCGGCCAC    1260
CAAACATTTC ACCGAGGTGC TGGATACCTT TCCCGGCGAG CTGGCGCCCA AGCTCGCCCT    1320
GGCCGCCACC GCCGAACTAG CCGGCAACAC CGACGAACAC AAGTTCTATC AGACGGTGTG    1380
GAGCACCAAC GACGGCGTGA TCTCGGCGGC TTTCGGACTG GCCAGAGCCC GGTCGGCCGA    1440
AGGTGATCGG GTCGGCGCCG TGCGCACGCT CGACGAGGTA CCGCCCACTT CTCGGCATTT    1500
CACCACGGCA CGGCTGACCA GCGCGGTGAC TCTGTTGTCC GGCCGGTCAA CGAGTGAAGT    1560
CACCGAGGAA CAGATCCGCG ACGCCGCCCG AAGAGTGGAG GCGCTGCCCC CGACCGAACC    1620
ACGCGTGCTG CAGATCCGCG CCCTGGTGCT GGGTGGCGCG CTGGACTGGC TGAAGGACAA    1680
CAAGGCCAGC ACCAACCACA TCCTCGGTTT CCCGTTCACC AGTCACGGGC TGCGGCTGGG    1740
```

```
TGTCGAGGCG TCACTGCGCA GCCTGGCCCG GGTAGCTCCC ACTC                1784
```

(2) INFORMATION FOR SEQ ID NO:103:

(i) SEQUENCE CHARACTERISTICS:
  (A) LENGTH: 766 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:103:

```
ACAARACACT CGGYGGCKGC CGMTCCGGCC TGATCGTCGG TGATCAGCYT CGTGCCAAAY   60
TCGGCACAAG GTGCGCGCTR CCCAANGAGT TCTTCGCCGC RGTGCGMGCM KAACTGGCCT  120
ATCNTGGTTG GGTGCCGTCC CGCANAACCC GCGAACTTAA ACCCATTTTA ACCGGGCAGG  180
AAGTTTCCTA CATYTACCCN RGSMANCCAA CCGGGCCGCC NANAAMTCCG TCCTGGANTC  240
CGANCGGTTC CCGGTGTTCG CCGCACTGCT GACCGGCACG GARTATCCGC AGGCGGCGTT  300
GGCCAACGCG TGGGTGCAAC TGGCCTACGG TGCGCACCAS GACGCCATCA CCGGCTCGGA  360
GTCCGACCAG GTACTCAATG CTGGCGACCA CACCAGCCAG CAGACCAAAC TGGTGCACGC  420
CGATCTCCAG GCGCGCCGGC CCGGTGGCAT ACGGATTGGT CGAAACCAAT CCGAAGGAAT  480
TCATCACGGA CGGTCACGGA AAACGATCGC CCCAATGGGN GGACNACCCN AGCCAGGCGN  540
ATTNACCGTT NAACAAGTTG GNGTAGGTTC TTTGATATCG AKCAACCGAT ACGGAKCGGM  600
CCGCGGAATG GTAGACCACC ACCAGTGCCC NCAMGTMGTG CACCAGTTTG GTCATCGCCC  660
GCAGATCGGT GACCCCGCCA AGCGTTCCGG ATGCGGAGAT GASGGTGACC AGCCYGGTTG  720
ACCTGTTGAT CAGGTTNTCC CAGTGCCACG TCGGCAGCTG GCCGGT                766
```

(2) INFORMATION FOR SEQ ID NO:104:

(i) SEQUENCE CHARACTERISTICS:
  (A) LENGTH: 1231 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:104:

```
CGGCACGAGA ATGTCGCCTG TGCCTCGATA GCCACTTGCG TGTGGTCGCG CTGCCAGCGG   60
GTCAGCCAGG TCGCCTGGTC CAGGCCATCG GGCCGGCGCA GGAGCGCGAT GTTGGCCAGA  120
CCCGGTGTAC GAGAACCGGA CTCGACNAAG TGTCGGCGCT GACGGCGGCT CAGTTCGCGG  180
CACACGCCCA GATCTATCAG GCCGTCAGCG CCCAGGCCGC GGCGATTCAC GAGATGTTCG  240
TCAACACTCT ACAGATNANC TCAGGGTCGT ATGCTGCTAC CGAGGCCGCC AACGCGGCCG  300
CGGCCGGCTA GAGGAGTCAC TGCGATGGAT TTTGGGGCGT TGCCGCCGGA GGTCAATTCG  360
GTGCGGATGT ATGCCGGTCC TGGCTCGGCA CCAATGGTCG CTGCGGCGTC GGCCTGGAAC  420
GGGTTGGCCG CGGAGCTGAG TTCGGCGGCC ACCGGTTATG AGACGGTGAT CACTCAGCTC  480
AGCAGTGAGG GGTGGCTAGG TCCGGCGTCA GCGGCGATGG CCGAGGCAGT TGCGCCGTAT  540
GTGGCGTGGA TGAGTGCCGC TGCGGCGCAA GCCGAGCAGG CGGCCACACA GGCCAGGGCC  600
GCCGCGGCCG CTTTTGAGGC GGCGTTTGCC GCGACGGTGC CTCCGCCGTT GATCGCGGCC  660
AACCGGGCTT CGTTGATGCA GCTGATCTCG ACGAATGTCT TTGGTCAGAA CACCTCGGCG  720
ATCGCGGCCG CCGAAGCTCA GTACGGCGAG ATGTGGGCCC AAGACTCCGC GGCGATGTAT  780
```

```
GCCTACGCGG GCAGTTCGGC GAGCGCCTCG GCGGTCACGC CGTTTAGCAC GCCGCCGCAG    840

ATTGCCAACC CGACCGCTCA GGGTACGCAG GCCGCGGCCG TGGCCACCGC CGCCGGTACC    900

GCCCAGTCGA CGCTGACGGA GATGATCACC GGGCTACCCA ACGCGCTGCA AAGCCTCACC    960

TCACNTCTGT TGCAGTCGTC TAACGGTCCG CTGTCGTGGC TGTGGCAGAT CTTGTTCGGC   1020

ACGCCCAATT TCCCCACCTC AATTTCGGCA CTGCTGACCG ACCTGCAGCC CTACGCGAGC   1080

TTNTTNTATA ACACCGAGGG CCTGCCGTAC TTCAGCATCG GCATGGGCAA CAACTTCATT   1140

CAGTCGGCCA AGACCCTGGG ATTGATCGGC TAGGCGGCAC CGGCTGCGGT CGCGGNTGCT   1200

GGGGATNCCG CCAAGGGCTT GCCTCGTGCC G                                  1231
```

(2) INFORMATION FOR SEQ ID NO:105:

(i) SEQUENCE CHARACTERISTICS:
        (A) LENGTH: 2041 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:105:

```
CGGCACGAGC TCGTGCCGAT CAGTGCCATT GACGGCTTGT ACGACCTTCT GGGGATTGGA     60

ATACCCAACC AAGGGGGTAT CCTTTACTCC TCACTAGAGT ACTTCGAAAA AGCCCTGGAG    120

GAGCTGGCAG CAGCGTTTCC GGGTGATGGC TGGTTAGGTT CGGCCGCGGA CAAATACGCC    180

GGCAAAAACC GCAACCACGT GAATTTTTTC CAGGAACTGG CAGACCTCGA TCGTCAGCTC    240

ATCAGCCTGA TCCACGACCA GGCCAACGCG GTCCAGACGA CCCGCGACAT CCTGGAGGGC    300

GCCAAGAAAG GTCTCGAGTT CGTGCGCCCG GTGGCTGTGG ACCTGACCTA CATCCCGGTC    360

GTCGGGCACG CCCTATCGGC CGCCTTCCAN GCGCCGTTTT GCGCGGGCGC GATGGCCGTA    420

GTGGGCGGCG CGCTTGCCTA CTTGGTCGTG AAAACGCTGA TCAACGCGAC TCAACTCCTC    480

AAATTGCTTG CCAAATTGGC GGAGTTGGTC GCGGCCGCCA TTGCGGACAT CATTTCGGAT    540

GTGGCGGACA TCATCAAGGG CATCCTCGGA GAAGTGTGGG AGTTCATCAC AAACGCGCTC    600

AACGGCCTGA AGAGCTTTG GGACAAGCTC ACGGGGTGGG TGACCGGACT GTTCTCTCGA    660

GGGTGGTCGA ACCTGGAGTC CTTCTTTGCG GGCGTCCCCG GCTTGACCGG CGCGACCAGC    720

GGCTTGTCGC AAGTGACTGG CTTGTTCGGT GCGGCCGGTC TGTCCGCATC GTCGGGCTTG    780

GCTCACGCGG ATAGCCTGGC GAGCTCAGCC AGCTTGCCCG CCCTGGCCGG CATTGGGGGC    840

GGGTCCGGTT TTGGGGGCTT GCCGAGCCTG GCTCAGGTCC ATGCCGCCTC AACTCGGCAG    900

GCGCTACGGC CCCGAGCTGA TGGCCCGGTC GGCGCCGCTG CCGAGCAGGT CGGCGGGCAG    960

TCGCAGCTGG TCTCCGCGCA GGGTTCCCAA GGTATGGGCG GACCCGTAGG CATGGGCGGC   1020

ATGCACCCCT CTTCGGGGGC GTCGAAAGGG ACGACGACGA AGAAGTACTC GGAAGGCGCG   1080

GCGGCGGGCA CTGAAGACGC CGAGCGCGCG CCAGTCGAAG CTGACGCGGG CGGTGGGCAA   1140

AAGGTGCTGG TACGAAACGT CGTCTAACGG CATGGCGAGC CAAATCCATT GCTAGCCAGC   1200

GCCTAACAAC GCGCAATGCT AAACGGAAGG GACACGATCA ATGACGGAAA ACTTGACCGT   1260

CCAGCCCGAG CGTCTCGGTG TACTGGCGTC GCACCATGAC AACGCGGCGG TCGATGCNTC   1320

CTCGGGCGTC GAAGCTGCCG CTGGCCTAGG CGAATCTGTG GCGATCACTC ACGGTCCGTA   1380

CTGCTCACAG TTCAACGACA CGTTAAATGT GTACTTGACT GCCCACAATG CCCTGGGCTC   1440

GTCCTTGCAT ACGGCCGGTG TCGATCTCGC CAAAAGTCTT CGAATTGCGG CGAAGATATA   1500
```

```
TAGCGAGGCC GACGAAGCGT GGCGCAAGGC TATCGACGGG TTGTTTACCT GACCACGTTT      1560

GCTGCCCGCA GTGCAGGCCA CGACGTAGCG CAGGTCGTGT CCCTCGTAGG CGTGGATGCG      1620

ACCGGCCAGC ACCAGCACCC GGTGCGCACC GATGGGCACG GACAGTAGCT CGCCCGCATG      1680

CCCGGCTGCG GTTGGCGGCA CAAACCCGGG CAGTTCGGCC TGCGGCAGCA CGGTGGTNGG      1740

GGAGCCCAAC GCCGCAACGG CCGGTAACCA TCCCGACCCG AGCACGACCG AGACGTCATG      1800

TTCGCCGATC CCGGTGCGGT CAGCGATGAC CTGCGCCGCC CGCCGGGCCA GTTTGTCGGG      1860

ATCGGGCGC GGGTCAGCCA CACTGGGCGA GCTTAACTGA GCCGCTCGCC GGGGAGCGGG      1920

TGCTNGTCGA TGAGATACTG CGAGCATGCC AGCAGCCAGC GCATCCGACC GCGTCGAGGA      1980

ATTGGTGCGG CGCCGTGGTG GCGAGCTGGT CGAGCTGTCC CATGCCATCC ACCTCGTGCC      2040

G                                                                       2041
```

(2) INFORMATION FOR SEQ ID NO:106:

(i) SEQUENCE CHARACTERISTICS:
        (A) LENGTH: 1202 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:106:

```
GAGCTCACCG CTATCAACCA ATACTTTCTG CACTCCAAGA TGCAGGACAA CTGGGGTTTT        60

ACCGAGCTGG CGGCCCACAC CCGCGCGGAG TCGTTCGACG AAATGCGGCA CGCCGAGGAA       120

ATCACCGATC GCATCTTGTT GCTGGATGGT TTGCCGAACT ACCAGCGCAT CGGTTCGTTG       180

CGTATCGGCC AGACGCTCCG CGAGCAATTT GAGGCCGATC TGGCGATCGA ATACGACGTG       240

TTGAATCGTC TCAAGCCAGG AATCGTCATG TGCCGGAGA AACAGGACAC CACCAGCGCC       300

GTACTGCTGG AGAAAATCGT TGCCGACGAG GAAGAACACA TCGACTACTT GGAAACGCAG       360

CTGGAGCTGA TGGACAAGCT AGGAGAGGAG CTTTACTCGG CGCAGTGCGT CTCTCGCCCA       420

CCGACCTGAT GCCCGCTTGA GGATTCTCCG ATACCACTCC GGGCGCCGCT GACAAGCTCT       480

AGCATCGACT CGAACAGCGA TGGGAGGGCG GATATGGCGG GCCCCACAGC ACCGACCACT       540

GCCCCCACCG CAATCCGAGC CGGTGGCCCG CTGCTCAGTC CGGTGCGACG CAACATTATT       600

TTCACCGCAC TTGTGTTCGG GGTGCTGGTC GCTGCGACCG GCCAAACCAT CGTTGTGCCC       660

GCATTGCCGA CGATCGTCGC CGAGCTGGGC AGCACCGTTG ACCAGTCGTG GGCGGTCACC       720

AGCTATCTGC TGGGGGAAC ACTSKYGKKK KTGKKGKSKS KSRMRMKCTC GGTGATCTGC       780

TCGGCCGCAA CAGGGTGCTG CTAGGCTCCG TCGTGGTCTT CGTCGTTGGC TCTGTGCTGT       840

GCGGGTTATC GCAGACGATG ACCATGCTGG CGATCTCTCG CGCACTGCAG GGCGTCGGTG       900

CCGGTGCGAT TTCCGTCACC GCCTACGCGC TGGCCGCTGA GGTGGTCCCA CTGCGGGACC       960

GTGGCCGCTA CCAGGGCGTC TTANGTGCGG TGTTCGGTGT CAACACGGTC ACCGGTCCGC      1020

TGCTGGGGGG CTGGCTCACC GACTATCTGA GCTGGCGGTG GGCGTTCCGA CCACCAGCCC      1080

CATCACCGAC CCGATCGCGG TCATCGCGGC GAACACCGCC CTCGCGGCGT TGCGGGCAGG      1140

TCCCTTGGGG AACGTGGTCC CACAGCGCCA GAACGGTCGG AAATGCGATG GCCGACCCAC      1200

AC                                                                      1202
```

(2) INFORMATION FOR SEQ ID NO:107:

(i) SEQUENCE CHARACTERISTICS:
(A) LENGTH: 496 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:107:

```
GGCGGCGGCA GTTGGCCAGC AGTTNGGGCG GGGGAGCCGG TTCGGNGACC AAGAAATCGG      60

CCTGGGCAAG CAGCCGGGAC CGCGNACCGT GATCAGTTNG GATCGCCGGG ACCGCCGCCG     120

ACCAANGCCA TTCCGCCGNT GAGGAAGTCG GAANTNTGCG CAGTGATGAC GCCCTGCTGC     180

AACGCNTCCC GGATTGCCGA GCGGATCGCC GCCGAACGGC GGTGCTCACC ACCGGCGAGC     240

ACCCCTACNG ACAGGCCCGC ATAGCTGAAT GACGCCGGGT NACCGCCGTC CCNTCCACCG     300

NGANATCGGC CCGGANGCAA AGATCCGTCG GCGCTCCGC CTCGGCGACG ACAGCCACGT      360

TCACCCGCGC GTTATCGGTG GCCGCGATCG CATACCAGGC GCCGTCAAGG TNGCCGTYGC     420

GGTAGTCACG CACCGACAAG GTGATYTGGT CCATCGCCTN GACGGCGGGG GTGACGCTGG     480

GGGCGATCAM GTGCAC                                                    496
```

(2) INFORMATION FOR SEQ ID NO:108:

(i) SEQUENCE CHARACTERISTICS:
(A) LENGTH: 849 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:108:

```
TGGATTCCGA TAGCGGTTTC GGCCCCTCGA CGGGCGACCA CGGCGCGCAG GCCTCCGAAC      60

GGGGGGCCGG GACGCTGGGA TTCGCCGGGA CCGCAACCAA GAACGCCGG GTCCGGGCGG     120

TCGGGCTGAC CGCACTGGCC GGTGATGAGT TCGGCAACGG CCCCCGGATG CCGATGGTGC     180

CGGGGACCTG GGAGCAGGGC AGCAACGAGC CCGAGGCGCC CGACGGATCG GGGAGAGGGG     240

GAGGCGACGG CTTACCGCAC GACAGCAAGT AACCGAATTC CGAATCACGT GGACCCGTAC     300

GGGTCGAAAG GAGAGATGTT ATGAGCCTTT TGGATGCTCA TATCCCACAG TTGGTGGCCT     360

CCCAGTCGGC GTTTGCCGCC AAGGCGGGGC TGATGCGGCA CACGATCGGT CAGGCCGAGC     420

AGGCGGCGAT GTCGGCTCAG GCGTTTCACC AGGGGGAGTC GTCGGCGGCG TTTCAGGCCG     480

CCCATGCCCG GTTTGTGGCG GCGGCCGCCA AAGTCAACAC CTTGTTGGAT GTCGCGCAGG     540

CGAATCTGGG TGAGGCCGCC GGTACCTATG TGGCCGCCGA TGCTGCGGCC GCGTCGACCT     600

ATACCGGGTT CTGATCGAAC CCTGCTGACC GAGAGGACTT GTGATGTCGC AAATCATGTA     660

CAACTACCCC GCGATGTTGG GTCACGCCGG GGATATGGCC GGATATGCCG GCACGCTGCA     720

GAGCTTGGGT GCCGAGATCG CCGTGGAGCA GGCCGCGTTG CAGAGTGCGT GGCAGGGCGA     780

TACCGGGATC ACGTATCAGG CGTGGCAGGC ACANTGGTAA CCANGCCANG GAAGATTTGG     840

TGCGGGCCT                                                            849
```

(2) INFORMATION FOR SEQ ID NO:109:

(i) SEQUENCE CHARACTERISTICS:
(A) LENGTH: 97 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:109:

```
Met Ser Leu Leu Asp Ala His Ile Pro Gln Leu Val Ala Ser Gln Ser
1               5                   10                  15

Ala Phe Ala Ala Lys Ala Gly Leu Met Arg His Thr Ile Gly Gln Ala
            20                  25                  30

Glu Gln Ala Ala Met Ser Ala Gln Ala Phe His Gln Gly Glu Ser Ser
        35                  40                  45

Ala Ala Phe Gln Ala Ala His Ala Arg Phe Val Ala Ala Ala Ala Lys
    50                  55                  60

Val Asn Thr Leu Leu Asp Val Ala Gln Ala Asn Leu Gly Glu Ala Ala
65                  70                  75                  80

Gly Thr Tyr Val Ala Ala Asp Ala Ala Ala Ser Thr Tyr Thr Gly
                85                  90                  95

Phe
```

(2) INFORMATION FOR SEQ ID NO:110:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:110:

```
Met Ser Leu Leu Asp Ala His Ile Pro Gln Leu Val Ala Ser Gln
1               5                   10                  15
```

(2) INFORMATION FOR SEQ ID NO:111:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:111:

```
Ala His Ile Pro Gln Leu Val Ala Ser Gln Ser Ala Phe Ala Ala
1               5                   10                  15
```

(2) INFORMATION FOR SEQ ID NO:112:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:112:

```
Leu Val Ala Ser Gln Ser Ala Phe Ala Ala Lys Ala Gly Leu Met
1               5                   10                  15
```

(2) INFORMATION FOR SEQ ID NO:113:

(i) SEQUENCE CHARACTERISTICS:
       (A) LENGTH: 15 amino acids
       (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO:113:

Ser Ala Phe Ala Ala Lys Ala Gly Leu Met Arg His Thr Ile Gly
 1               5                  10                  15

(2) INFORMATION FOR SEQ ID NO:114:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:114:

Lys Ala Gly Leu Met Arg His Thr Ile Gly Gln Ala Glu Gln Ala
 1               5                  10                  15

(2) INFORMATION FOR SEQ ID NO:115:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:115:

Arg His Thr Ile Gly Gln Ala Glu Gln Ala Ala Met Ser Ala Gln
 1               5                  10                  15

(2) INFORMATION FOR SEQ ID NO:116:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:116:

Gln Ala Glu Gln Ala Ala Met Ser Ala Gln Ala Phe His Gln Gly
 1               5                  10                  15

(2) INFORMATION FOR SEQ ID NO:117:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:117:

Ala Met Ser Ala Gln Ala Phe His Gln Gly Glu Ser Ser Ala Ala
 1               5                  10                  15

(2) INFORMATION FOR SEQ ID NO:118:

(i) SEQUENCE CHARACTERISTICS:
        (A) LENGTH: 15 amino acids
```

(B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:118:

Ala Phe His Gln Gly Glu Ser Ser Ala Ala Phe Gln Ala Ala His
 1               5                  10                  15

(2) INFORMATION FOR SEQ ID NO:119:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:119:

Glu Ser Ser Ala Ala Phe Gln Ala Ala His Ala Arg Phe Val Ala
 1               5                  10                  15

(2) INFORMATION FOR SEQ ID NO:120:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:120:

Phe Gln Ala Ala His Ala Arg Phe Val Ala Ala Ala Ala Lys Val
 1               5                  10                  15

(2) INFORMATION FOR SEQ ID NO:121:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:121:

Ala Arg Phe Val Ala Ala Ala Ala Lys Val Asn Thr Leu Leu Asp
 1               5                  10                  15

(2) INFORMATION FOR SEQ ID NO:122:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:122:

Ala Ala Ala Lys Val Asn Thr Leu Leu Asp Val Ala Gln Ala Asn
 1               5                  10                  15

(2) INFORMATION FOR SEQ ID NO:123:

(i) SEQUENCE CHARACTERISTICS:

(A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:123:

Asn Thr Leu Leu Asp Val Ala Gln Ala Asn Leu Gly Glu Ala Ala
 1               5                  10                  15

(2) INFORMATION FOR SEQ ID NO:124:

(i) SEQUENCE CHARACTERISTICS:
          (A) LENGTH: 18 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO:124:

Val Ala Gln Ala Asn Leu Gly Glu Ala Ala Gly Thr Tyr Val Ala Ala
 1               5                  10                  15

Asp Ala (2) INFORMATION FOR SEQ ID NO:125:

(i) SEQUENCE CHARACTERISTICS:
          (A) LENGTH: 1752 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:125:

| | | | | | |
|---|---|---|---|---|---|
| CGGCACGAGA | ATGTCGCCTG | TGCCTCGATA | GCCACTTGCG | TGTGGTCGCG | CTGCCAGCGG | 60 |
| GTCAGCCAGG | TCGCCTGGTC | CAGGCCATCG | GGCCGGCGCA | GGAGCGCGAT | GTTGGCCAGA | 120 |
| CCCGGTGTAC | GAGAACCGGA | CTCGACNAAG | TGTCGGCGCT | GACGGCGGCT | CAGTTCGCGG | 180 |
| CACACGCCCA | GATCTATCAG | GCCGTCAGCG | CCCAGGCCGC | GGCGATTCAC | GAGATGTTCG | 240 |
| TCAACACTCT | ACAGATNANC | TCAGGGTCGT | ATGCTGCTAC | CGAGGCCGCC | AACGCGGCCG | 300 |
| CGGCCGGCTA | GAGGAGTCAC | TGCGATGGAT | TTTGGGGCGT | TGCCGCCGGA | GGTCAATTCG | 360 |
| GTGCGGATGT | ATGCCGGTCC | TGGCTCGGCA | CCAATGGTCG | CTGCGGCGTC | GGCCTGGAAC | 420 |
| GGGTTGGCCG | CGGAGCTGAG | TTCGGCGGCC | ACCGGTTATG | AGACGGTGAT | CACTCAGCTC | 480 |
| AGCAGTGAGG | GGTGGCTAGG | TCCGGCGTCA | GCGGCGATGG | CCGAGGCAGT | TGCGCCGTAT | 540 |
| GTGGCGTGGA | TGAGTGCCGC | TGCGGCGCAA | GCCGAGCAGG | CGGCCACACA | GGCCAGGGCC | 600 |
| GCCGCGGCCG | CTTTTGAGGC | GGCGTTTGCC | GCGACGGTGC | CTCCGCCGTT | GATCGCGGCC | 660 |
| AACCGGGCTT | CGTTGATGCA | GCTGATCTCG | ACGAATGTCT | TTGGTCAGAA | CACCTCGGCG | 720 |
| ATCGCGGCCG | CCGAAGCTCA | GTACGGCGAG | ATGTGGGCCC | AAGACTCCGC | GGCGATGTAT | 780 |
| GCCTACGCGG | GCAGTTCGGC | GAGCGCCTCG | GCGGTCACGC | CGTTTAGCAC | GCCGCCGCAG | 840 |
| ATTGCCAACC | CGACCGCTCA | GGGTACGCAG | GCCGCGGCCG | TGGCCACCGC | CGCCGGTACC | 900 |
| GCCCAGTCGA | CGCTGACGGA | GATGATCACC | GGGCTACCCA | ACGCGCTGCA | AAGCCTCACC | 960 |
| TCACNTCTGT | TGCAGTCGTC | TAACGGTCCG | CTGTCGTGGC | TGTGGCAGAT | CTTGTTCGGC | 1020 |
| ACGCCCAATT | TCCCCACCTC | AATTTCGGCA | CTGCTGACCG | ACCTGCAGCC | CTACGCGAGC | 1080 |

-continued

```
TTNTTNTATA ACACCGAGGG CCTGCCGTAC TTCAGCATCG GCATGGGCAA CAACTTCATT      1140

CAGTCGGCCA AGACCCTGGG ATTGATCGGC TAGGCGGCAC CGGCTGCGGT CGCGGCTGCT      1200

GGGGATGCCG CCAAGGGCTT GCCTGGACTG GGCGGGATGC TCGGTGGCGG GCCGGTGGCG      1260

GCGGGTCTGG GCAATGCGGC TTCGGTTGGC AAGCTGTCGG TGCCGCCGGT GTGGANTGGA      1320

CCGTTGCCCG GGTCGGTGAC TCCGGGGGCT GCTCCGCTAC CGGTGAGTAC GGTCAGTGCC      1380

GCCCCGGAGG CGGCGCCCGG AAGCCTGTTG GGCGGCCTGC CGCTANCTGG TGCGGGCGGG      1440

GCCGGCGCGG GTCCACGCTA CGGATTCCRT CCCACCGTCA TGGCTCGCCC ACCCTTCGMC      1500

GGGATAGTCG CTGCCGCAAC GTATTAACGC GCCGGCCTCG GCTGGTGTGG TCCGCTGCGG      1560

GTGGCAATTG GTCNGCGCCG AAATCTCSGT GGGTTATTTR CGGTGGGATT TTTTCCCGAA      1620

GCCGGGTTCA RCACCGGATT TCCTAACGGT CCCGCKACTC TCGTGCCGAA TTCSGCACTA      1680

AGTGACGTCC GGCGGAAACC CGTTGGGTNT GAAAGCTTCA GAAAGGCCCG CTCCCAGGGG      1740

TTCGGCAAAC GG                                                         1752
```

(2) INFORMATION FOR SEQ ID NO:126:

(i) SEQUENCE CHARACTERISTICS:
        (A) LENGTH: 400 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:126:

```
Met Asp Phe Gly Ala Leu Pro Pro Glu Val Asn Ser Val Arg Met Tyr
 1               5                  10                  15

Ala Gly Pro Gly Ser Ala Pro Met Val Ala Ala Ser Ala Trp Asn
            20                  25                  30

Gly Leu Ala Ala Glu Leu Ser Ser Ala Ala Thr Gly Tyr Glu Thr Val
            35                  40                  45

Ile Thr Gln Leu Ser Ser Glu Gly Trp Leu Gly Pro Ala Ser Ala Ala
 50                  55                  60

Met Ala Glu Ala Val Ala Pro Tyr Val Ala Trp Met Ser Ala Ala Ala
 65                  70                  75                  80

Ala Gln Ala Glu Gln Ala Ala Thr Gln Ala Arg Ala Ala Ala Ala
            85                  90                  95

Phe Glu Ala Ala Phe Ala Ala Thr Val Pro Pro Pro Leu Ile Ala Ala
            100                 105                 110

Asn Arg Ala Ser Leu Met Gln Leu Ile Ser Thr Asn Val Phe Gly Gln
            115                 120                 125

Asn Thr Ser Ala Ile Ala Ala Ala Glu Ala Gln Tyr Gly Glu Met Trp
    130                 135                 140

Ala Gln Asp Ser Ala Ala Met Tyr Ala Tyr Ala Gly Ser Ser Ala Ser
145                 150                 155                 160

Ala Ser Ala Val Thr Pro Phe Ser Thr Pro Pro Gln Ile Ala Asn Pro
                165                 170                 175

Thr Ala Gln Gly Thr Gln Ala Ala Val Ala Thr Ala Ala Gly Thr
                180                 185                 190

Ala Gln Ser Thr Leu Thr Glu Met Ile Thr Gly Leu Pro Asn Ala Leu
            195                 200                 205

Gln Ser Leu Thr Ser Xaa Leu Leu Gln Ser Ser Asn Gly Pro Leu Ser
    210                 215                 220
```

```
Trp Leu Trp Gln Ile Leu Phe Gly Thr Pro Asn Phe Pro Thr Ser Ile
225                 230                 235                 240

Ser Ala Leu Leu Thr Asp Leu Gln Pro Tyr Ala Ser Xaa Xaa Tyr Asn
                245                 250                 255

Thr Glu Gly Leu Pro Tyr Phe Ser Ile Gly Met Gly Asn Asn Phe Ile
            260                 265                 270

Gln Ser Ala Lys Thr Leu Gly Leu Ile Gly Ser Ala Ala Pro Ala Ala
            275                 280                 285

Val Ala Ala Gly Asp Ala Ala Lys Gly Leu Pro Gly Leu Gly Gly
290                 295                 300

Met Leu Gly Gly Gly Pro Val Ala Ala Gly Leu Gly Asn Ala Ala Ser
305                 310                 315                 320

Val Gly Lys Leu Ser Val Pro Pro Val Trp Xaa Gly Pro Leu Pro Gly
                325                 330                 335

Ser Val Thr Pro Gly Ala Ala Pro Leu Pro Val Ser Thr Val Ser Ala
            340                 345                 350

Ala Pro Glu Ala Ala Pro Gly Ser Leu Leu Gly Gly Leu Pro Leu Xaa
            355                 360                 365

Gly Ala Gly Gly Ala Gly Ala Gly Pro Arg Tyr Gly Phe Xaa Pro Thr
370                 375                 380

Val Met Ala Arg Pro Pro Phe Xaa Gly Ile Val Ala Ala Ala Thr Tyr
385                 390                 395                 400

(2) INFORMATION FOR SEQ ID NO:127:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:127:

GGCACGAGCA CCAGTTGACC CGCGAAGAAC CTGACCGCGC CACCCAGCGC CGCCCGCATC      60

ACCGGCCCCG TCCCACGAAC CTTTTCGGTA AACGAGCCAC TCCAGCGGAG ATCGGTACCG     120

CCCGACGCAT TTGGTGTAAG GACCACCTCG CCGAAGTAGT CCTGGACGGG TGTCCTCGCG     180

CCAACCAGCT TGTAGACGTG GCGACGGTCC TGCTCATACT CGACGGTCTC TTCCTGCACG     240

AACACCGGCC ACATGCCTAG TTTGCGGATG GCCCCGATGC CGCCGGGCGC GGGATCACCG     300

CGTCGCGCCC AACTCGATTG AGCAACGATG GCTTGGCCC AGGTCGCCCA GTTGCCACCG      360

TCTGTCACGA GCCGAAACAA GGTTGCAGCC GGCGCGCTGC TGGTCTTGGT GACCTCGAAC     420

GAAAATTTCC GACCCGACAT GCGCGACTCC CGAAACGACA ACTGAAGCTC GTGC           474

(2) INFORMATION FOR SEQ ID NO:128:

(i) SEQUENCE CHARACTERISTICS:
        (A) LENGTH: 1431 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:128:

CTGCGCGCCG GAAAAAANTA TTACTGGCAG GACCGGCAGA ATGCATGGTG ATATTCCGGT      60

GATGAGGCCG CCGAGGAACC GACTAGTGCG AGGGTCAACA CATCGGTTAT TCGTTGCCGT     120
```

-continued

```
TTAGGTCTTG GATCTGCCGG GACGGCAACG AGTTGGCAGG ACCGCTCACG CGAGCGCTGT      180

TGACAGAGTC GGTTCACGTC GAACTCGCCA CCCGTCAGAT GCGAATGATA GCCACATCGG      240

CCACACCATC GACGGCGTCG AAGTCGCCGT CGTGGGTCAC GACCGGCACC CCTTGCGACG      300

TGGCAACGGC AGCGGCCCTC ACCGGACGGG ACCGAGATCG TCGGTGGTGT CGCCAGTGAG      360

CGTTGCGAGG TCGCGGGTGC AATCCCGCAT CTGCTTGCGT ATGCCGAAGC CGCCGCAGCA      420

GCTCGTCTCG ACTCAACCAT CGGCGCCGTG CGGGCTGCCT GCGGTCAGCA GCGCAACGGG      480

TTTGCCGTTG GCAGTGATGG TGATGTCTTC GCCGGCCTGC ACGCGCCGTA GCAGCCCGGC      540

GGTGTTGTTG CGCAGTTCGC GAGACGCGAC TTCAGCAGGC ATGCTGCGGG GATCGGCTTG      600

CGCTGGGCGC GGTGTCACCG TCATGCGCTT GGGATATCAC GTGATCTATC GGCACGAAGC      660

CGCCGGATGA GCGAGGCAAA CCGCCTACAC GGGCTGCCTC GCCTTGACCG CGCCGAACGT      720

TACTGTGCCG GGGGCATCAG CACCGTATCG ATCATGTACA CCGTCGCGTG GGCGGTGTGA      780

CTCCGCCACA TACCAAACGG GCGTTGTTGA CCATGAGTCG TCGCGGGCGC CTATCACCGT      840

CAGGTCGGCA CCTTGCAGGT CTGATGGGTG CCGTCGATCC TGCTCGGACT CGCCTGGCCG      900

GCTATCACGT GGTAGGTCAG GATGCTGCTG AGCAGCTTGG CGTCAGTCTT GAGTTGATCG      960

ATAGTGGCCG CCGGCAGCTT GTCGAATGCG GCGTTGGTGG GGGCGAAAAC GGTGTACTCG     1020

CCGCCGTTGA GGGTGTCGAC CAGATTCACA TCCGGGTTCA GCTTGCCCGA CAGAGCCGAG     1080

GTCAGGGTAC TGAGCATCGG GTTGTTGGAA GCCGCGGTAG CGACCGGGTC TTGCGCCATT     1140

CCGGCCACCG ATCCGGGACC GGTGGGATTT TGCGCCGCGT ATTGCGCGCA CCCACGACCA     1200

ATCAGGTCCG CTGCGGTCAG CCATTGCCGC CGTGGTAACG GGCGCCGCCG GGCTGGTCGC     1260

CGGTTTCGGG CTGGTGTCTT GCGACACGGG TTTGGTGCTC GAACAACCCG CTAAGAACGC     1320

AATCGCGATG GCTGCGAGGC TCGCTGCTGC GGCCGGTTTG GCCTGAACGT TGATCATCGC     1380

TTCGATTCCT TGCTTCTGC GGCGGCGTTG AACGCCGTCC TCCTGGGTGG A               1431
```

(2) INFORMATION FOR SEQ ID NO:129:

(i) SEQUENCE CHARACTERISTICS:
        (A) LENGTH: 279 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:129:

```
GCACGAGAGT CGTATCTTTG CACCCAGCGC CCGTAGGAAA CCGCTGGCCT GGCTAACTCA       60

GATGCGGGCG GCCGTCGATT CGAGAGGTAA CCGATCGCCC GCCGACAATG GGTTACCCAC      120

CGAGACTGAT TGCCGCGCAG CCGCCTTCGA CGTGTAAGCG CCGGTTCGTG CATGCCCGGA      180

ACGGCTGCAC TCACGGACCT TCTACGTAGT ACGTGACGGA CTTTTACGCA TTATCGCTGA      240

CGATCTTTGC CTCCCAGGAC TCCAGAATCT ACTCGTGCC                              279
```

(2) INFORMATION FOR SEQ ID NO:130:

(i) SEQUENCE CHARACTERISTICS:
        (A) LENGTH: 1470 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:130:

```
ACCGCCACCC GCAGCCCGGA ATCACCGTCG GTAACCTGCG AATACAATTT CTTCATCGAC      60

GACTTCGCGA ACAGCGAACC CGAGCCCACC GCCTGATAGC CTTCTTCCTC GATGTTCCAA     120

CCGCCGGCGG CGTCGAACGA AACGATACGA CCCGCGCTCT GCGGGTCAGA CGCATGAATG     180

TCGTAGCCCG CCAGCAACGG CAACGCCAGC AGACCCTGCA TCGCGGCCGC CAGATTGCCA     240

CGCACCATAA TCGCCAGCCG GTTGATTTTG CCGGCAAACG TCAGCGGCAC ACCCTCGAGC     300

TTCTCGTAGT GCTCAAGTTC CACGGCATAC AGCCGGGCAA ACTCAACCGC GACCGCAGCC     360

GTGCCAGCGA TGCCGGTAGC GGTGTAGTCA TCGGTGATAT ACACCTTGCG CACATCACGC     420

CCAGAAATCA TGTTGCCCTG CGTCGAACGC CGGTCACCCG CCATGACAAC ACCGCCGGGG     480

TATTTCAGCG CGACAATGGT GGTGCCGTGC GGCAGTTGCG CATCGCCGCC TGCGAGTGGC     540

GCACCGCCGC TGATGCTTGC CGGCAGCAAC TCCGGCGCCT GGCGGCGCAG GAAGTCAAGT     600

GAAAGAAGAT AGGTCTACAG CGGGTGTTCC AGAGAGTGAA TTAATGGACA GGCGATCGGG     660

CAACGGCCAG GTCACTGTCC GCCCTTTTGG ACGTATGCGC GGACGAAGTC CTCGGCGTTC     720

TCCTCGAGGA CGTCGTCGAT TTCGTCGAGC AGATCGTCGG TCTCCTCGGT CAGCTTTTCG     780

CGACGCTCCT GGCCCGCGGC GGTGCTGCCG GCGATGTCGT CATCATCGCC GCCGCCACCG     840

CCACGCTTGG TCTGCTCTTG CGCCATCGCC GCCTCCTGCT TCCTCATGGC CTTTCAAAAG     900

GCCGCGGGTG CGCGTCACAC GCCCGCTGTC TTTCTCTCAC CTACCGGTCA ACACCAACGT     960

TTCCCGGCCT AACCAGGCTT AGCGAGGCTC AGCGGTCAGT TGCTCTACCA GCTCCACGGC    1020

ACTGTCCACC GAATCCAGCA ACGCACCAAC ATGCGCCTTA CTACCCCGCA ACGGCTCCAG    1080

CGTCGGGATG CGAACCAGCG AGTCGCCGCC AGGTCGAAGA TCACCGAGTC CCAGCTAGCC    1140

GCGGCGATAT CAGCCCCGAA CCGGCGCAGG CATTTCGCCG CGGAAATACG CGCGGGTGTC    1200

GGTCGGCGGT TCTCCACCGC ACTCAGCACC TGGTGTTTCG GTGACTAAAC GCTTTATCGA    1260

GCCGCGCGCG ACCAGCCGGT TGTACAGGCC CTTGTCCAGC CGGACATCGG AGTACTGCAG    1320

GTTGACGAGG TGCAGCCGGG GCGCCGACCA GCTCAGGTTC TCCCGCTGCC GGAAACCGTC    1380

GAGCAGCCGC AGTTTGGCCG GCCAGTCCAG CAGCTCCGCG CAATCCATCG GGTCACGCTC    1440

GAGCTGATCC AGCACGTGTG CCCAGGTTTC                                    1470

(2) INFORMATION FOR SEQ ID NO:131:

(i) SEQUENCE CHARACTERISTICS:
        (A) LENGTH: 1059 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:131:

ATTCCCATCG CTCCGGCACC TATCACCAGG TAGTCGGTTT CGATGGTTTT CGCCGGCCCT      60

TGCGTTGGCC TGGGCCACGG GTCGTTCATG GGCCCTCCTG TGCGGATTGG AATTTGTGAC     120

AACGAAATCG GGCGATCGGT GAGCAATCGT CGCCGATGCA AGACACGCTT TCGCTGCCGC     180

GGCGTCAGGT GGAGTTTAGG CCAGCGTAAC AACGTAGACC GGCCACTGAC CAAACCCCAA     240

ACCCACAAAC CCTGGACGCA TGCGGGTCTC GGGCGTCAAA TTCCGGGTAG ATATCGTATA     300

CCGATATCGG ATGCCGTAGC CTTATCGAGG CATGAGACGC CCGCTAGACC CACGCGATAT     360

TCCAGATGAG CTGCGGCGAC GGCTGGGGCT CTTGGATGCG GTGGTGATCG GCTTGGGTC     420

CATGATCGGT GCCGGAATCT TTGCTCGTGC CGAATTCGGC ACGAGCTCGT GCCGAATTCG     480
```

```
GCACGAGATT CCAATCCCCA GAAGGTCGTA CAAGCCGTCA ATGGCACTTG ATCGTTGGAT      540

CGATGATGAA CGCTCTGCTC ATGCCTGCCG CCTATCTCAA CGGTCGTCGA TTCCATGCAT      600

TAGCCTTGGT TCTGCATTGC ACGCGTAGGG CCTACAGTCT GGCTGTCATG CTTGGCCGAT      660

GTCAACAGTT TTTTTCATGC TAAGCAGATC GTCAGTTTTG AGTTCGTGAA GACGGCATGT      720

TCACTTGTTG TCGACTACAT CGTCTGCGCA CATTTGCCCT CCTGCAACTG CGCTGCGACA      780

ATGCGCCAAC CGCCGTGTAG CTCGTGCCGA ATTCGGCACG AGGATCCACC GGAGATGGCC      840

GACGACTACG ACGAGGCCTG GATGCTCAAC ACCGTGTTCG ACTATCACAA CGAGAACGCA      900

AAAGAAGAGG TCATCCATCT CGTGCCCGAC GTGAACAAGG AGAGGGGGCC CATCGAACTC      960

GTAACCAAGG TAGACAAAGA GGGACATCAG ACTCGTCTAC GATGGGGAGC CACGTTTTCA     1020

TACAAGGAAC ATCCTAAGTT TTGATTCGGG AACATCCTA                           1059
```

(2) INFORMATION FOR SEQ ID NO:132:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:132:

```
GCACGAGGCA TTGGCGGGCA TCTGCATAAA CGGTGACGTA TCAGCACAAA ACAGCGGAGA       60

GAACAACATG CGATCAGAAC GTCTCCGGTG GCTGGTAGCC GCAGAAGGTC CGTTCGCCTC      120

GGTGTATTTC GACGACTCGC ACGACTCGTG CCG                                  153
```

(2) INFORMATION FOR SEQ ID NO:133:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:133:

```
CCGCGCGGTC GATCAGCGAG CCAGGCAAAA ACTCCGTCGA GCCCGAGTCG ATGATGGTCA       60

CCCGGCGCAG CATCTGGCGA ACGATCACCT CGATGTGCTT GTCGTGGATC GACACACCTT      120

GGGCGCGGTA GACCTCCTGG ACCTCGCGAA CCAGGTGTAT CTGCACCTCG CGGGGGCCCT      180

GCACCCGCAG CACCTCATGC GGGTCGGCCG AGCCTTCCAT CAGCTGCTGG CCCACCTCGA      240

CGTGGTCGCC ATCGGAGAGC ACCCGTTCGG AACCGTCTTC GTGCTTGAAC ACCCGCAGCC      300

GCTGCCGCTT GGAGATCTTG TCGTAGACCA CTTCCTCACC GCCGTCGTCA GGAACGATGG      360

TGATCTTGTA GAACCGCTCG CCGTCCT                                         387
```

(2) INFORMATION FOR SEQ ID NO:134:

(i) SEQUENCE CHARACTERISTICS:
        (A) LENGTH: 389 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:134:

```
GTTCAGCACG GCTATCCGAT TGTGCCGTTC GCTTCGGTGG GTGCTGAACA CGGCATCGAC      60

ATCGTGCTCG ACAACGAATC CCCACTGCTG GCACCGGTCC AGTTCCTCGC CGAGAAGCTG     120

CTCGGCACCA AGACGGTCC GGCGCTGGTC CGTGGTGTCG GACTGACACC GGTACCGCGC     180

CCCGAACGGC AGTATTACTG GTTCGGCGAG CCAACCGACA CCACAGAGTT TATGGGCAG     240

CAAGCCGACG ATAACGCCGC ACGCAGGGTG CGCGAGCGTG CCGCCGCCGC TATCGAACAC     300

GGCATCGAGC TGATGCTGGC CGAGCGCGCA GCCGATCCAA ATCGATCCCT GGTCGGACGG     360

CTCTTGCGCT CGGACGCCTA AGGCGCCCC                                        389
```

(2) INFORMATION FOR SEQ ID NO:135:

(i) SEQUENCE CHARACTERISTICS:
        (A) LENGTH: 480 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:135:

```
CCCGCGGTCG GAATGATCCC CGTCTCGTCG CGCGCCCATT TGATGCTGTT GATGAGCTGT      60

TTGGAGAAGC CCGGTTGGCG TACCGGTGAG CCGGAATATC TGTTGGAAGC GTCACCGGAT     120

GTNCACATGA ANTNCNTTGN CCCNGTNGCG GTNTTGGNTG NGGNAAACAC GTGTTGTNTA     180

AGCCTTGNTG GNCTCGNAAG NGCCGTNGAC GCCTGTGTCG CCGAAGATAA TGAGCACCTG     240

ACGGTTGGCG GGATCGCCGT TATCCCAAGG AATTCCGAGG TCGGTCCCGG AGATGCCGAA     300

GCGTTCCAGG GTCTTGTTGG GGCTGTCCGG TCCGGTCACC CACTCGGCGA GGGATGTGGN     360

AGCCCCGGCG AGCGTGGCAC CAGGATCCGG CGCCGCCGCC GGAGCAGGGT CGGNNGCTGN     420

NCTGNNTTCC TNNNGCCNAA TTNNACTCCN NCNACAANCT TGNNNCCGAC TCNNACCCGN     480
```

(2) INFORMATION FOR SEQ ID NO:136:

(i) SEQUENCE CHARACTERISTICS:
        (A) LENGTH: 587 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:136:

```
GCACGAGGCT ACCGGCGCGT CGCCCGCCAT GCCCTGGATG CACGCGTAGC CACCCGTNCA      60

TNCAGCGGGT CAGCCGCCGC GTCCGGGCTT AACGCTATAG CAGCTGCAAA CAACCCAGCG     120

CCGGCAATTA CTTTGATGTT GAACCGATGA CCATNGCCTN CGNGTNCAAT CTCNTCTCTT     180

NGCGCGCCNC TATTTNNGCC ATANATTTGG TTNNANNCGN AACGCTAGAC GTATCGAGTT     240

CCTTTTCGAC CACCGGCTCA ATTGTCAGCA TCCTATGGGG AACATGAGCC CCGCCGCACC     300

GGGCCGTTTC CAAATGGTGA CGTCACAACG GTGTCACAAG CCAGCGCAAT GTCCGCGGTA     360

GGGACGCGGC GGCTGGGATC GGTGGGGTGA GCGCCCGGCT TCTCAAAGCG AGGGGAGCCC     420

CGGGACTCTT ACCGGCCGAA GGCGGCGGGT GTCACTGATC TAGGCTGACG GCCAGTGGTT     480

GNTNAGCCAA CAAGGATGAC NACAAATAAN CCGAGGANAG ACANGNGACG GNCCGANANG     540

CTNACCGGN NTTGNNCNAA NNNNACNCAC TTNTACCGNN CTTATGN                    587
```

(2) INFORMATION FOR SEQ ID NO:137:

(i) SEQUENCE CHARACTERISTICS:
    (A) LENGTH: 1200 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:137

```
CAGGCATGAG CAGAGCGTTC ATCATCGATC CAACGATCAG TGCCATTGAC GGCTTGTACG      60
ACCTTCTGGG GATTGGAATA CCCAACCAAG GGGGTATCCT TTACTCCTCA CTAGAGTACT     120
TCGAAAAAGC CCTGGAGGAG CTGGCAGCAG CGTTTCCGGG TGATGGCTGG TTAGGTTCGG     180
CCGCGGACAA ATACGCCGGC AAAAACCGCA ACCACGTGAA TTTTTTCCAG GAACTGGCAG     240
ACCTCGATCG TCAGCTCATC AGCCTGATCC ACGACCAGGC CAACGCGGTC CAGACGACCC     300
GCGACATCCT GGAGGGCGCC AAGAAAGGTC TCGAGTTCGT GCGCCCGGTG GCTGTGGACC     360
TGACCTACAT CCCGGTCGTC GGGCACGCCC TATCGGCCGC CTTCCAGGCG CCGTTTTGCG     420
CGGGCGCGAT GGCCGTAGTG GGCGGCGCGC TTGCCTACTT GGTCGTGAAA ACGCTGATCA     480
ACGCGACTCA ACTCCTCAAA TTGCTTGCCA AATTGGCGGA GTTGGTCGCG GCCGCCATTG     540
CGGACATCAT TTCGGATGTG GCGGACATCA TCAAGGGCAC CCTCGGAGAA GTGTGGGAGT     600
TCATCACAAA CGCGCTCAAC GGCCTGAAAG AGCTTTGGGA CAAGCTCACG GGGTGGGTGA     660
CCGGACTGTT CTCTCGAGGG TGGTCGAACC TGGAGTCCTT CTTTGCGGGC GTCCCCGGCT     720
TGACCGGCGC GACCAGCGGC TTGTCGCAAG TGACTGGCTT GTTCGGTGCG GCCGGTCTGT     780
CCGCATCGTC GGGCTTGGCT CACGCGGATA GCCTGGCGAG CTCAGCCAGC TTGCCCGCCC     840
TGGCCGGCAT TGGGGGCGGG TCCGGTTTTG GGGGCTTGCC GAGCCTGGCT CAGGTCCATG     900
CCGCCTCAAC TCGGCAGGCG CTACGGCCCC GAGCTGATGG CCCGGTCGGC GCCGCTGCCG     960
AGCAGGTCGG CGGGCAGTCG CAGCTGGTCT CCGCGCAGGG TTCCCAAGGT ATGGGCGGAC    1020
CCGTAGGCAT GGGCGGCATG CACCCCTCTT CGGGGGCGTC GAAAGGGACG ACGACGAAGA    1080
AGTACTCGGA AGGCGCGGCG GCGGGCACTG AAGACGCCGA GCGCGCGCCA GTCGAAGCTG    1140
ACGCGGGCGG TGGGCAAAAG GTGCTGGTAC GAAACGTCGT CTAACGGCAT GGCGAGCCAA    1200
```

(2) INFORMATION FOR SEQ ID NO:138:

(i) SEQUENCE CHARACTERISTICS:
    (A) LENGTH: 392 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:138:

```
Met Ser Arg Ala Phe Ile Ile Asp Pro Thr Ile Ser Ala Ile Asp Gly
 1               5                  10                  15

Leu Tyr Asp Leu Leu Gly Ile Gly Ile Pro Asn Gln Gly Gly Ile Leu
            20                  25                  30

Tyr Ser Ser Leu Glu Tyr Phe Glu Lys Ala Leu Glu Glu Leu Ala Ala
        35                  40                  45

Ala Phe Pro Gly Asp Gly Trp Leu Gly Ser Ala Ala Asp Lys Tyr Ala
    50                  55                  60

Gly Lys Asn Arg Asn His Val Asn Phe Phe Gln Glu Leu Ala Asp Leu
65                  70                  75                  80
```

```
Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
            115                 120                 125

Leu Ser Ala Ala Phe Gln Ala Pro Phe Cys Ala Gly Ala Met Ala Val
            130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Thr
                180                 185                 190

Leu Gly Glu Val Trp Glu Phe Ile Thr Asn Ala Leu Asn Gly Leu Lys
                195                 200                 205

Glu Leu Trp Asp Lys Leu Thr Gly Trp Val Thr Gly Leu Phe Ser Arg
            210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
                260                 265                 270

Ser Ala Ser Leu Pro Ala Leu Ala Gly Ile Gly Gly Ser Gly Phe
                275                 280                 285

Gly Gly Leu Pro Ser Leu Ala Gln Val His Ala Ala Ser Thr Arg Gln
                290                 295                 300

Ala Leu Arg Pro Arg Ala Asp Gly Pro Val Gly Ala Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Met His Pro Ser Ser Gly Ala Ser
                340                 345                 350

Lys Gly Thr Thr Thr Lys Lys Tyr Ser Glu Gly Ala Ala Ala Gly Thr
            355                 360                 365

Glu Asp Ala Glu Arg Ala Pro Val Glu Ala Asp Ala Gly Gly Gly Gln
            370                 375                 380

Lys Val Leu Val Arg Asn Val Val
385                 390
```

(2) INFORMATION FOR SEQ ID NO:139:

(i) SEQUENCE CHARACTERISTICS:
        (A) LENGTH: 439 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:139:

```
ACGTTTACCC ATGCCGTCGG TGCAGAGCAA CGCCAGACAA CACAAAGTAG TCTAATTCCG      60

TTATAAAGCA GACATTTCCG TGGTTATGTA GAAGATGTCG ACCGATCAGA TGAAGCGATC     120

CGCGTCAGGT GGTATCCGAT GTCTTTTGTG ACCATCCAGC CGGTGGTCTT GGCAGCCGCG     180
```

-continued

| | | | | |
|---|---|---|---|---|
| ACGGGGGACT | TGCCGACGAT | CGGTACCGCC | GTGAGTGCTC | GGAACACAGC | CGTCTGTGCC | 240 |
| CCGACGACGG | GGGTGTTACC | CCCTGCTGCC | AATGACGTGT | CGGTCCTGAC | GGCGGCCCGG | 300 |
| TTCACCGCGC | ACACCAAGCA | CTACCGAGTG | GTGAGTAAGC | CGGCCGCGCT | GGTCCATGGC | 360 |
| ATGTTCGTGG | CCCTCCCGGC | GGCCACCGCC | GATGCGTATG | CGACCACCGA | GGCCGTCAAT | 420 |
| GTGGTCGCGA | CCGGTTAAG | | | | | 439 |

(2) INFORMATION FOR SEQ ID NO:140:

(i) SEQUENCE CHARACTERISTICS:
  (A) LENGTH: 1441 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:140

| | | | | | | |
|---|---|---|---|---|---|---|
| GAGGTTGCTG | GCAATGGATT | TCGGGCTTTT | ACCTCCGGAA | GTGAATTCAA | GCCGAATGTA | 60 |
| TTCCGGTCCG | GGGCCGGAGT | CGATGCTAGC | CGCCGCGGCC | GCCTGGGACG | GTGTGGCCGC | 120 |
| GGAGTTGACT | TCCGCCGCGG | TCTCGTATGG | ATCGGTGGTG | TCGACGCTGA | TCGTTGAGCC | 180 |
| GTGGATGGGG | CCGGCGGCGG | CCGCGATGGC | GGCCGCGGCA | ACGCCGTATG | TGGGGTGGCT | 240 |
| GGCCGCCACG | GCGGCGCTGG | CGAAGGAGAC | GGCCACACAG | GCGAGGGCAG | CGGCGGAAGC | 300 |
| GTTTGGGACG | GCGTTCGCGA | TGACGGTGCC | ACCATCCCTC | GTCGCGGCCA | ACCGCAGCCG | 360 |
| GTTGATGTCG | CTGGTCGCGG | CGAACATTCT | GGGGCAAAAC | AGTGCGGCGA | TCGCGGCTAC | 420 |
| CCAGGCCGAG | TATGCCGAAA | TGTGGGCCCA | AGACGCTGCC | GTGATGTACA | GCTATGAGGG | 480 |
| GGCATCTGCG | GCCGCGTCGG | CGTTGCCGCC | GTTCACTCCA | CCCGTGCAAG | GCACCGGCCC | 540 |
| GGCCGGGCCC | GCGGCCGCAG | CCGCGGCGAC | CCAAGCCGCC | GGTGCGGGCG | CCGTTGCGGA | 600 |
| TGCACAGGCG | ACACTGGCCC | AGCTGCCCCC | GGGGATCCTG | AGCGACATTC | TGTCCGCATT | 660 |
| GGCCGCCAAC | GCTGATCCGC | TGACATCGGG | ACTGTTGGGG | ATCGCGTCGA | CCCTCAACCC | 720 |
| GCAAGTCGGA | TCCGCTCAGC | CGATAGTGAT | CCCCACCCCG | ATAGGGGAAT | TGGACGTGAT | 780 |
| CGCGCTCTAC | ATTGCATCCA | TCGCGACCGG | CAGCATTGCG | CTCGCGATCA | CGAACACGGC | 840 |
| CAGACCCTGG | CACATCGGCC | TATACGGGAA | CGCCGGCGGG | CTGGGACCGA | CGCAGGGCCA | 900 |
| TCCACTGAGT | TCGGCGACCG | ACGAGCCGGA | GCCGCACTGG | GGCCCCTTCG | GGGGCGCGGC | 960 |
| GCCGGTGTCC | GCGGGCGTCG | GCCACGCAGC | ATTAGTCGGA | GCGTTGTCGG | TGCCGCACAG | 1020 |
| CTGGACCACG | GCCGCCCCGG | AGATCCAGCT | CGCCGTTCAG | GCAACACCCA | CCTTCAGCTC | 1080 |
| CAGCGCCGGC | GCCGACCCGA | CGGCCCTAAA | CGGGATGCCG | GCAGGCCTGC | TCAGCGGGAT | 1140 |
| GGCTTTGGCG | AGCCTGGCCG | CACGCGGCAC | GACGGGCGGT | GGCGGCACCC | GTAGCGGCAC | 1200 |
| CAGCACTGAC | GGCCAAGAGG | ACGGCCGCAA | ACCCCCGGTA | GTTGTGATTA | GAGAGCAGCC | 1260 |
| GCCGCCCGGA | AACCCCCGC | GGTAAAAGTC | CGGCAACCGT | TCGTCGCCGC | GCGGAAAATG | 1320 |
| CCTGGTGAGC | GTGGCTATCC | GACGGGCCGT | TCACACCGCT | TGTAGTAGCG | TACGGCTATG | 1380 |
| GACGACGGTG | TCTGGATTCT | CGGCGGCTAT | CAGAGCGATT | TTGCTCGCAA | CCTCAGCAAA | 1440 |
| G | | | | | | 1441 |

(2) INFORMATION FOR SEQ ID NO:141:

(i) SEQUENCE CHARACTERISTICS:
  (A) LENGTH: 99 amino acids
  (B) TYPE: amino acid (C) STRANDEDNESS: single
            (D) TOPOLOGY: linear (ii) MOLECULE TYPE: protein (xi) SEQUENCE DESCRIPTION: SEQ ID NO:141:

Met Ser Phe Val Thr Ile Gln Pro Val Val Leu Ala Ala Thr Gly
 1               5                  10                  15

Asp Leu Pro Thr Ile Gly Thr Ala Val Ser Ala Arg Asn Thr Ala Val
                20                  25                  30

Cys Ala Pro Thr Thr Gly Val Leu Pro Pro Ala Ala Asn Asp Val Ser
                35                  40                  45

Val Leu Thr Ala Ala Arg Phe Thr Ala His Thr Lys His Tyr Arg Val
 50                      55                  60

Val Ser Lys Pro Ala Ala Leu Val His Gly Met Phe Val Ala Leu Pro
 65                  70                  75                  80

Ala Ala Thr Ala Asp Ala Tyr Ala Thr Thr Glu Ala Val Asn Val Val
                85                  90                  95

Ala Thr Gly (2) INFORMATION FOR SEQ ID NO:142:

(i) SEQUENCE CHARACTERISTICS:
        (A) LENGTH: 423 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:142:

Met Asp Phe Gly Leu Leu Pro Pro Glu Val Asn Ser Ser Arg Met Tyr
 1               5                  10                  15

Ser Gly Pro Gly Pro Glu Ser Met Leu Ala Ala Ala Ala Trp Asp
                20                  25                  30

Gly Val Ala Ala Glu Leu Thr Ser Ala Ala Val Ser Tyr Gly Ser Val
                35                  40                  45

Val Ser Thr Leu Ile Val Glu Pro Trp Met Gly Pro Ala Ala Ala Ala
 50                  55                  60

Met Ala Ala Ala Thr Pro Tyr Val Gly Trp Leu Ala Ala Thr Ala
 65                  70                  75                  80

Ala Leu Ala Lys Glu Thr Ala Thr Gln Ala Arg Ala Ala Ala Glu Ala
                85                  90                  95

Phe Gly Thr Ala Phe Ala Met Thr Val Pro Pro Ser Leu Val Ala Ala
                100                 105                 110

Asn Arg Ser Arg Leu Met Ser Leu Val Ala Ala Asn Ile Leu Gly Gln
                115                 120                 125

Asn Ser Ala Ala Ile Ala Ala Thr Gln Ala Glu Tyr Ala Glu Met Trp
                130                 135                 140

Ala Gln Asp Ala Ala Val Met Tyr Ser Tyr Glu Gly Ala Ser Ala Ala
145                 150                 155                 160

Ala Ser Ala Leu Pro Pro Phe Thr Pro Val Gln Gly Thr Gly Pro
                165                 170                 175

Ala Gly Pro Ala Ala Ala Ala Ala Thr Gln Ala Ala Gly Ala Gly
                180                 185                 190

Ala Val Ala Asp Ala Gln Ala Thr Leu Ala Gln Leu Pro Pro Gly Ile
                195                 200                 205

```
Leu Ser Asp Ile Leu Ser Ala Leu Ala Ala Asn Ala Asp Pro Leu Thr
        210                 215                 220

Ser Gly Leu Leu Gly Ile Ala Ser Thr Leu Asn Pro Gln Val Gly Ser
225                 230                 235                 240

Ala Gln Pro Ile Val Ile Pro Thr Pro Ile Gly Glu Leu Asp Val Ile
                245                 250                 255

Ala Leu Tyr Ile Ala Ser Ile Ala Thr Gly Ser Ile Ala Leu Ala Ile
                260                 265                 270

Thr Asn Thr Ala Arg Pro Trp His Ile Gly Leu Tyr Gly Asn Ala Gly
            275                 280                 285

Gly Leu Gly Pro Thr Gln Gly His Pro Leu Ser Ser Ala Thr Asp Glu
290                 295                 300

Pro Glu Pro His Trp Gly Pro Phe Gly Gly Ala Ala Pro Val Ser Ala
305                 310                 315                 320

Gly Val Gly His Ala Ala Leu Val Gly Ala Leu Ser Val Pro His Ser
                325                 330                 335

Trp Thr Thr Ala Ala Pro Glu Ile Gln Leu Ala Val Gln Ala Thr Pro
            340                 345                 350

Thr Phe Ser Ser Ser Ala Gly Ala Asp Pro Thr Ala Leu Asn Gly Met
            355                 360                 365

Pro Ala Gly Leu Leu Ser Gly Met Ala Leu Ala Ser Leu Ala Ala Arg
        370                 375                 380

Gly Thr Thr Gly Gly Gly Gly Thr Arg Ser Gly Thr Ser Thr Asp Gly
385                 390                 395                 400

Gln Glu Asp Gly Arg Lys Pro Pro Val Val Val Ile Arg Glu Gln Pro
                405                 410                 415

Pro Pro Gly Asn Pro Pro Arg
            420

(2) INFORMATION FOR SEQ ID NO:143:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:143:

Met Ser Leu Leu Asp Ala His Ile Pro Gln Leu Val Ala Ser Gln Ser
1               5                   10                  15

Ala Phe Ala Ala Lys Ala Gly Leu Met Arg His Thr Ile Gly Gln Ala
                20                  25                  30

Glu Gln Ala Ala Met Ser Ala Gln Ala Phe His Gln Gly Glu Ser Ser
            35                  40                  45

Ala Ala Phe Gln Ala Ala His Ala Arg Phe Val Ala Ala Ala Ala Lys
        50                  55                  60

Val Asn Thr Leu Leu Asp Val Ala Gln Ala Asn Leu Gly Glu Ala Ala
65                  70                  75                  80

Gly Thr Tyr Val Ala Ala Asp Ala Ala Ala Ser Thr Tyr Thr Gly
                85                  90                  95

Phe (2) INFORMATION FOR SEQ ID NO:144:

(i) SEQUENCE CHARACTERISTICS:
```

```
            (A) LENGTH: 99 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:144:

Cys Arg Leu Cys Leu Asp Ser His Leu Arg Val Val Ala Leu Pro Ala
1               5                   10                  15

Gly Gln Pro Gly Arg Leu Val Gln Ala Ile Gly Pro Ala Gln Glu Arg
            20                  25                  30

Asp Val Gly Gln Thr Arg Cys Thr Arg Thr Gly Leu Asp Xaa Val Ser
            35                  40                  45

Ala Leu Thr Ala Ala Gln Phe Ala Ala His Ala Gln Ile Tyr Gln Ala
        50                  55                  60

Val Ser Ala Gln Ala Ala Ala Ile His Glu Met Phe Val Asn Thr Leu
65                  70                  75                  80

Gln Xaa Xaa Ser Gly Ser Tyr Ala Ala Thr Glu Ala Ala Asn Ala Ala
                85                  90                  95

Ala Ala Gly
```